US005748907A

United States Patent [19]

Crane

[11] Patent Number: 5,748,907
[45] Date of Patent: May 5, 1998

[54] MEDICAL FACILITY AND BUSINESS: AUTOMATIC INTERACTIVE DYNAMIC REAL-TIME MANAGEMENT

[76] Inventor: Harold E. Crane, P.O. Box 6169, Kingwood, Tex. 77325-6169

[21] Appl. No.: 739,813

[22] Filed: Oct. 30, 1996

Related U.S. Application Data

[63] Continuation of Ser. No. 140,550, Oct. 25, 1993, abandoned.
[51] Int. Cl.$^6$ ...................................................... G06F 17/60
[52] U.S. Cl. .................................... 395/202; 395/209
[58] Field of Search .................................. 395/202, 203, 395/207–210, 228, 232, 230; 364/468.06, 468.15, 468.22

[56] References Cited

U.S. PATENT DOCUMENTS

| | | |
|---|---|---|
| 4,334,425 | 6/1982 | Crane . |
| 4,843,575 | 6/1989 | Crane . |
| 5,065,315 | 11/1991 | Garcia . |
| 5,070,452 | 12/1991 | Doyle, Jr. et al. . |
| 5,077,666 | 12/1991 | Brimm et al. . |
| 5,101,476 | 3/1992 | Kukla . |
| 5,301,105 | 4/1994 | Cummings, Jr. . |
| 5,319,543 | 6/1994 | Wilhelm . |
| 5,361,202 | 11/1994 | Dove . |
| 5,369,570 | 11/1994 | Parad . |

*Primary Examiner*—Robert A. Weinhardt
*Attorney, Agent, or Firm*—Foley & Lardner

[57] ABSTRACT

An Interactive Dynamic Real-time Management System includes a microprocessor adapted to sense the automatic interaction of real-time inputs relating to the method of controlling the position, flow of patients, employees, invoicing, appointment scheduling, and financial costs; also controlling of time, space, and tasks automatically of a medical clinic or other types of businesses with this automatic interactive management system. A memory stores historical data related to the interaction of the real-time inputs, and the microprocessor compares sensed real-time information with historical data to determine changes in unknown operating parameters. All information from real-time dynamic interacting, automatic, semiautomatic and manual inputs are fed into a master processor where the information is automatically sent to patients, employees, and other businesses in the network. The information generated by the automatic interacting network allows the control of a business in a more efficient manner using fewer people, and operating at lower costs in less time, smaller space, less hardware and less paper work. The quality and detail of information generated by the system eliminates many of the data gathering and analytical functions traditionally performed by management personnel. The system utilizes "dynamic creative interrogation" which replaces the intuitive judgement of management personnel based on historical, after-the-fact information gathering with real-time solutions.

48 Claims, 28 Drawing Sheets

MEDICAL FACILITY AND BUSINESS: AUTOMATIC INTERACTIVE DYNAMIC REAL-TIME MANAGEMENT

This application is a continuation of application Ser. No. 08/140,550, filed Oct. 25, 1993, now abandoned.

BACKGROUND OF THE INVENTION

1. Field of the Invention

This invention relates to the operation and management of medical facilities and businesses such as hospitals, clinics, manufacturing and chemical process plants, which employ people that perform duties within its network of expertise, and more particularly to an interactive electronic real-time system to control the business management and the employees and customers in a more efficient and cost saving operation.

2. Discussion of Related Art

Business management systems referred to in this application are related to businesses and medical facilities such as hospitals, clinics, manufacturing plants, and insurance companies, with a few or thousands of employees. Such businesses are extremely expensive to operate. The rising costs of medical care or manufacturing labor costs of employees are so expensive that small changes in a method of management can save untold amounts of money and increase efficiency.

For example, the medical industry is trying to lower operating costs and costs to patients. On the other hand, businesses want to reduce the level of care or reduce the cost of care. In addition, patients are being charged for tests they do not need or are charged for services they do not receive. Much time and paperwork is required to function in these health care systems.

Hospital business management systems include computer hardware and software for entering patient information and printing invoices. These business management systems address administrative issues only. Nurses, patients and hospital staff are left to their own senses when it comes to managing the flow of patients, medicine, doctors, nurses and other employees through the health care system. They have little control over how much waiting takes place, resulting in more time spent in the facilities and inefficiencies on top of already high overhead costs.

Costs and Access

Various methods to attempt to cut medical costs are being used but are not working. It is notable that the method by which the patient is handled or directed in the current health care system has never changed. Many attempts at cost cutting deal with setting cost caps. These are not affecting the process by which the high costs are generated in the first place. Despite levels of care made feasible by many new methods to cure illness, new equipment to improve care, plus new medications, costs continue to rise. It is gradually becoming more difficult to afford even proper care. People can live longer and receive better care, but costs are eliminating the ability of people to afford these levels of care.

If the process by which costs are generated is not changed, some options are to start cutting the range of benefits and have providers, employers and employees share more of the cost burden. This is happening today.

The key to cutting costs is increasing the efficiency of the health care system.

Employers and insurance companies must continue to show a profit. They are reacting to the situation by raising premiums and passing the costs onto the patient. Meanwhile, costs in medical care are rising faster than the operating costs of other industries. The best long term viable option is to change the business management system, thereby increasing the efficiency of the health care system, and then to implement further changes.

Today, health care systems are not designed for the convenience of the patient, that is, the customer. They are designed strictly to get patients treated. Often, taking the patient's dignity, time and convenience into consideration would interfere with a medical facility management system. A medical facility management system is focused on keeping the medical staff and investments in hospitals and equipment highly utilized, not on the process of how costs are generated and how the patient is moved through the health care system.

The structure of today's health care system—the buildings, employees, and the operational management systems—are firmly in place. They do not change. The management system relating to dealing with patients has not ever changed. In fact, it is getting worse, judging by the amount of magazines in waiting rooms.

Businesses make many changes when forced to in order to show a profit. Historically, no matter what is changed, the structure of the business management system typically remains the same. In many cases, existing processes are computerized and automated without changing how the business is managed. This usually just aggravates the existing problems and creates information overload. There may be fewer people, but the system is still fundamentally the same. Clearly, traditional techniques for changing business management systems are no more than historical, after-the-fact attempts at information gathering, and do little to solve immediate, real-world problems at the time that they exist. There have been efforts to improve on current methodology of business management systems. These efforts largely center around the use of computers to speed up the data-gathering process.

Also, due to resulting inefficiencies, employees have higher stress levels and spend less time dealing with patients and more time with administration. This puts the health care professionals out of their areas of expertise and practical knowledge, and adds confusion and overloaded situations, which in turn all cause additional inefficiencies.

The patient's time is also becoming a significant cost factor. Time spent waiting for treatment, running around to various offices, locations, testing facilities, all adds up to time away from being at work, running a family and performing day to day responsibilities. Employers and family must pick up the difference. Patients are swamped in paperwork, terminology, and feel they are along for a ride over which they have no control.

A Typical Scenario in Today's System

You are sick. You call a doctor's office for an appointment. When you arrive for your appointment, you talk to someone who turns you over to someone else to have you fill out forms. These forms include your medical history, your immediate problem, name, address, place of work, and forms for insurance coverage. Then you sit and wait.

When you are called into a room, a nurse does a pre-exam. Then you wait again. Finally, the doctor comes in, checks your chart, gets an update from the nurse, examines you and recommends tests if necessary. A large clinic or hospital may have the tests available on-site; otherwise, you are sent to another place for these tests, often to several different locations according to the tests required. In many cases, this means going through your name, background and insurance information all over again. You may then have to return at a later date to the original doctor's office for discussions of results, and prescriptions. This means an additional trip to the pharmacy.

This all involves quite a bit of travel back and forth, and a tremendous amount of time away from work, children, or other responsibilities. From a patient's perspective, many issues and drawbacks are raised:

How many hours does the patient spend going through the complete process? How many miles has the patient travelled to complete the cycle, including treatment and medication? How well informed is the patient to record all this activity correctly with their insurance carrier, be it private or government? Is the patient getting an education out of it, or is the patient swamped in paperwork and caught in a whirlwind of an unfamiliar process? What if the patient does not get paid for time lost at work? What if it takes 90 days for the patient to get his or her money back but the doctor or hospital insists on payment in 30–60 days?

Current Attempts to Remedy these Problems

Hospitals are beginning to compete for patients in the same town, causing duplication of expensive equipment and increased overheads. Hospitals are also trying to improve their bottom lines by competing for doctors, having the doctors send their patients through the hospital. This does nothing for cutting the cost of providing health care. It only strives to improve the bottom line and income of a single hospital.

Insurers and the United States Government with Medicare and Medicaid are attempting to cut costs by using computers to speed the paperwork flow. Nevertheless, existing business management systems for a single market, such as the employee health care benefits for companies across several states, often involve thousands of forms, which must still be printed and completed by patients.

Presently, several employers and insurance companies are writing custom health care policies for their employees. Employers are taking things into their own hands by opening up clinics for their employees and then putting the medical staff on the payroll. This forces caps on the earnings for the doctors and gives the insurer better control over the magnitude of what the health care plan is covering. The underlying system of how costs are generated as the patient flows through the system, however, is still not addressed. This also puts the employer into the medical business, out of its area of expertise, along with all of its costs and overhead that must be managed.

Doctors and their private practices today are responsible for setting up and managing employees, nurses, administration, and ensuring their practice is operating efficiently. Each private practice is like a small business: many of them are run differently, some are run efficiently, some not. It is up to the doctor's capability as a business manager to determine how costs will be controlled.

These approaches address the effect—the symptoms—of how the delivery of health care is managed, not the causes—or the management system itself. In terms of a cause-effect relationship, present approaches are indirect, and management typically is performed with historical, after-the-fact data from which conclusions must manually or semiautomatically be derived. Often, this creates long delays as analysis and data gathering postpone the reaching of conclusions by management. After analysis is complete, costs of these previously undetected inefficiencies may now be quite high, and may in turn have caused other inefficiencies for which no data for analysis was gathered. This puts management's mode of operation in a look-back mode, and forces it to look at the process it is managing in a static mode, through a snapshot of derived information.

This invention proposes a method by which management can solve problems as they occur, in real-time. Data gathering occurs in real-time, automatically, and a combination of real-time data and historical data is interacted in real-time to create—not derive—results and information for management. Management is put in a dynamic mode, since it is affecting its process as it moves and operates, as opposed to looking at data describing something that occurred in the past—a static mode. The cause-effect relationship now shifts from indirect to direct, putting management in direct control over the efficiency of the process, and putting management in direct control over how costs are generated.

The present invention is an improvement on the applicant's U.S. Pat. No. 4,843,575 issued Jun. 27, 1989, and No. 4,334,425, issued Jun. 15, 1982 (both incorporated herein by reference), adapted specifically for medical facilities. However, many of the components of the first aforementioned patent can be used directly in the present invention, and the disclosure of the aforementioned patents, which are explicitly incorporated by reference for all purposes, may be referred to for further explanation of these components.

SUMMARY OF THE INVENTION

Objects

It is an object of this invention to provide a management system for improving the operation and management of medical facilities and businesses.

It is another object of the invention to provide a management system which is real-time.

It is yet another object of the invention to provide a management system which is dynamic, interactive, and fully automatic.

It is a feature of this invention that the management system interacts real-time data inputs, historical data, status information, and facility configuration aspects from inputs within the facility and from inputs outside the facility through communications links, to automatically provide outputs in real-time for managing a medical facility or business. The inputs can be provided in a combination of fully automatic, semiautomatic, or manual means.

Another object of the invention is to provide a dynamic, interactive, fully automatic real-time management system which controls and directs patient and employee flow and controls patient and employee locations in a medical facility or business. It is a feature of the invention that it automatically makes decisions on which tasks are to be performed, when and in which order these tasks are to be performed, and automatically displays this information at the required locations at the required time for the patients and employees throughout the medical facility or business.

Another object of the invention is to provide a dynamic, interactive, fully automatic real-time management system which controls and directs patient and employee information flow and controls the location of patient historical data in a medical facility or business. A feature of the invention is that, while automatically controlling and directing the flow of employees and patients, the automatic management system displays the historical data at the required locations at the required time automatically for use by employees, patients, and other organizations connected with the medical facility or business.

Another feature of the invention is that operating data concerning a medical facility or business is stored over a long period of time to aid in a computer analysis of the efficiency of the medical facility or business by interacting real-time generated data with past recorded data. It is an object of the invention to provide a management system to determine the relative operating efficiency of the medical facility or business compared to the operating efficiency of the medical facility or business in the past under similar conditions. It is a feature of the invention that these interactions are also performed for selection of specific tasks for the employees in the medical facility or business.

Another feature of the invention is that an employee of a medical facility or business is able to interact with the management system in order to aid in the development and the storage of data for future use as well as aid in the decision making and draw conclusions about the health status of a patient and the efficiency of the medical facility or business based on real-time information provided by the management system.

Another feature of the invention is that electronic measurement and test equipment of a medical facility or business is able to interact with the management system in order to store data for future use. It is an object of the invention to aid in drawing conclusions about the health status of a patient and the efficiency of the medical facility or business.

An even further object of the invention is to provide a dynamic, interactive, fully automatic real-time management system in which an owner of a medical facility or business is able to automatically obtain a profit or loss statement of the medical facility or business on a daily, weekly, or monthly basis. It is a feature of the invention that the statement may be obtained by just entering a code number.

A further object of the invention is to provide a dynamic, interactive, fully automatic real-time management system which automatically verifies and invoices insurance companies or other parties responsible for payment for services provided at a medical facility or business at the time of conclusion of those services via a communications link. An advantage of the invention is that the same communications link may also be used to provide the management system with coverage plan information and automatic enrollment of patients by the insurer or other organizations.

A further object of the invention is to provide a dynamic, interactive, fully automatic real-time management system of a medical facility or business which makes available on demand, on-line, and in real-time, historical patient data to authorized organizations located outside the medical facility or business via a communications link. An advantage of the invention is that such outside organizations can be doctors at other medical facilities or private practices, other medical facilities, and businesses whose employees are enrolled at the clinic. Another advantage is that the same communications link may also be used by the automatic management system to provide for automatic enrollment of patients from these outside organizations.

A further object of the invention is to provide a dynamic, interactive, fully automatic real-time management system which automatically schedules appointments through the medical facility or business without overloading the medical facility or business and without causing excessive waiting time for the patient. A feature of the invention is that, at the time the appointment is scheduled, real-time data, historical data including future scheduled appointments, and the facility layout are interacted in real-time to provide an appointment either automatically or in interactive mode to an employee.

Another feature of the invention is that a processor in a central location of the medical facility or business includes a plurality of intelligent terminals and displays located in each space where employees interact with the management system, with patients, and with the finance, supply and maintenance sections of the medical facility or business in order to provide each of these sections with information regarding status, with directions, and with information relevant to their decision-making authorities.

As a further feature of the invention, these same terminals may also be used to program the same processor with all costs of operating the medical facility or business such as overhead, labor, inventories, medication, equipment, costs of accessing communications links, and program the same processor with the layout of the facility which houses the medical facility or business, and with health care plans and procedures. These inputs are provided in a combination of manual, semi-automatic and fully automatic means.

An even further object of the invention is to provide a dynamic, interactive, fully automatic real-time management system coupled with a clinic building design which specifically takes advantage of the management system's flow control aspects of patients and employees. A feature of the invention is that a clinic building is modular in design. An advantage of the invention is that testing and diagnosis functions can be easily expanded, and minimal space is used for the clinic building's layout. Another advantage is that these aspects in combination with the management system result in a highly efficient health care clinic. A plurality of such clinics of the same design may be interconnected through communications links to provide a health care clinic network distributed throughout a country. Profit and loss statements for owners, and patient and employee data for organizations outside the clinics can be obtained for a plurality of such clinics.

Overview

In accordance with one aspect of the invention, there is provided a fully automatic clinic with a plurality of functions, managed by a dynamic, interactive, fully automatic real-time management system. Patient and employee flow, information flow, appointment scheduling, invoicing and maintenance are all managed automatically. The patient flows through visiting a nurse, testing, sending samples into a lab, diagnosing, visiting a pharmacy and scheduling appointments, while a management system controls the location and flow of all patients and employees, occupancy of rooms in the building, samples in the lab, information, and alerts and invoices insurers before the patient leaves the clinic. All patient historical information is also tracked automatically.

The management system of the clinic includes a processor which receives inputs from outside sources such as patients' doctors and insurers, employers, hospitals, and also receives inputs from within the clinic through real-time sensors from patients, test equipment, laboratory equipment, and employees all affecting the operations of the clinic. A monitoring memory is provided for the processor to store data related to the real-time input, as well as data related to inputs for fixed parameters. Interactive terminals are also provided, allowing the employees of the clinic to interact with the management system. The processor then automatically in real-time generates outputs which manage all aspects of the clinic from instructing patients and employees, to room assignments, to matching historical records with patients, to verifying insurance and invoicing and to appointment scheduling.

The boundaries of the management system extend beyond the clinic. The clinic is tied in to doctors and hospitals which can view patient test/diagnosis information on-line, or refer and provide historical patient records, to insurers who can automatically sign up their customers and have insurance verification and invoicing automatically performed, to employers and government. All these parties will have their patient transactions and historical records automatically managed by the automatic clinic. Patients can call in with questions and be referred in real-time to doctors if needed. Employers can provide employee information for automatic appointment scheduling of tests for pre-employment drugs screens, travel immunizations, etc. Patient status and historical aspects can be made available electronically and immediately to anyone hooked into the management system.

The clinics are also interconnected to form a network. Patients and all other organizations can be served independent of location on a local, national or international level. The network of clinics comprises one large network for these patients and other organizations as the management system efficiently manages how health care is provided to patients. Each clinic building has a modular construction allowing for varying number of diagnosis and test rooms in a single clinic. The management system's performance is not influenced by the size of the clinic.

The owner of the clinic through a special access code can obtain a profit and loss statement and many other variable costs relating to the business. The management system is programmed with all costs of operating the clinic such as overhead, labor, medication, costs of accessing networks, satellites and telephone lines, and equipment as the clinic operates. As patients flow through the system all operations are tracked, time is tracked, and invoicing takes place automatically. Based on this, an owner using the access code can obtain a profit and loss statement on a daily, weekly or monthly basis.

The Effect on Current Practices

Due to its dynamic, interactive, fully automatic real-time nature, the management system for a medical facility either alone or coupled with the clinic building is anticipated to have a profound effect on how medical facilities are managed. It affects management, employees, patients, and any outside organizations that are tied into the management system.

As the management system operates, it manages and controls the flow of patients, employees, historical and financial information, time spent in the health care system, and the manner in which costs are generated in a medical facility. Managing and controlling these aspects raises accountability and furthermore limits costs by limiting unnecessary tests, treatments, and procedures and liabilities associated with today's health care system. It unravels the administrative mess, and overhead costs accompanied with billing and invoicing and payment methods.

As the management system operates, it increases the efficiency of the medical facility or business it manages, it lowers costs and controls how costs are generated, it does not get tired, it makes decisions automatically and accurately with perfect repeatability, it does not make mistakes, it does not become stressed, it reduces stress for employees by performing mundane tasks automatically, it starts patients' appointments on time and finishes on time, and it does not let paperwork interfere with patients and employees. It is impossible to be overloaded; it will not schedule more patients than it can handle within the given structure and configuration of the medical facility or business it is managing.

As it performs many of these tasks, patients spend less time in the system and have their understanding of what is happening to them increased. Employees have their capabilities increased in doing their job. It increases understanding on the part of the patient, health care professional and other employees of the medical facility or business in dealing with the patient's health, and measuring the success of health care for the patient. In other words, it increases health care employees' level of intelligence in delivering health care to the patient.

Range of Applications

This management system makes available in real-time information vital to the decision-making process, information never before available. The management system also uses this information automatically to make decisions. The management system also provides a means by which any analysis can be made or any questions answered about the interaction of related events and their effect. The level of control attained by this invention cannot be approached by existing management methods. The mastery of operations achieved will provide managers with more dynamic solutions to problems than ever before possible, will do so immediately, and will have profound effects on the structure and function of health care organizations. The system replaces intuitive judgement with real-world solutions that can be acted upon at once in any management environment. Many of these solutions are implemented automatically by the management system as it functions.

The quality and detail of information created by this invention eliminates many of the data-gathering and analytical functions performed by management personnel. It causes irrevocable changes in the kind of skills needed to achieve management goals.

The present invention has particular application to the medical industry. Besides clinics, examples of medical facilities in which the present invention applies are retirement and convalescent homes, rehabilitation centers, employer health centers in factories and office buildings, school clinics, sports facilities, field hospitals, and laboratories and testing centers. Furthermore, besides the medical industry, aspects of this invention apply to the managing of any business in the manufacturing, transportation, service and chemical process industries.

The dynamic real-time interactive management system for the management and operation of a facility and management of a plurality of persons relative to the facility includes a master processor for continuously and automatically receiving a plurality of sensed real-time inputs related to a facility and a plurality of persons relative to the facility; a memory, linked to the master processor, for storing sensed values of the real-time inputs and for storing a plurality of programs for defining relationships between certain of the sensed values of the real-time inputs; and a display connected to the master processor, the display for producing a humanly perceivable signal. The master processor is programmed to continuously and automatically determine in real-time, based on the real-time inputs, a plurality of unknown values related to conditions of the facility and the plurality of persons by individually selecting the unknown values to be determined automatically; to continuously and automatically determine in real-time interactions and relationships between the real-time inputs using the plurality of stored programs; to continuously and automatically produce an interaction indication result; to continuously and automatically produce a condition output which is indicative of the relationship between the sensed values and the interaction indication result; and to automatically transmit the condition output to the display.

The system may also include a terminal connected to the master processor for selecting a desired condition output to be transmitted to the display. In the preferred embodiment, the facility to be managed is a medical facility for treatment of patients and the plurality of persons includes patients and facility employees. The movement of patients and facility employees is monitored by a plurality of I.D. card readers that communicate with the master processor. The I.D. card readers sense I.D. card codes and transmit the sensed I.D. card codes to the master processor as sensed real-time inputs.

The terminal is also used for inputting management information into the master processor so that the master processor can interact the management information with the sensed values of the real-time inputs.

A personal computer may be connected to the master processor for transmitting a plurality of manual inputs to the master processor. The plurality of manual inputs and the condition output are stored in the memory as historical aspects and the master processor selectively interacts the historical aspects with the real-time inputs.

The real-time inputs include sensed I.D. card codes, sensed selected test information, sensed test result information, final diagnosis information, prescription confirmation, insurance verification, standardized testing program information, health maintenance program information, patient appointment information, and requests for patient data exchange.

The manual inputs include patient historical aspects, equipment maintenance information, employee schedules and rosters, inventory information, costs and facility characteristics information.

The condition output includes patient data and history information, an employee instruction, an insurer invoice, an appointment schedule, an employee duty roster, a maintenance schedule, an inventory requirement, a visit summary, an insurer approval notification, a patient referral, and a profit and loss statement for the facility.

The method of dynamic real-time interactive management and operation of a facility and a plurality of persons related to the facility includes the steps of continuously and automatically receiving, in a master processor, a plurality of sensed real-time inputs related to a facility and a plurality of persons relative to the facility; storing sensed values of the real-time inputs in a memory linked to the master processor; based on the real-time inputs, continuously and automatically determining in real-time a plurality of unknown values related to conditions of the facility and the plurality of persons by individually selecting the unknown values to be determined automatically; continuously and automatically determining in real-time interactions and relationships between the real-time inputs using a plurality of programs stored in the memory; continuously and automatically producing an interaction indication result; continuously and automatically producing a condition output which is indicative of the relationships between the sensed values and the interaction indication result; automatically transmitting the condition output to a display connected to the master processor; and producing a humanly perceivable signal in the display.

BRIEF DESCRIPTION OF THE DRAWINGS

The nature and other objects and advantages of the present invention will become more readily apparent from the detailed description that follows.

In the Drawings.

DETAILED DESCRIPTION OF THE PREFERRED EMBODIMENTS

Figure 1:
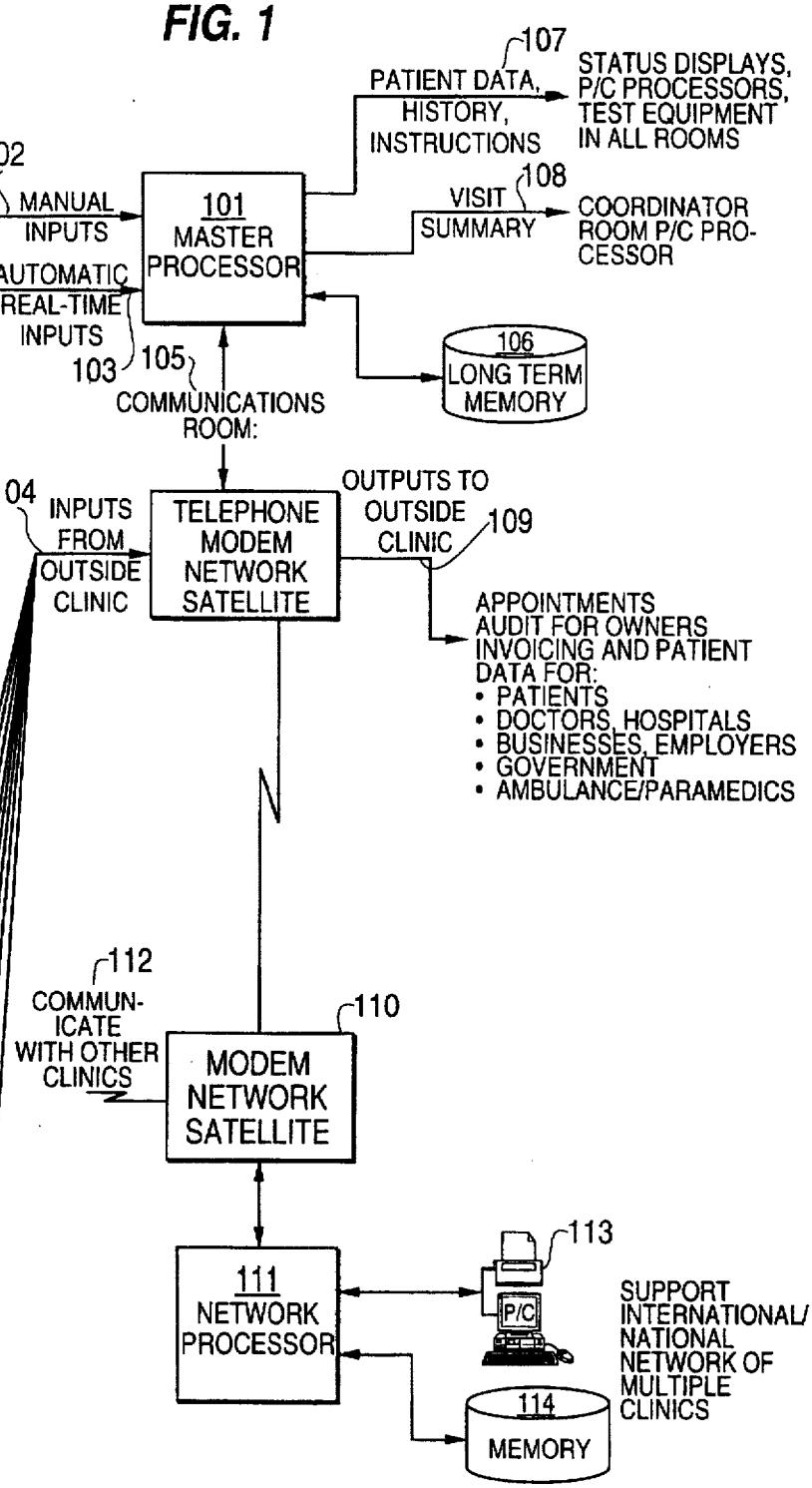
FIG. 1 is a block diagram showing the inputs and outputs for a master processor at a clinic, as well as the link between the master processor and other master processors at other clinics.

The present invention will now be described with particular reference to its applications in the medical industry, specifically with reference to hospitals and clinics. However, it will be understood that the principles of the invention are also applicable to the control and management of organizations other than hospitals, clinics and medical facilities in general.

The dynamic, interactive, automatic management system is implemented within a clinic. The flow of patients, patient information, and clinic employees are all managed automatically in real-time, most preferably through a centrally located processor, herein referred to as a master processor.

The master processor receives inputs from outside organizations, from patients, employees, and testing equipment and electronics inside the clinic, and provides outputs that manage the clinic operations and patient and information flow throughout the clinic. The outputs can be, for example, automatic real-time decisions, instructions to patients and employees, invoicing, or patient information sent to outside organizations, all as part of managing the operations in the clinic electronically.

Preferably, costs and financial performance are also tracked real-time and can be reported on demand.

Information regarding the layout of the building itself, color schemes, and the size of the clinic also are part of the management system and are stored as historical aspects. The clinic is modular in design in that its size can be easily adapted to the demands of the geographical area it serves. This makes the basic design independent of location. It can be adapted to any part of the world.

In all subsequent descriptions the flow of patients through a basic clinic design will be used to illustrate how the dynamic, interactive, fully automatic real-time management system is implemented and how it functions in its aspects pertaining to a medical clinic.

The basic clinic design preferably contains the following rooms: a communications room and a coordinator room. The communications room takes care of interfacing the clinic to the outside world for making appointments, transferal of patient data, contacting insurers, etc. The coordinator room is the starting point for the patient's flow through the clinic. All progress is tracked in the coordinator room for patients and employees in the clinic. Insurer invoicing and billing functions are also performed here. Other rooms are diagnostic rooms for interviewing the patient, ordering tests and diagnosing the ailment; test rooms for taking a variety of tests; along with a laboratory where a variety of samples can be analyzed; a pharmacy for when prescriptions are prescribed during diagnosis; and an In/Out room is provided for diagnosis of patients who walk into the clinic without appointments.

A basic clinic should have one Communications and coordinator room, several diagnostic, In/Out, and test rooms, a laboratory and a pharmacy.

The flow of a patient through the clinic is as follows: In the communications room, an appointment is made and the patient is registered with a receptionist. On the day of the appointment, once the patient arrives at the clinic, the patient flows from a coordinator person in the coordinator room to a diagnostic nurse in a diagnostic room where tests are decided upon. The patient then flows through the test room where all the tests are performed with a technician, and then back to the same diagnostic nurse for test review. Finally the patient flows to the pharmacy for pick-up of medication from a pharmacist, and back to the coordinator room where an invoice and a next appointment are prepared with the coordinator.

An In/Out room is provided for patients who walk into the clinic without an appointment. The In/Out room is similar to a diagnostic room with a diagnostic nurse where patients can be questioned and examined without interfering with the flow of patients through the diagnostic and test rooms.

I.D. card readers are used throughout the clinics for patients and employees. Anytime a patient and/or employee is present in a room, that patient's and/or employee's I.D. card must be inserted at the I.D. card reader. This ensures that the location of each patient and employee is known.

1. Overview of Inputs and Outputs to Master Processor

Reference is made to FIG. 1 showing inputs and outputs to Master Processor 101;

FIG. 1 is a block diagram showing the inputs and outputs for a Master Processor and the components at a clinic as well as a link between this Master Processor and Master Processors at other clinics. From inside the clinic building, Master Processor 101 has multiple manual inputs 102, and multiple automatic real-time inputs 103.

Automatic Inputs The automatic real-time inputs 103 include I.D. card codes from patients and employees at each room in the clinic, inputs from diagnostic rooms regarding tests that are being selected for a patient, inputs from test rooms and the laboratory regarding results of tests performed on the patient, further inputs from diagnostic rooms regarding final diagnosis after test results have been evaluated, and prescription confirmation from the pharmacy for a prescription that was filled for a patient.

Clinic owners via an I.D. card code may provide inputs to Master Processor 101 requesting a profit and loss statement for the clinic.

Further automatic real-time inputs 104 can originate outside the clinic via, for example, a modem, a network, or a satellite, and pass through a communications room 105 into the Master Processor 101. Owners or other appropriate persons can also obtain profit and loss statements outside the clinic. Further inputs include inputs from insurers regarding verification of insurance for a patient, inputs about standardized testing programs and health maintenance programs in which a patient participates, inputs to make the appointments for a patient, and inputs requesting exchange of patient data between clinic and outside organizations such as doctors offices, hospitals, employers, government, businesses and other clinics. Other automatic real-time inputs may be provided as necessary or desired.

These outside organizations can also reach the clinic manually by telephone to perform all these functions. Patients may call up to ask a nurse a question, or to make an appointment. Referral services may be set up through the clinic. In these cases, the information is preferably entered manually at communications room 105.

Manual Inputs

The other manual inputs 102 are regarding historical aspects of the clinic, such as equipment maintenance, employee schedules and rosters, and initial inventory, operational, labor, and overhead costs. This information is preferably stored in a Long Term Memory 106. Clinic characteristics such as the number of test rooms and diagnostic rooms are also kept as clinic aspects in the Long Term Memory 106. Prior to start-up of the clinic, the Long Term Memory 106 may be initialized with this information.

All data regarding clinic configuration is advantageously treated as historical aspects by the Master Processor 101 as it automatically performs real-time interaction with the inputs and outputs throughout the clinic.

The purpose of managing these aspects is to indicate the availability of employees, equipment, and general inventory requirements. A duty roster can be generated for the employees, a maintenance schedule for equipment, and inventory requirements for items used and prescribed to patients that visit the clinic.

The objective is to meet patient service levels with a planned capacity of resources in the clinic. Fluctuations in demand may then result in different projected resource utilizations which in turn result in changes in staffing requirements and projected maintenance and inventory reorder schedules. Other manual inputs may be provided as necessary or desired.

The Master Processor 101 is programmed to use all these inputs and automatically provide the outputs that will manage the operations at the clinic. The Master Processor 101 provides patient data and history, and instructions 107 for employees to rooms, preferably to all rooms, in the clinic. This information is advantageously displayed on wall displays and is also provided to a P/C processor and test equipment in each room. The P/C processor in each room allows the employees to communicate with the Master Processor 101. The Master Processor 101 will print a visit summary 108 at the end of each patient visit. The visit summary contains a brief description for the patient on what was performed and concluded, next appointment and a copy of the invoice.

The Master Processor 101 will automatically perform other functions, for example, invoice the insurers, schedule appointments, and provide financial performance of the clinic, and provide outputs 109, representative of these functions, to those linked to the clinic via the communications room 105. The Master Processor 101 will also forward a patient to the paramedics, refer a patient to a doctor or hospital for specialized care, notify a patient's insurer for approval of services, and potentially notify other interested businesses such as employers, and government.

In many instances the Master Processor 101 will interact in real-time one or more inputs 102, 103 and 104 with related historical aspects from the Long Term Memory 106 to provide any of these outputs 107, 108, 109.

The clinic does not have to be a stand-alone entity. Patients can be served independent of location on a local, national or international level through a network of these clinics. Thus, a plurality of Master Processors 101 from multiple clinics can communicate with each other, for example, via modem, network, and satellite 110 from the communications room 105 at each clinic into communications facilities of a network. A network processor 111 may be an existing telecommunications network, through which the Master Processors at other clinics 112 can communicate.

This is done, for example, for purposes of transferring patient data, or possibly supporting government studies, or providing services where medical professionals can subscribe to the historical aspects regarding information and frequency of ailments, remedies, diagnosis, and demographics. Secondly, owners will need to be able to manage multiple clinics and obtain financial performance without having to physically travel to each and every clinic. Owners may have facilities with their own remote processors 113 and remote memory 114 to perform these tasks, connected to the clinic Master Processors via a network processor 111. The remote processor 113 could be a P/C, with printer and other conventional peripherals. Thus, an international and/or national network of multiple clinics may be supported.

2. Communications Room

The communications room 105 allows the Master Processor 101 to automatically manage patient and clinic aspects between the clinic and the organizations outside the clinic such as insurers and government, hospitals and doctor's offices, businesses, and other clinics. This is on a local, state, national, or international scale. As the information is obtained or provided from or to these outside organizations, resources in the communications room 105 ensure this information is stored in the Long Term Memory 106 for use by the Master Processor 101.

All patient registration takes place in the communications room 105. Patient registration involves entering the patient's information into the Long Term Memory 106, preferably when the patient first visits the clinic. Registration also generally involves verification of insurance coverage. Appointment scheduling can also be performed.

Another function of the communications room 105 is to process walk-in patients—patients that enter the clinic without an appointment.

Figure 2:
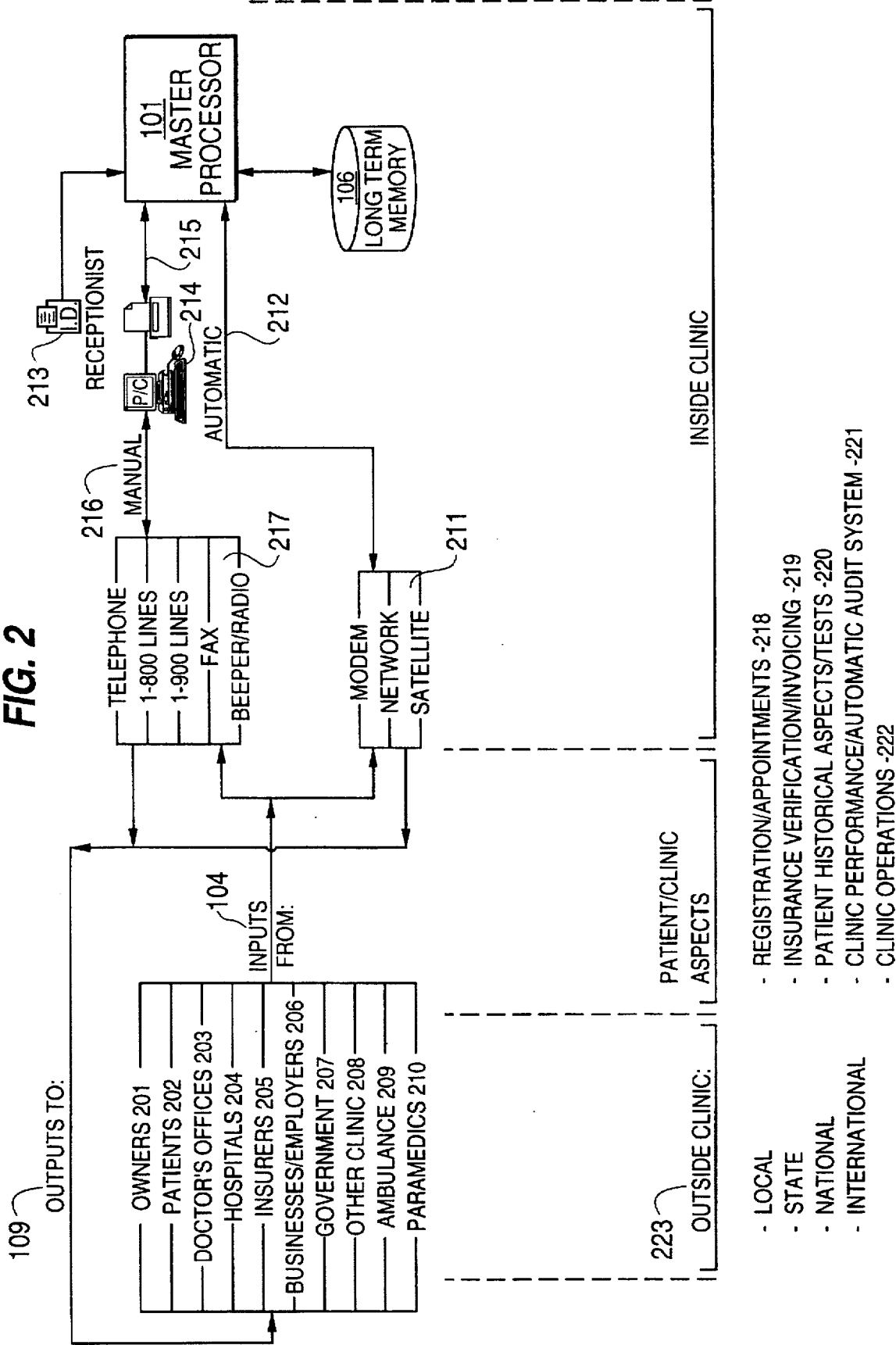
FIG. 2 is a block diagram showing the inputs and outputs of the communications room.

Reference is made to FIG. 2, showing Inputs and Outputs to the Communications Room. Inputs 104 and outputs 109 to Master Processor 101 from outside the clinic building preferably come through the communications room 105. These inputs 104 and outputs 109 can be entered manually by the receptionist or are handled automatically in real-time by the Master Processor 101. These inputs 104 and outputs 109 are used by the Master Processor 101 to obtain information from a plurality of sources or destination organizations 201–210 outside the clinic about the patient via an input line 104, and to provide known patient aspects to organizations outside the clinic 201–210 as outputs via an output line 109.

Inputs and outputs outside the clinic can have the following sources and destinations 201–210:
OWNERS-201
PATIENTS-202
DOCTORS' OFFICES-203
HOSPITALS-204
INSURERS-205
BUSINESSES/EMPLOYERS-206
GOVERNMENT-207
OTHER CLINIC-208
AMBULANCE-209
PARAMEDICS-210

Other inputs and outputs may be provided as necessary or desired.

The Master Processor 101 automatically in real-time manages patient processing, and automatically in real-time manages a transmission of patient and clinic aspects between the clinic and inputs 104 and outputs 109 via facsimile, modem, network, or satellite 211. An automatic line 212 interconnects the Master Processor 101 with the modem, network or satellite 211. The Master Processor 101 automatically in real-time interacts with the Long Term Memory 106 to obtain or provide the patient and clinic aspects.

The patient and clinic aspects may also be manually input or output by a receptionist 213. In this case, the Master Processor 101 communicates with the receptionist via P/C processor 214 in response to inputs 104 and for providing outputs 109. The inputs 104 and outputs 109 reach the receptionist via communication links 217, for example, 1-800 and 1-900 telephone lines, facsimiles, beepers, and radios. This information is then manually transferred at 216 from these links by the receptionist using the P/C processor 214. The P/C processor 214 then provides this information to the Long Term Memory 106 via a memory link 215 for use by Master Processor 101.

This design is not limited by the number of different aspects that can be automatically managed. Many of the aspects necessary to automatically manage the clinic are described in the following categories:
REGISTRATION/APPOINTMENTS-218
INSURANCE VERIFICATION/INVOICING-219
PATIENT HISTORICAL ASPECTS/TESTS-220
CLINIC PERFORMANCE/AUTOMATIC AUDIT SYSTEM-221
CLINIC OPERATIONS-222

These are described in further detail in the following section along with functions the Master Processor 101 performs to automatically in real-time manage patient processing and to automatically in real-time manage all patient and clinic aspects.

Since multiple clinics may be networked with each other, many of the organizations 201-210 will be connected to a network of clinics. Therefore, these patient/clinic aspects can originate from outside the clinic on a local, state, national, or international level 223.

2.1 Appointments/Registration 218 and Sample Programs of Real-Time Interaction

Reference is made to FIG. 2, Inputs and Outputs to Communications Room. Appointments can be made manually or automatically.

Manual Registration and Scheduling of an Appointment

A patient 202, a doctor's office 203, hospital 204, insurer 205, business/employer 206, or government 207 representing the patient calls the clinic by a phone or other communication link 217. The receptionist 213 will select an appointment function at the P/C processor 214, and the Master Processor 101 will automatically provide an available time slot. The following automatic real-time interaction takes place with the Master Processor 101, in the preferred embodiment.

Figure 3:
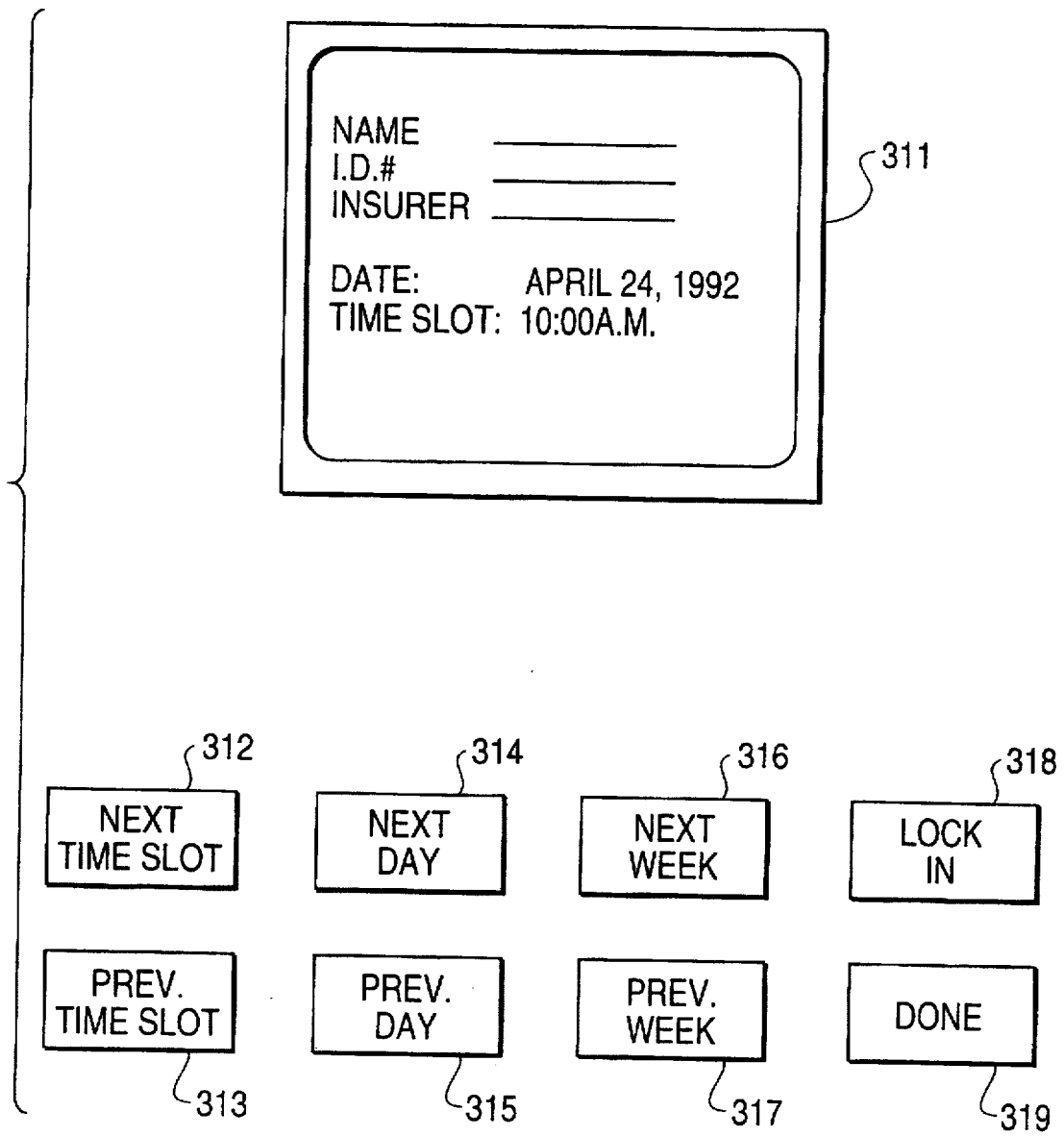
FIG. 3 shows the appointment function keys for the coordinator and receptionist.

The receptionist 213 answers the phone and hits an "Appointment" function key on a keyboard at the P/C 214. If the patient just walked into the clinic, the receptionist 213 helps the patient fill out a questionnaire. The Master Processor 101 automatically obtains an appointment calendar from the Long Term Memory 106 and automatically via the memory link 215 displays the appointment calendar for the clinic on a P/C 214 monitor. By default, the first available day and available time slot is shown, for example: Apr. 24, 1992, 10:00 a.m., as illustrated in FIG. 3, (Patient Appointment Scheduling Display) 311. The receptionist 213 enters the patient name. If the patient has previously visited the clinic, a Patient I.D. number and insurer information will automatically be provided by the Master Processor 101 via the memory link 215 at the P/C 214 from the Long Term Memory 106. If this is the first time the patient has visited the clinic, the patient I.D. and insurer/payment method fields displayed on P/C 214 monitor will be blank, and insurer information is preferably provided by the patient or someone representing the patient.

Reference is made to FIG. 3 for the appointment scheduling display 311 and function keys 312-319. The receptionist 213 informs the patient of the date and time slot displayed on the P/C 214 monitor as shown in FIG. 3 311. If the patient has a time conflict with this, the receptionist 213 can use the "next slot" 312, "previous slot" 313, "next day" 314, "previous day" 315, "next week" 316, or "previous week" 317 function keys to get to a date and time slot the patient prefers. Master Processor 101 will not display any dates and time slots that have already been booked full. Once a date and time slot have been agreed upon, the receptionist presses the "lock in" 318 function key and the Master Processor 101 enters the appointment into the Long Term Memory 106. The receptionist 213 exits the appointment scheduling function by selecting the "done" 319 key.

Figure 4:
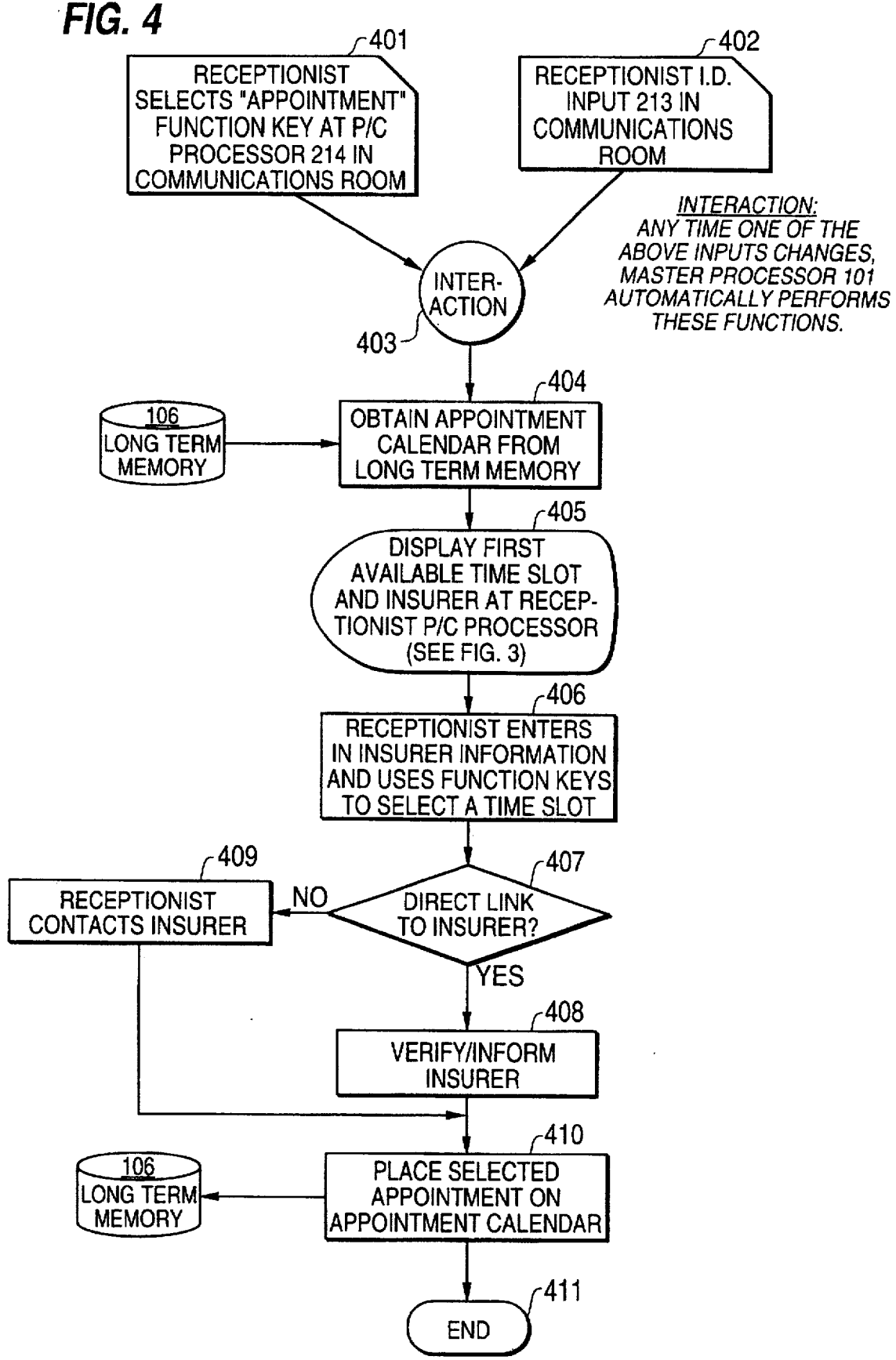
FIG. 4 shows automatic real-time interaction by the master processor for appointment scheduling and insurance verification with the receptionist in the communications room.

Sample program: Reference is made to FIG. 4, Appointment Scheduling and Insurance Verification with Receptionist. FIG. 4 shows a short-hand flow chart for one embodiment of how once the patient I.D. input is received, the Master Processor 101 automatically in real-time accomplishes the appointment scheduling and insurance verification tasks with the receptionist.

A plurality of known events 401 and 402 are, for example, an appointment key selection input from the P/C processor 214, and a receptionist I.D. input 213 from the I.D. card reader, respectively. Interaction 403 takes place between these inputs which starts a chain of events to determine the unknown: an available appointment slot.

The appointment calendar with existing booked time slots is obtained from Long Term Memory 106 at block 404 and the first available time slot is displayed in block 405 at the P/C processor for the receptionist. The receptionist selects a time slot through talking with the patient in block 406. The patient has told the receptionist which insurance carrier is to be used. If this insurer has a direct link with the clinic, the insurer is contacted automatically through modem, network or satellite 211 (see FIG. 2) as shown in blocks 407 and 408. If no direct link exists, the insurer is contacted manually by the receptionist as shown in blocks 407 and 409. Once the insurance verification approval is received, the selected appointment is placed on the calendar by updating Long Term Memory 106 in block 410. The chain of events stops at block 411.

Fully Automatic Registration/Appointment Scheduling

As shown in FIG. 2 (Communications Room), a patient 202, doctor's office 203, hospital 204, insurer 205, employer 206, or government 207 representing the patient contacts the clinic by modem, network, or satellite 211. The Master Processor 101 automatically senses the input request and responds to the input by providing a date and time slot from Long Term Memory 106 via the same communications medium 211 (modem, network, or satellite) from which the input originated from.

Figure 5:
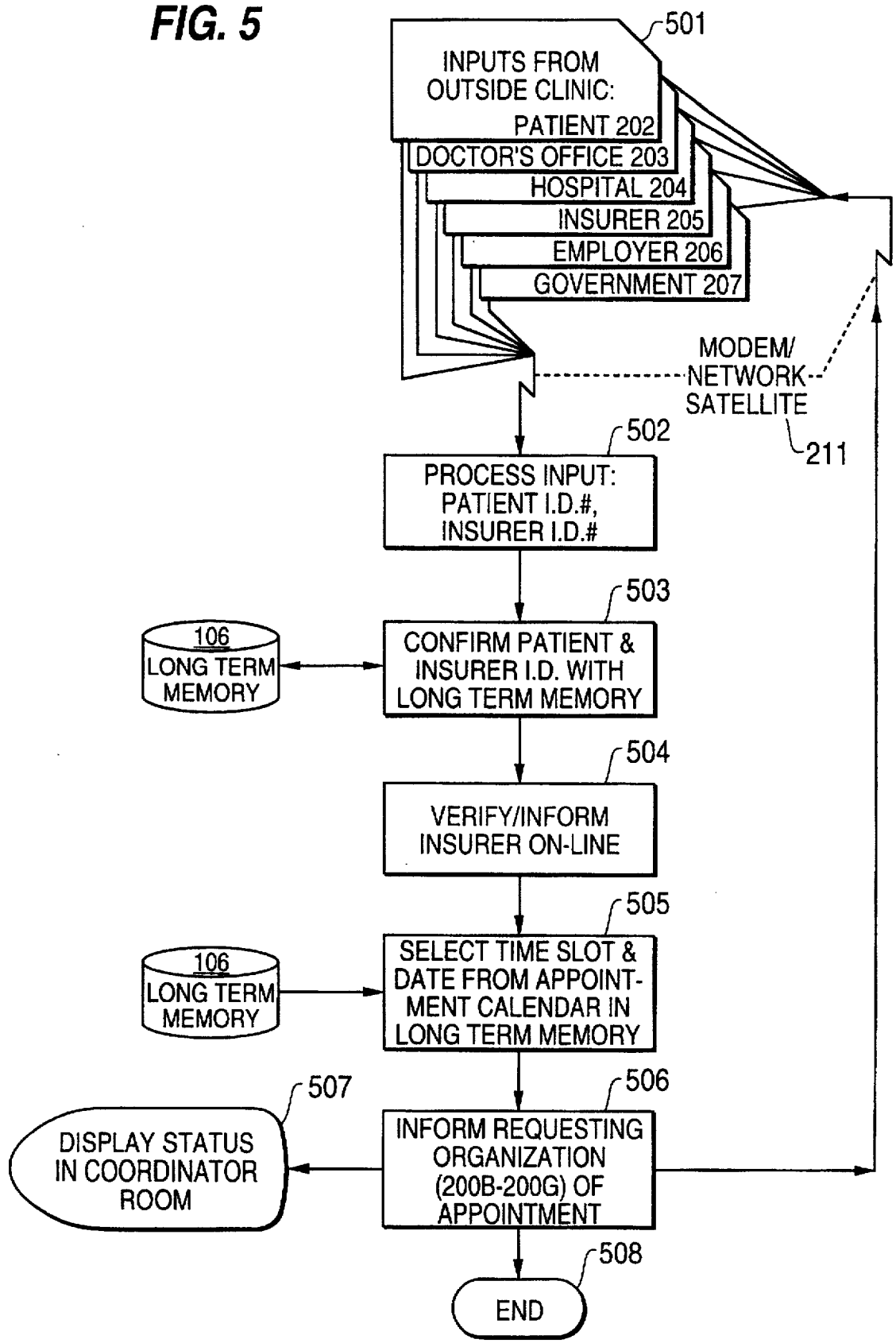
FIG. 5 shows automatic real-time interaction by the master processor for on-line appointment scheduling and insurance verification.

Sample program: Reference is made to FIG. 5, On-Line Appointment Scheduling and Insurance Verification, which shows a short-hand flow chart of how once an input from organization 202-207 is received, the Master Processor 101 automatically in real-time accomplishes the appointment scheduling tasks.

A known event indicated by block 501 is, for example, the request for an appointment from one of the organizations 202-207. This starts a chain of events to determine the unknown: an available appointment slot. Along with the request via modem, network, or satellite 211 is the patient's I.D. number and insurer information. At block 502 these inputs are processed. The received patient and insurer I.D.s are checked with the Long Term Memory 106 at block 503, and, once found, the insurer is verified on-line at block 504 via another modem, network or satellite 211. Once the approval is received from the insurer, the appointment calendar with existing booked time slots is obtained from Long Term Memory 106, and the next available time slot is selected at block 505. The requesting organization is informed of the appointment at block 506 via the same means 211 the requesting organization used to contact the clinic in the first place. At block 507 the status display in the coordinator room is also updated indicating automatic appointment scheduling is presently taking place. The chain of events now stops at block 508.

I.D. Cards

For patients joining the clinic, the Master Processor 101 will also preferably automatically assign a patient I.D. number, and print out the patient I.D. card. The I.D. card is advantageously placed in a holding bin in the coordinator room for pickup during the patient's first scheduled visit. The I.D. card will be used for automatic identification as the patient enters the clinic and will also be scanned and used to track the patient's progress and location once inside the clinic. As an alternative "I.D. card", other unique identifiers could be used, for example, a thumbprint and appropriate scanners.

2.2 Insurance Verification/Invoicing 219

Reference is made to FIG. 2, on Inputs and Outputs to Communications Room. The Master Processor 101 will contact the insurer automatically, through interacting all inputs and outputs in real-time. A decision is made and/or all necessary information is transmitted immediately without delay for the patient. The insurer will be contacted by the Master Processor 101 for the following reasons:

During Appointment Scheduling or for a Walk-In Patient

The patient data presently being obtained is also used to contact the correct insurer. Since the Master Processor 101 just automatically processed the patient data into Long Term Memory 106 for appointment scheduling, this same information is now used by Master Processor 101 to automatically contact the insurer for insurance verification. Master Processor 101 automatically accesses the insurer via modem, network, or satellite 211. FIGS. 4 and 5 show how insurance verification in this situation is automatically accomplished by the Master Processor 101 as part of appointment scheduling.

Patient Enters the Clinic with an Appointment

The patient I.D. card input is taken by the Master Processor 101 at the coordinator check-in position. Automatically, the Master Processor 101 searches Long Term Memory 106 for the insurer data for the patient I.D. Next, the Master Processor 101 automatically accesses the insurer for verification via modem, network, or satellite 211.

At the End of a Visit to the Clinic

As the patient readies to proceed to the coordinator check-out position, the patient I.D. card is extracted from its current location. Automatically, the Master Processor 101 searches the Long Term Memory 106 for the insurer data for the patient I.D. Next, the Master Processor 101 automatically contacts the insurer for invoicing via modem, network, or satellite 211.

If no on-line link exists with the insurer, the insurer is contacted by telephone by the receptionist 213. Instructions in this case for the receptionist 213 will be displayed on the P/C monitor 214 by Master Processor 101.

2.3 Patient Historical Data/Tests 220

Reference is made to FIG. 2, Inputs and Outputs to Communications Room. As part of the patient data obtained during appointment scheduling, other patient data may also be automatically supplied by the same automatic or manual means described under the section on "Appointments/Registration". This is described below as "Ordering Tests" for inputs and "providing Patient and Clinic Aspects to Outside Organizations" for outputs.

Ordering Tests

The patient 202, doctor's office 203, hospital 204, insurer 205, employer 206, or government 207 representing the patient can order tests. For example, an insurer may have a program with the clinic where standardized testing is done for life insurance policies. A doctor may be referring a patient to the clinic to have a set of tests performed. Employers may sign up employees for drug screening or travel-related immunizations, hospital maternity wards may sign up infants on immunization programs, etc.

The patient 202, doctor's office 203, hospital 204, insurer 205, employer 206, or government 207 representing the patient contacts the clinic by modem, network, or satellite 211. The organization 202–207 contacting the clinic provides the patient I.D. and test to be ordered. The Master Processor 101 automatically senses the input request from 211 and stores the tests 220 to be performed for the patient I.D. in Long Term Memory 106.

Providing Patient and Clinic Aspects to Outside Organizations

Patient and clinic aspects can also flow from the clinic to organizations outside the clinic 201 through 210. Examples follow:

Reporting Test Results

For those sources that registered a patient and ordered tests (202–207), upon completion of the patient's visit, the test results will be reported automatically by the Master Processor 101.

A Doctor's Office/Hospital Requesting Patient Data

A patient registered at the clinic may be visiting a specialist at a doctor's office 203 or hospital 204, and this specialist requests the patient's history from the clinic.

On-Line Diagnosis with a Specialist Located Outside the Clinic.

While the patient is at the clinic, during diagnosis, a diagnostic nurse decides to contact a doctor for an opinion, or to refer the patient to a specialist. The Master Processor 101 automatically sets up a connection between the clinic and the doctor's office via communication link 211 and transmits the patient's history and current test results for review by the doctor. A decision is reached immediately on what the patient should do next.

While the patient is in a test Room, the Master Processor 101 can set up a communications link with a doctor to automatically provide testing information as it occurs, real-time. For example, EKG information or X-ray information can be transmitted real-time. Once the patient is with the diagnostic nurse, results can be reviewed real-time with the patient, diagnostic nurse, and doctor.

Contacting Paramedics or Ambulance.

A patient walks into the clinic but needs emergency care. A diagnostic nurse selects a function on the diagnostic room P/C to order the paramedics or order an ambulance. The Master Processor 101 automatically sets up a connection between the clinic and the ambulance 209, or paramedics team 210 to provide all available patient data. Upon arrival of the paramedics, the paramedics may have decided on a hospital and the Master Processor 101 automatically transmits all available patient data to this hospital.

Patients at Other Clinics in the Clinic Network Throughout the World

While travelling, a patient may walk into a clinic in a different town. As illustrated in FIG. 1, the Master Processor at the out-of-town clinic 112 takes the I.D. inputs from the patient and automatically requests the clinic network processor 111 via modem, network, or satellite 110 to locate the patient's history and insurer information. The memory 114 at the network processor stores all patient I.D. codes and the location of the clinic and possibly doctors it usually works with. The network processor 111 automatically sets up a link between the out-of-town clinic 112 via modem, network or satellite 110 and the patient's home-town clinic communications room 105. In this same manner the patient's doctor could also be contacted.

Reference is made back to FIG. 2. The Master Processor at the out-of-town clinic is now directly connected to the patient's home-town clinic as an "Other Clinic" 208. By interacting with Long Term Memory 106, the Master Processor 101 at the patient's home-town clinic now automatically transmits the needed patient data to the out-of-town clinic where the patient is currently physically located.

Supporting Studies in the Medical Field

As when other clinics are in the clinic network sharing information, information can also be shared with organizations studying trends in the medical field. Patient demographics and test result profiles can be made available to doctor's offices 203, hospitals 204, and government 207 automatically in real-time by the Master Processor 101 for such studies.

The Master Processor 101, after receiving the input from organizations 201–210 via modem, network or satellite 211, automatically searches the Long Term Memory 106 for the information. The search is keyed on patient aspects which were transmitted by the requesting organization. Next, the Master Processor 101 transmits the data from the Long Term Memory 106 via modem, network or satellite 211 to the requesting organization.

If the request is for on-line testing data while the tests are performed, the Master Processor 101 sets up a real-time link between the requesting organization 201–210 and the testing equipment via modem, network, satellite 211.

If no on-line link exists with the requesting organization, the organization can contact the clinic by facsimile or telephone 217. The receptionist 213 can then manually enter the requests for data at P/C processor 214 and then provide the input request via the link 215 to Master Processor 101. The data can then be printed by Master Processor 101 at P/C 214, and the receptionist can then manually provide the information to the requesting organization by facsimile or telephone 217 or mail.

2.4 Clinic Performance/Automatic Audit System 221

Figure 6:
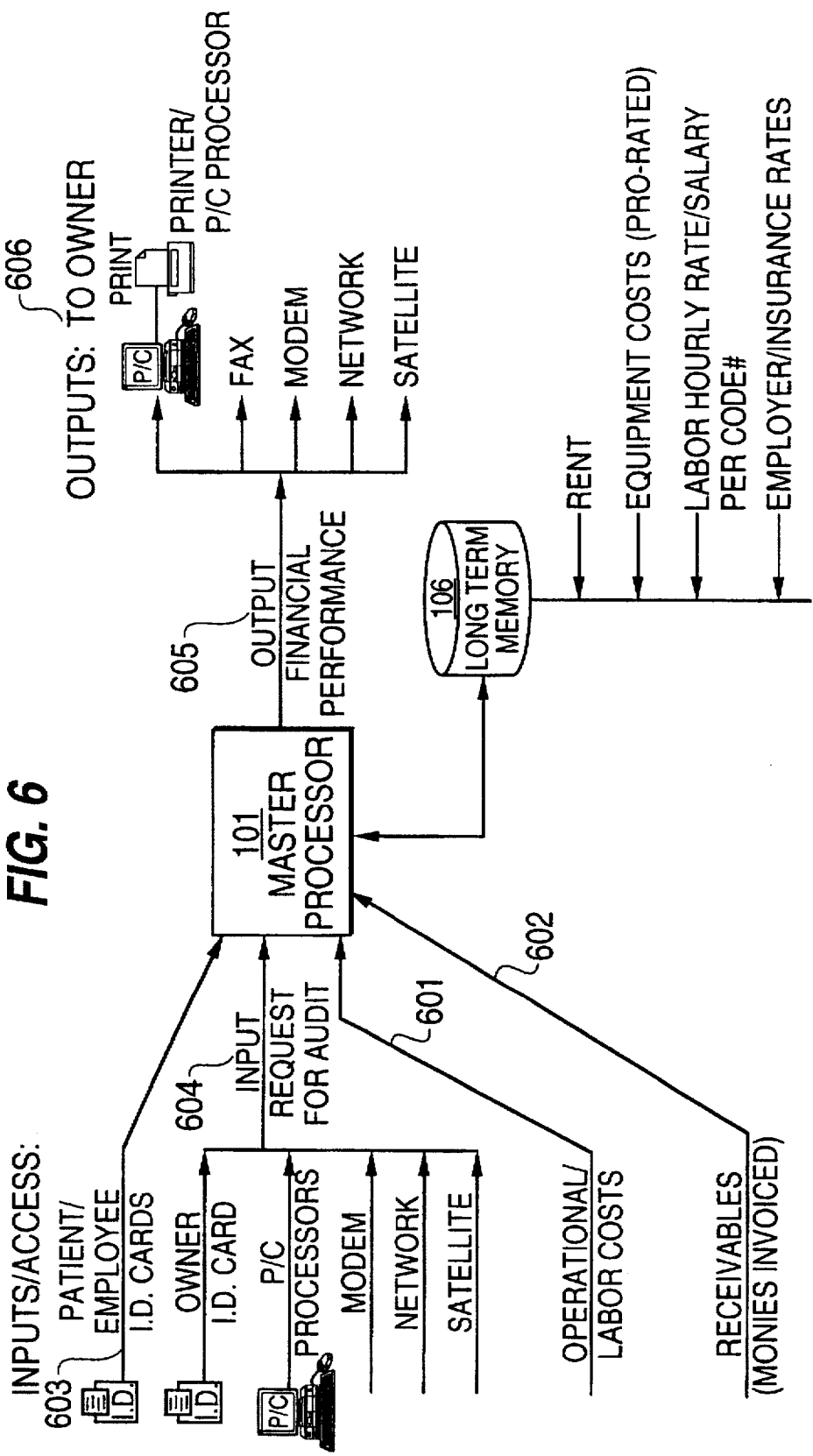
FIG. 6 is a block diagram showing the inputs and outputs for the master processor associated with the automatic audit system.

Operating expenses, and profit and loss statements can be requested by an owner 201 (shown in FIG. 2) as an audit request. This is automatically handled by the Master Processor 101 via the communications room resources. Reference is made to FIG. 6, showing the Automatic Real-Time Audit System, wherein the Master Processor 101 is programmed with all the average costs of operating the clinic (operational/labor costs 601). This includes the overhead costs, costs of medication, costs of accessing networks and phone lines for communications etc. This information is stored by Master Processor 101 in Long Term Memory 106. Information concerning rent, equipment costs, labor rates per code number, employer, and insurance rates are also stored as historical data here. Information concerning monies received after invoicing 602 are also stored in the Long Term Memory 106.

Each patient's code is recorded in the Master Processor 101 as inputs 603. When the diagnostic nurse transmits the different tests for a patient to the test room, each test is recorded in the Master Processor 101 as inputs 603. In the historical data section, which is stored information reflecting the historical knowledge of Master Processor 101, the cost of each specific test is listed. If medication is prescribed, the code number of each medication is in the historical knowledge of Master Processor 101 as is the cost. So when the patient is checking out, the type of tests and medication costs are printed out as is the cost of the diagnostic treatment.

This information is stored in Long Term Memory 106 by Master Processor 101 as historical data as they occur in real-time.

The number of employees and their code numbers are also programmed into historical data with their pay rate and any other financial data related to employees-payroll taxes, insurance, etc. The hours worked are recorded by entering the employees I.D. code (603), and removal of this I.D. code (603) when they leave for the day indicating time worked that day.

The rent or monthly cost of building and utilities, costs of equipment and payments, and balances as well as operating costs are entered into Master Processor 101. Some information is in the historical data section.

Thus, if there are daily operating and labor cost, etc., and there is the invoicing of services, tests, medication, then there is the dollar receivables for the hour, day, week, month, etc.

The Master Processor 101 keeps a running record of its overhead, cost totals, its invoicing, money owed or received and the differences to show the losses for the day, week, month, etc., or the profit being made by the clinic profit and loss statements.

A configuration, depending on what the owners want in historical data, can be obtained by the owner accessing the special owner I.D. code into the Master Processor 101, upon which the owner automatically receives the printout sheet.

To access the automatic audit system, a special I.D. card code is needed (the owner I.D. code). Shown in FIG. 6 as owner I.D. Card, this code could also be transmitted via modem, network or satellite or entered in via a P/C processor by the owner. Once the input request for an audit 604 is received, the Master Processor 101 automatically provides the operating expenses and profit and loss statement 605.

The audit 604 can be accessed anytime or from anywhere in the world, as shown in 606. The information that is variable and being entered as it occurs—tests, medication, patient cost to the clinic—is being entered as it occurs in real-time.

2.5 Clinic Operations 222

Reference is made back to FIG. 2, Communications Room. The Master Processor 101 updates the Long Term Memory 106 with information regarding the roster of all employees, equipment maintenance, inventories, and testing programs and new medical procedures. These inputs are provided manually via 1-800 and 1-900 telephone lines, facsimiles, beepers, and radios 217 or automatically via modem, network, or satellite 211 by inputs 201–210.

Prior to start-up of the clinic, the Long Term Memory 106 is preferably initialized with this information and, in operations mode, will be continuously updated through inputs 201–210 by the Master Processor 101.

The testing programs and medical procedures could be new plans the government 207 or insurers 205 are providing to clinics in the network. The government or an employer, for example, may fund a childhood immunization program to be distributed and administered through the network of clinics. This information must be received and put in place before the patients come through. Instead of doing this manually for every clinic, this information can be downloaded to every clinic. A maintenance function of the Master Processor 101 is to update the Long Term Memory 106 with these new programs and prepare the clinic employees for patients who will be covered under specific insurer care packages.

3. Coordinator, Diagnostic, Test, Lab, & Pharmacy Rooms 3.1 Clinic Input and Output Components to Master Processor 101 Inside the Clinic Reference is made to FIGS. 7 and 8, Automatic Real-Time Inputs and Outputs. These Figures describe input and output components throughout the clinic to the Master Processor 101. The Master Processor 101 uses these components to automatically in real-time manage the flow of patients and employees, and automatically in real-time manage all information pertaining to the patient. These inputs and outputs are summarized in FIGS. 7 and 8.

Figure 7:
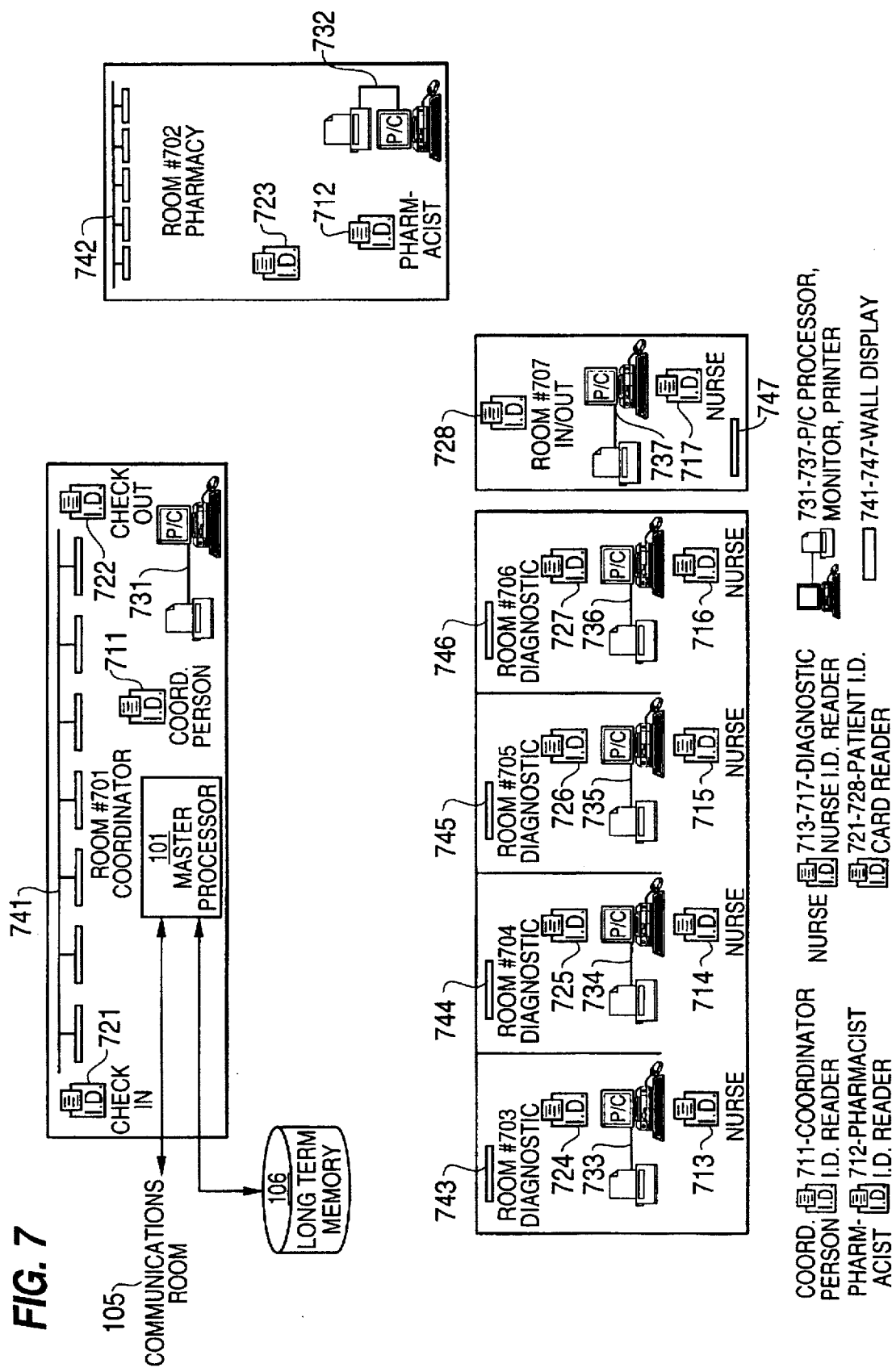
FIGS. 7 and 8 illustrate the automatic real-time inputs and outputs in the coordinator, diagnostic, in/out, test, pharmacy and laboratory rooms to and from the master processor.

In FIG. 7:

101—Master Processor which automatically in real-time manages and controls all functions throughout the clinic; 106—Long Term Memory for patient and clinic historical data; 105—Communications Room for incoming and outgoing telephone, modem, network and other communications with organizations outside the clinic.

Employees: 711—Coordinator I.D. Card Reader; 712—Pharmacist I.D. Card Reader; and 713-717—Diagnostic Nurse I.D. Card Readers, are inputs to the Master Processor 101 and are used by these employees while they are in each room. The Master Processor 101 uses these inputs to automatically track the employees. 721-728—Patient I.D. Card Readers input to the Master Processor 101 and are used by the patients while they are in each room. The Master Processor 101 uses these inputs to automatically track the patients. 731-737—P/C Processor with Monitor and Printer in each room for communication between the employees and the Master Processor 101. 741-747 Wall Displays, which are automatic outputs from the Master Processor 101 displaying messages for both the employee and patient in each room.

Figure 8:
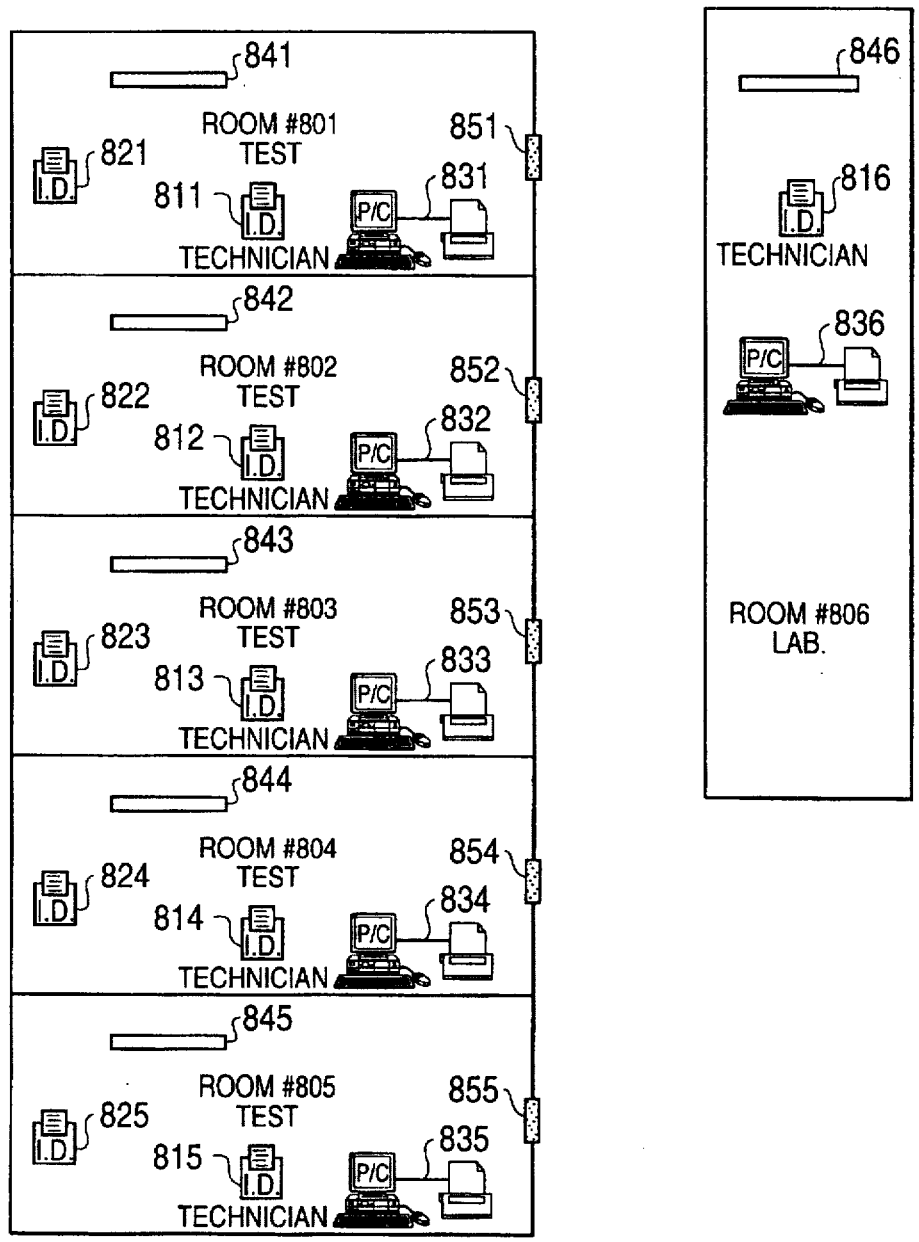

In FIG. 8:

Employees: 811-816—Test and Laboratory Technician I.D. Card Readers input to the Master Processor 101 and are used by the employees while they are in each room. The Master Processor 101 uses these inputs to automatically track the employees. 821-825—Patient I.D. Card Readers input to the Master Processor 101 and are used by the patients while they are in each test room. The Master Processor 101 uses these inputs to automatically track the patients. 831-836—P/C Processor with Monitor and Printer in each room for communication between the employees and the Master Processor 101. 841-846—Wall Displays, which are automatic outputs from Master Processor 101 displaying messages for both the employee and patient in each room. 851-855—Test Room Sample to Lab input to the Master Processor 101 for passing a sample from a test room into the laboratory.

3.2 Component to Master Processor 101 Connect Schematic

Figure 9:
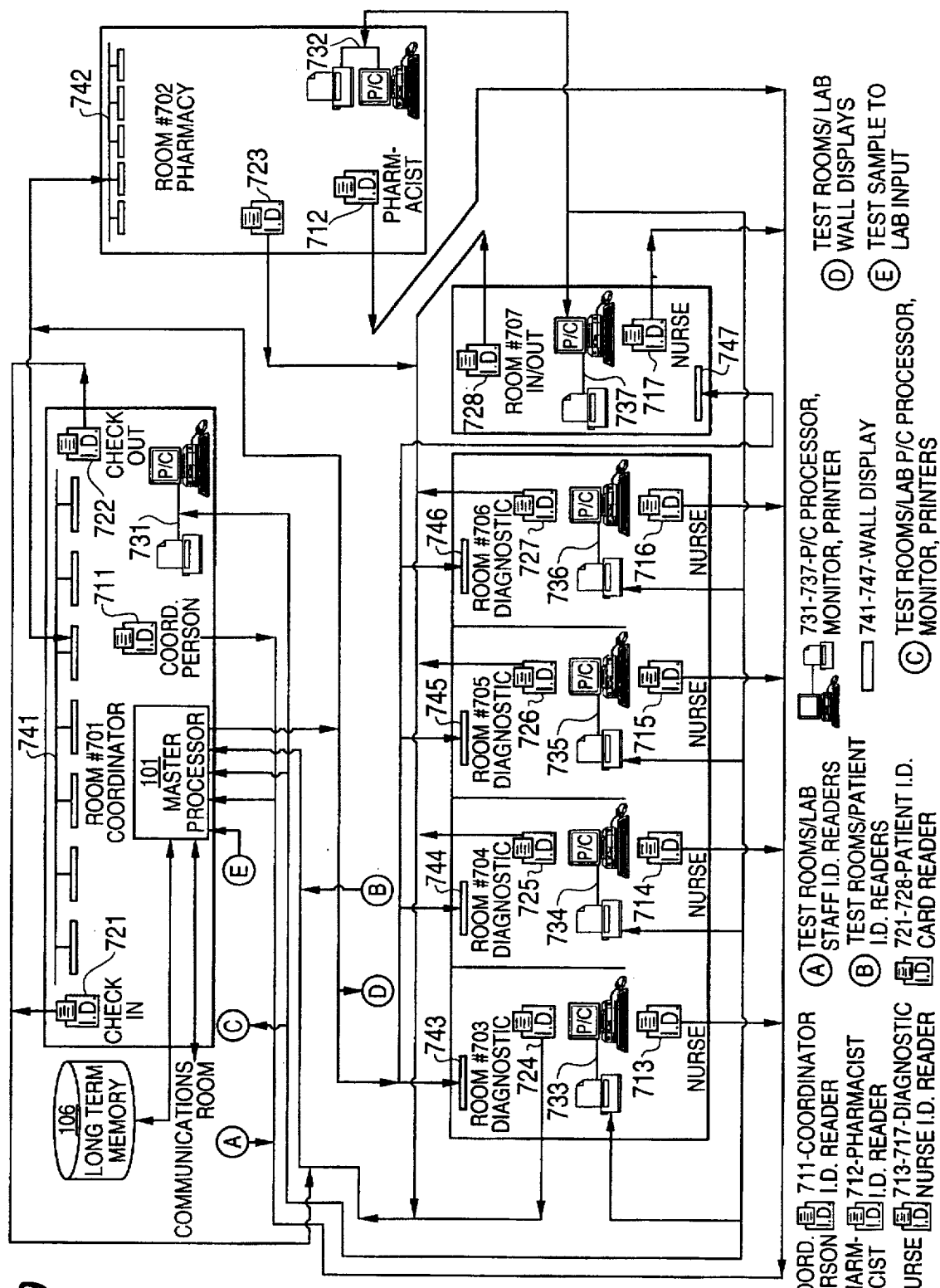
FIGS. 9 and 10 are schematic diagrams showing all components connected to the master processor. The master processor receives inputs and provides outputs automatically in real-time via these interconnections.
Figure 10:
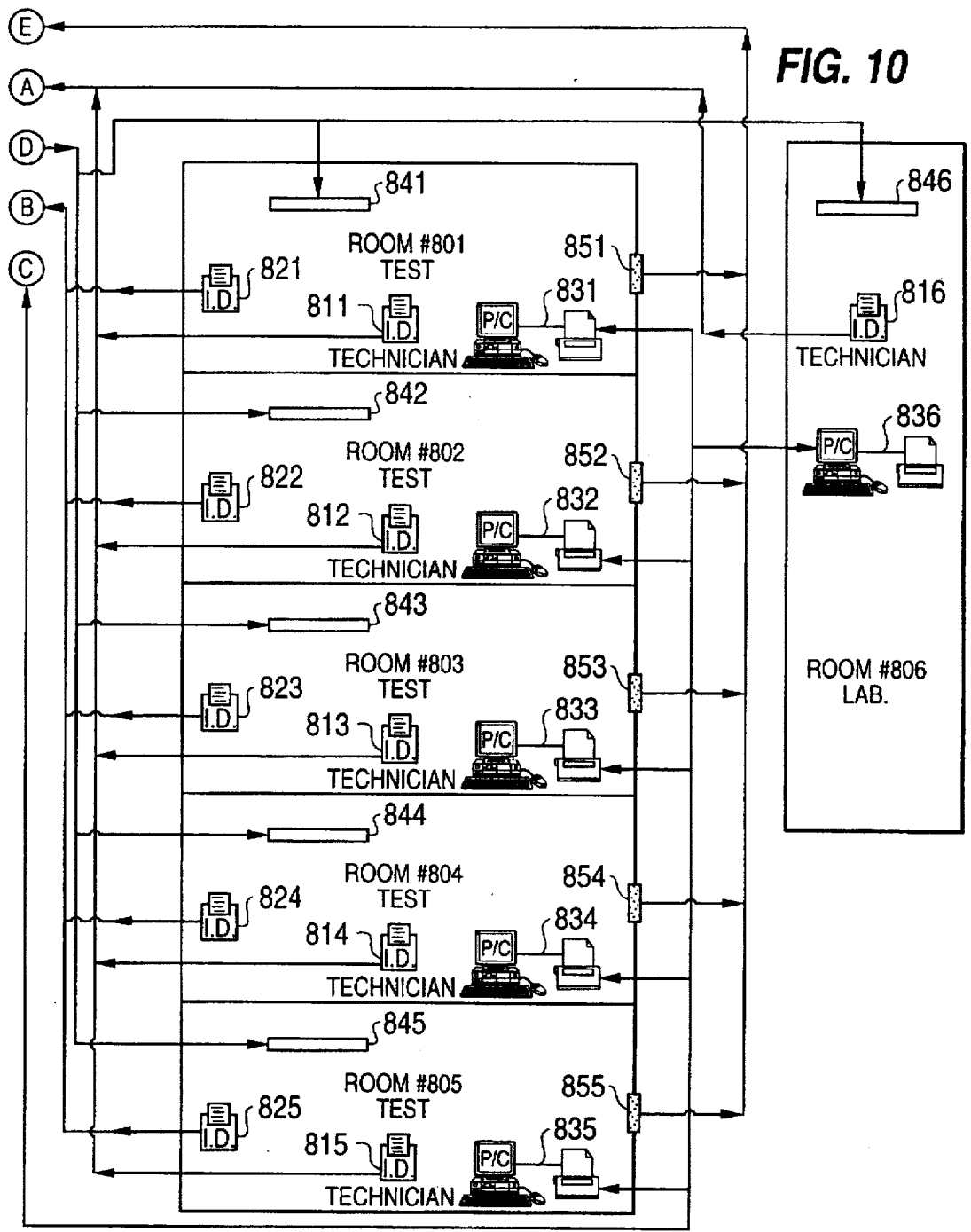

FIGS. 9 and 10, which are Component Schematics, show how the Master Processor 101 has access to all inputs and outputs from all components throughout the clinic. This enables the Master Processor 101 to interact any combination of inputs and provide outputs in real-time. FIGS. 9 and 10 merely interconnect all components described in FIGS. 7 and 8 with the Master Processor 101.

Automatic Interaction

The Master Processor 101 is continuously scanning all inputs. None of these inputs change as long as there are no patients in the system. Once the first I.D. card input is received, the process of managing patient and information flow throughout the clinic is started. The Master Processor 101 then begins automatic processing of inputs and outputs from the various components in each room, and the transferring of information between the displays, P/C processors in each room, and the Long Term Memory 106. The Master Processor 101 makes decisions through real-time interaction of inputs, outputs and historical aspects stored in Long Term Memory 106.

This results in the real-time automatic management of patients, employees, information and resources in the clinic. The purpose of the employees is to serve the customer—the patient. The minute-to-minute and day-to-day chores of managing the clinic are all performed automatically by Master Processor 101.

3.3 Patient Flow Through the Clinic

Two types of patients may enter the clinic, herein designated registered patients and walk-in patients. Registered patients are those patients who call in by phone or have an appointment scheduled before they enter the clinic.

An In/Out room is provided for patients who walk into the clinic without an appointment (walk-in patients). The In/Out room is like a diagnostic room where patients can be questioned and examined without interfering with the flow of patients through diagnostic and test rooms. If space is available an appointment may be scheduled to begin at once for a walk-in patient through a test room. A high-level flow of walk-in patients is described here.

Registered patient flow will be used throughout this invention to describe all aspects of the clinic and automatic management system in detail.

This patient flow through the clinic is described in three sections. Each section describes the same sample process of registered patient flow through the clinic. The sections differ only in that increasing amount of detail is added in each consecutive section. First, in the present section titled "3.3 Patient flow through the Clinic", the patient flow will be described as patients physically flow through the clinic from room to room. The purpose of each room will also be described here.

Second, this flow will be repeated with all inputs and outputs to the Master Processor 101 referenced in a section titled "3.4 Automatic Real-Time Management of Patient and Employee Flow".

Third, the flow will be repeated again with all information flow and some sample real-time interactions referenced for managing patient, employee, and information flow. This section is titled "3.5 Automatic Real-Time Management of Patient, Employee and Information Flow." Sample programs with real-time interaction by Master Processor 101 will also be illustrated in this section.

These three sections describe each function as a patient steps through the process of obtaining health care at the clinic. It is to be understood that multiple patients at multiple locations will be triggering the events about to be described. The configuration and size of the clinic limit how many patients and employees as well as how much information can be handled at one time by the dynamic, interactive, fully automatic real-time management system in the clinic.

3.3.1 Registered Patient Flow

Figure 11:
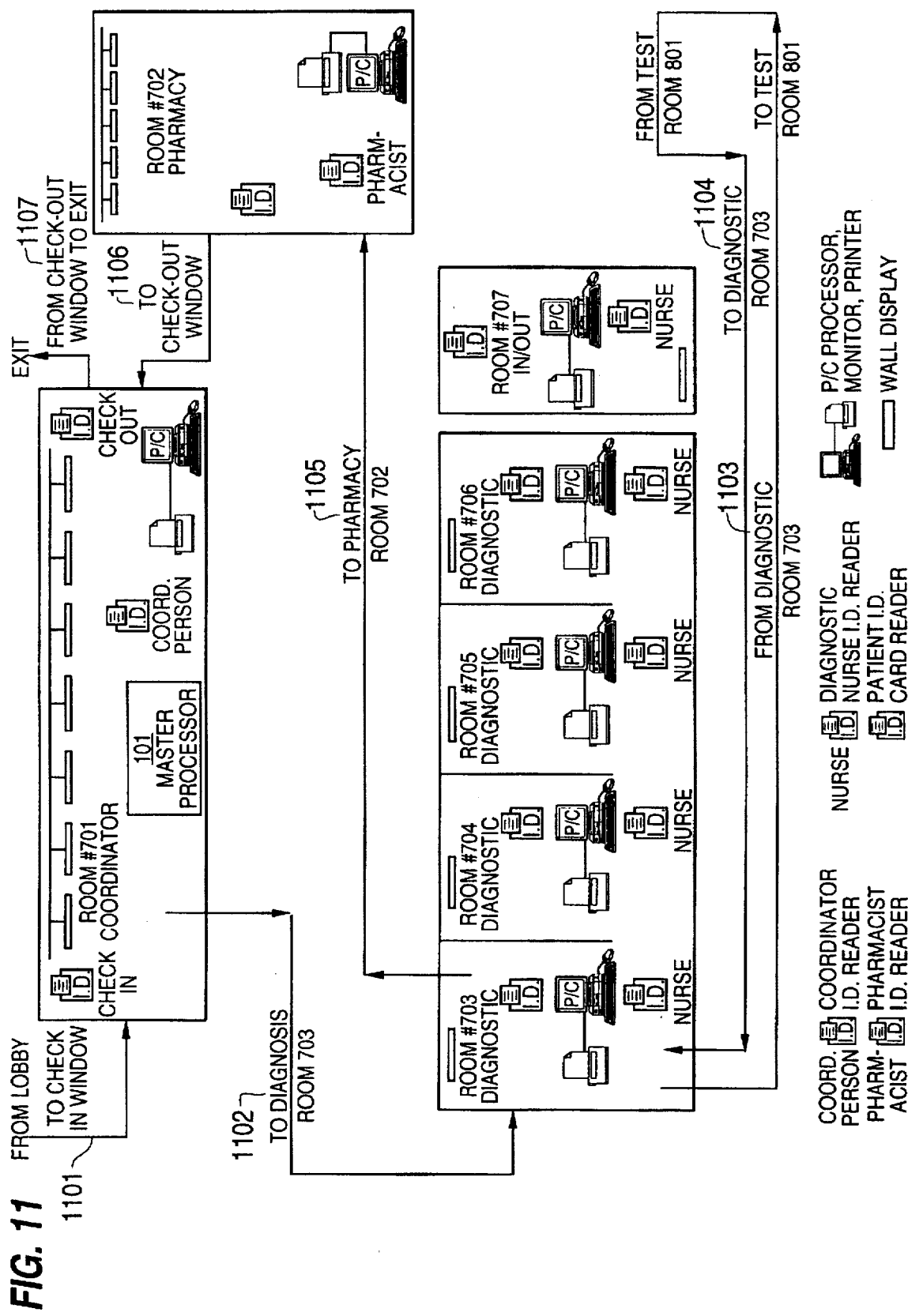
FIGS. 11 and 12 show the patient flow through the clinic for a registered patient.
Figure 12:
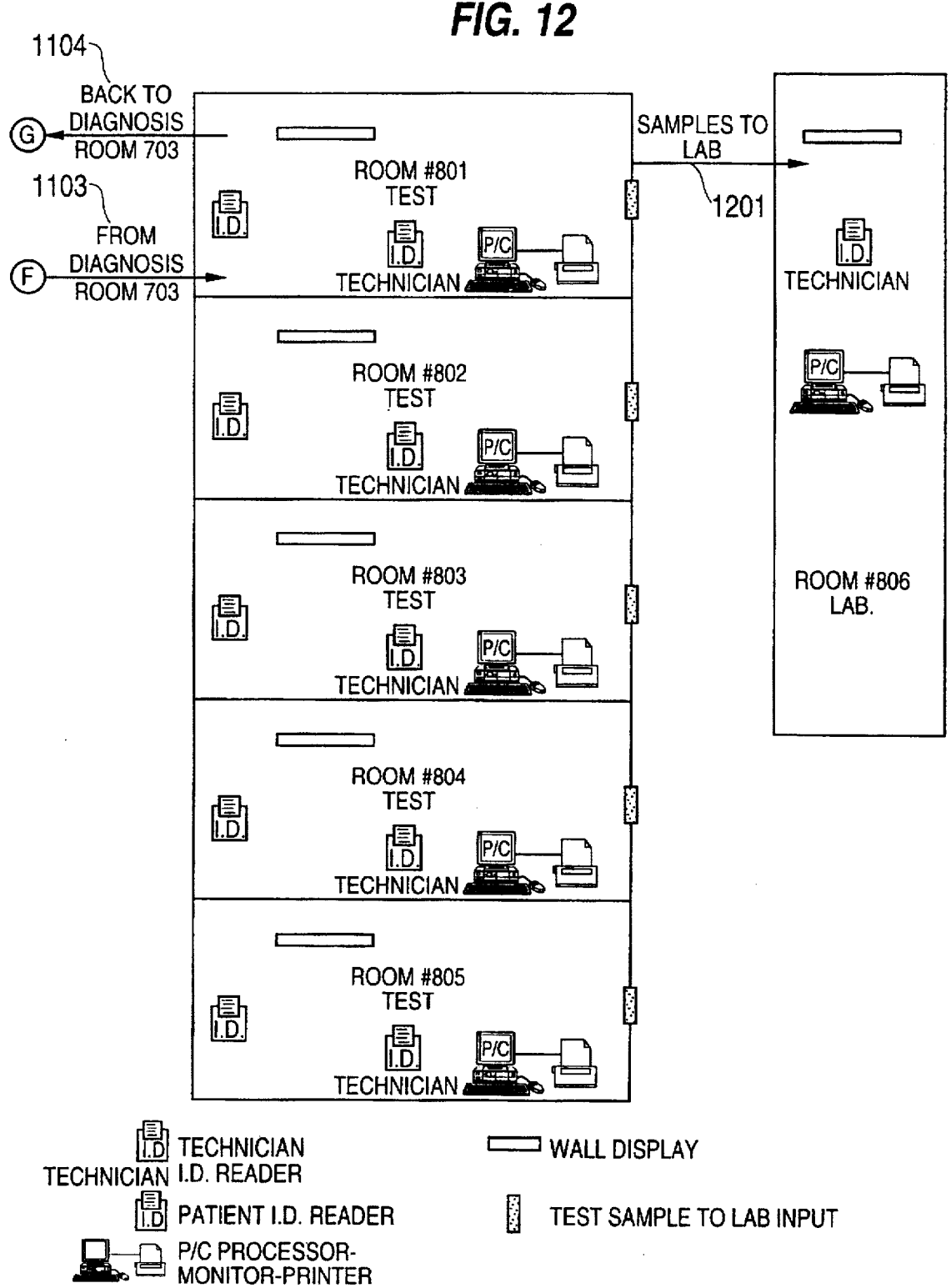

Reference is made to FIGS. 11 and 12, on Patient Flow.

Registered Patient Enters the Clinic:

The patient enters the clinic into the lobby and walks on a way 1101 up to the coordinator check-in window. The coordinator confirms the patient's appointment. At the scheduled time slot, the coordinator instructs the patient to proceed on a way 1102 to the assigned diagnostic room.

Diagnostic Room (Check-In)

In the diagnostic room, the patient meets the diagnostic nurse who interviews the patient and decides what tests are needed. The diagnostic nurse explains the reason for these tests and may review the patient's historical data with the patient. If the patient has symptoms indicating the need for an M.D. or a specialist, the nurse can contact a specialist or general practitioner for the patient on the spot. The patient's historical data will be sent on-line while the nurse establishes contact by phone. If needed, an appointment is made for the patient with the specialist right there.

Test Room and Laboratory Work

The patient is then instructed to proceed on a way 1103 to the assigned test room where the tests are performed. Label "F" in FIG. 11 continues to FIG. 12, showing Test Room and Laboratory Patient Flow. The test technician in the test room will administer the tests. If samples for laboratory work are required they are obtained in the test room and sent on a way 1201 into the Lab. The tests are all listed on a wall display so the patient is informed, preferably, at all times, which test is being performed and what the next step will be.

Diagnostic Room (Check-Out)

After testing has been completed, the patient is instructed to return on a way 1104 to the diagnostic room to review the test results with the same diagnostic nurse the patient met with previously. Label "G" on FIG. 12 continues to FIG. 11, showing coordinator, diagnostic, pharmacy, and In/Out room patient flow. The diagnostic nurse reviews not only the day's test results, but also leads the patient through a comparison of the patient's historical data with the day's results. The objective is to make the patient part of the process in understanding the progress the patient has made over time. The diagnostic nurse preferably makes a final diagnosis and explains this to the patient in terms the patient can understand. After the diagnosis is completed, the patient is instructed to proceed on a way 1105 to the pharmacy, if medication was prescribed by the Diagnostic nurse.

Pharmacy

At the pharmacy, the patient receives the prescription and the pharmacist goes over the instructions with the patient for taking the medication. Next, the pharmacist instructs the patient to proceed on a way 1106 back to the coordinator room.

Coordinator Check-out Window

At the check-out window, the coordinator sets up the next appointment with the patient, and hands the patient the printed visit summary. The coordinator ensures the patient understands this summary which shows that the insurer has already been invoiced, a listing of the day's test results, a comparison (if requested) to the patient's history of test results, and the next appointment. The patient now follows a way 1107 to leave the clinic.

3.3.2 Walk-in Patient Flow through In/Out Room

The purpose of this section is to explain how a walk-in patient flows through the clinic and what the purpose of visiting each room is. Walk-in patients are those patients that show up in the clinic without an appointment.

Master Processor 101 controls the flow of walk-in patients and all associated information flows in the same automatic real time method that is described for registered patients, and therefore the description of how the patient and the Master Processor 101 interact is not repeated here.

The walk-in patient is assigned a different route through the clinic (through an In/Out room) as opposed to through a diagnostic and test room. Following is a brief description of the flow of a walk-in patient.

Figure 13:
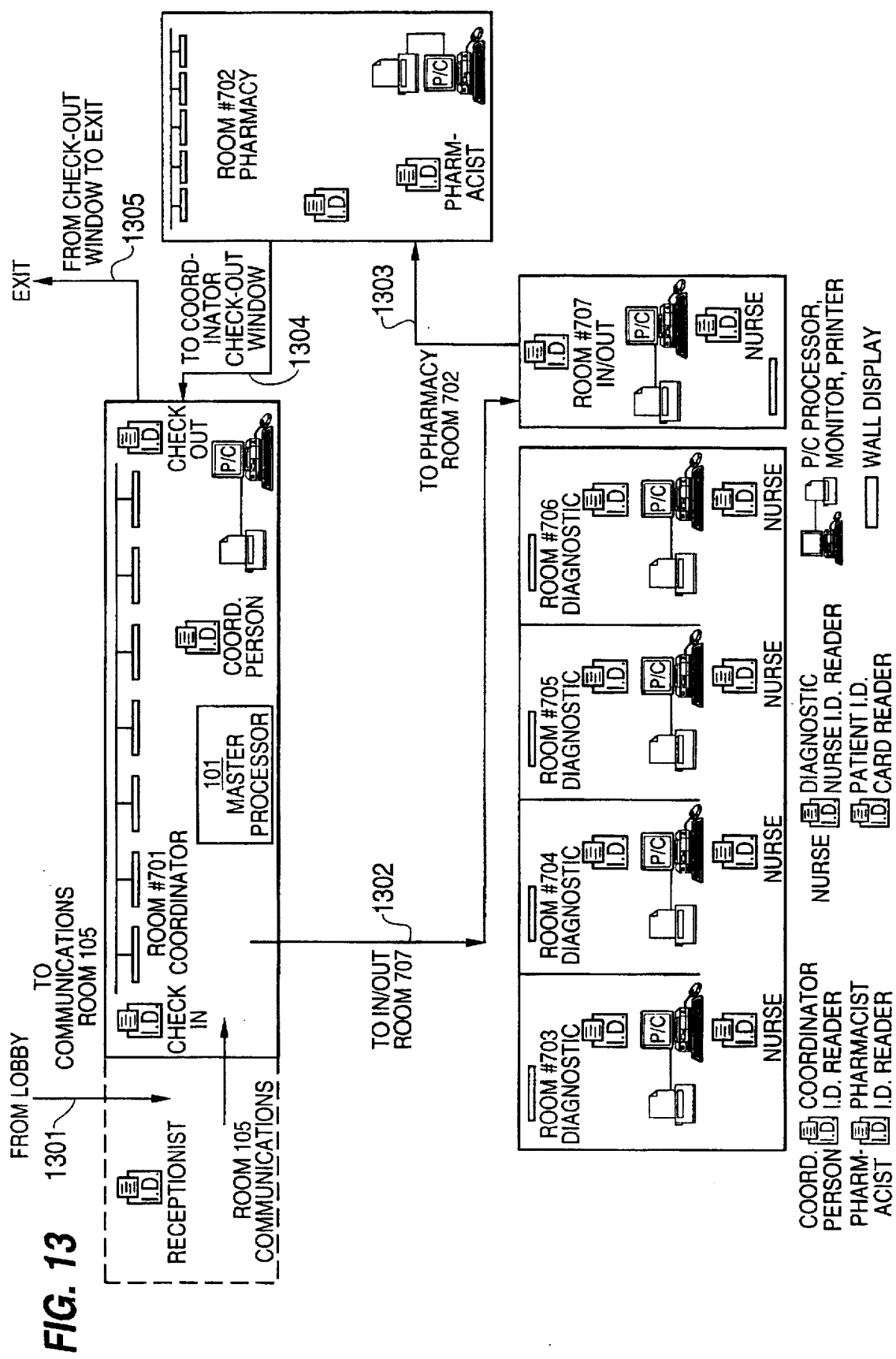
FIG. 13 shows the patient flow through the clinic for a walk-in patient.

Reference is made to FIG. 13, showing Walk-In Patient Flow.

Walk-in Patient enters Clinic

A patient walks into the clinic without an appointment. The patient walks on a way 1301 up to the communications room, and there the patient is classified as a walk-in patient. If this is the first time this patient is visiting the clinic, the patient is registered with the clinic and a patient I.D. card is prepared. The automatic management system will direct this patient through the In/Out room as soon as it becomes available. The receptionist enters the patient's information and gives the patient the option to either go through an In/Out room or have an appointment scheduled at a later time. It may be that time slots are available immediately, in which case the patient may also request tests and/or laboratory work and enter as a registered patient. After the receptionist has entered all patient information and the walk-in patient's insurance has been verified, the walk-in patient will wait in the lobby for the coordinator's signal to enter into an In/Out room.

Once an In/Out room becomes available, the coordinator instructs the walk-in patient to proceed on a way 1302 to the assigned In/Out room.

In/Out Room

In the In/Out room, the walk-in patient meets the diagnostic nurse who interviews the walk-in patient and decides if tests are needed. If so, an appointment will be scheduled for the walk-in patient. If test rooms are available, the patient will be treated as a registered patient. If no tests are needed and the walk-in patient can be treated on the spot, the diagnostic nurse preferably does so. If the walk-in patient has symptoms indicating the need for an M.D. or specialist (or emergency care for that matter), the diagnostic nurse via the automatic management system can contact a specialist or general practitioner for the walk-in patient on the spot. The walk-in patient's historical data will be sent on line while the nurse establishes contact by phone. If needed, an appointment is made for the walk-in patient with the specialist right there. After the diagnosis is completed, the walk-in patient is instructed to proceed on a way 1303 to the pharmacy, if medication was prescribed by the diagnostic nurse.

Pharmacy

At the pharmacy the walk-in patient receives the prescription and the pharmacist goes over the instructions with the walk-in patient for taking the medication. Next the pharmacist instructs the walk-in patient to proceed on a way 1304 back to the coordinator room check-out window.

Coordinator Check-out Window

At the check-out window, the coordinator sets up the next appointment with the walk-in patient, if further testing is required, and hands the walk-in patient the printed visit summary. The coordinator ensures the walk-in patient understands this summary which shows that the insurer has already been invoiced, a listing of the day's test results, and the next appointment. The walk-in patient now follows a way 1305 leave the clinic.

3.4 Automatic Real-Time Management of Patient and Employee Flow

This section describes the methods of how the patient and employee flow and location are automatically managed by the Master Processor 101 and how the Master Processor 101 interacts in real-time with the input and output components in each room throughout the clinic to do so.

3.4.1 I.D. Card Code Inputs

Figure 14:
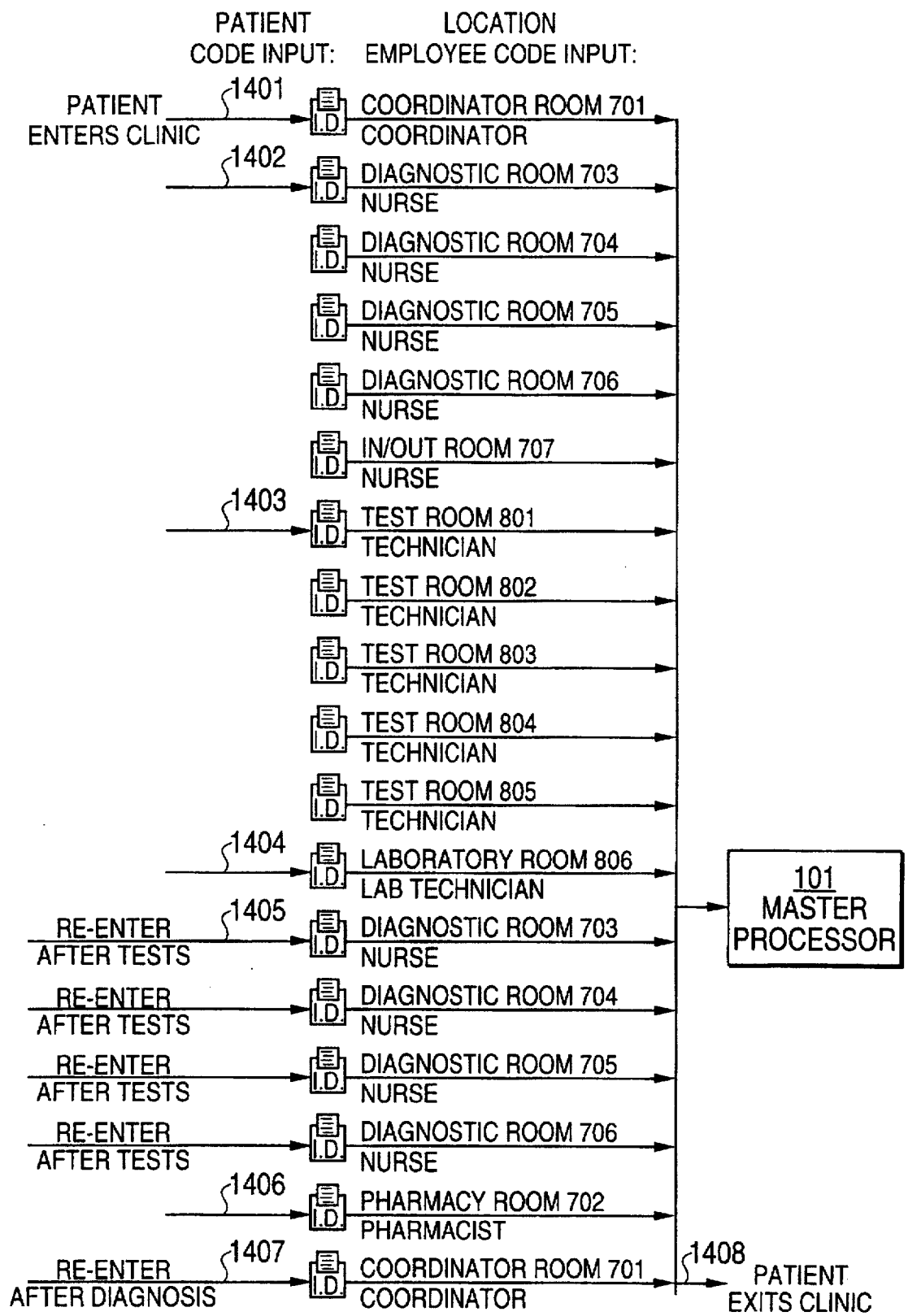
FIG. 14 is an expansion of all card reader inputs to the master processor.

Reference is made to FIG. 14, showing Patient and Employee I.D. Card Slots and Sequence Through Clinic. FIG. 14 shows the I.D. card code inputs the Master Processor 101 receives as the patient flows through the clinic. I.D. card code inputs are received from both the employee and the patient as they insert and extract their I.D. cards from the card readers in each room throughout the clinic. Secondly, every time an input is received from a card reader, the location of this card reader is passed on to the Master Processor 101.

Once the patient arrives at the clinic (1401), the patient flows from the coordinator room to a diagnostic nurse where tests are decided upon (1402). The patient then flows through the test room where (1403) all the tests are performed by a technician and where samples are passed (1404) into the lab. After testing is done, the patient then flows back to the same diagnostic nurse for test review (1405), through a pharmacy for pick-up of medication (1406), and back to the coordinator room (1407) where the coordinator prepares the invoice and the next appointment.

Figure 15:
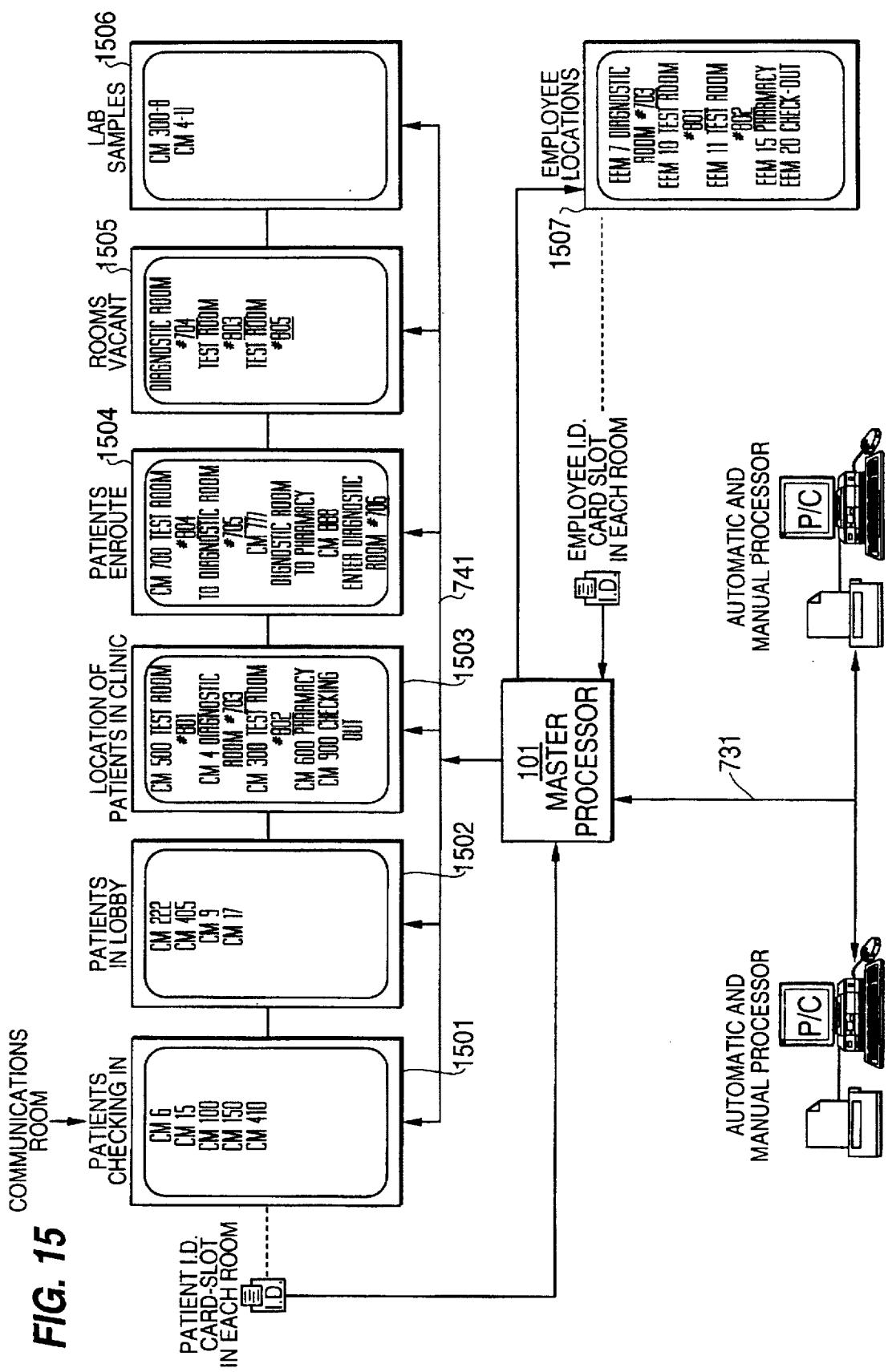
FIG. 15 is a block diagram showing displays connected to the master processor in the coordinator room.

FIG. 15, illustrating Coordinator Room Displays, shows, based on the I.D. card code inputs, how the Master Processor 101 also alerts the coordinator in the coordinator room of the status of all employees and patients throughout the clinic. Just some sample displays are shown for illustrative purposes. They are: 1501—Patients Checking In; 1502—Patients Waiting in the Lobby; 1503—Location of each Patient in the Clinic; 1504—Patients En Route to a Room in the Clinic; 1505—Vacant Rooms in the Clinic; 1505—Laboratory Samples in the Laboratory; and 1507—Location of Employees in the Clinic. Other displays may be added or deleted. These displays are also referred to as a group by label 741 (from FIG. 7). The P/C processor 731 in the coordinator room can be used by the coordinator to interact with the Master Processor 101 regarding status or concerns the coordinator may have. Multiple P/Cs may be in place here depending on the workload and configuration of the clinic.

3.4.2 Automatic Flow Management of Patients and Employees

Reference is made to FIGS. 7 and 8, which illustrate Automatic Real-Time Inputs and Outputs for all components in all rooms throughout the clinic, in one embodiment of the invention.

Registered Patient Enters the Clinic

Once the patient arrives at the clinic, the patient I.D. card input is taken in the coordinator room 701 check-in window at a slot 721 by Master Processor 101. In the coordinator room 701 on the display 741 the Master Processor 101 displays patient I.D. as present in the lobby. Insurance is automatically verified by the Master Processor 101 via the communications room 105, and a message is automatically displayed by the Master Processor 101 on display 741 that verification of insurance is in progress. Once insurance is verified, the Master Processor 101 automatically selects a diagnostic room and displays the selected diagnostic room on display 741 in coordinator room 701, instructing the patient to proceed to this room. Once the patient I.D. card is extracted from the card reader 721, the Master Processor 101 displays the patient I.D. as en route to diagnostic room 703 on the display 741 in coordinator room 701.

Diagnostic Room (Check-In)

Upon entry into diagnostic room 703, the patient I.D. card input is taken at a slot 724 by the Master Processor 101. In coordinator room 701 on display 741 Master Processor 101 automatically displays patient I.D. as present in diagnostic room 703. Once the diagnostic nurse has finished entering the selected tests via P/C at 733, selected tests are automatically transmitted to the Master Processor 101 by P/C at 733. The Master Processor 101 automatically selects a test room and displays selected test room 801 on display 743 in diagnostic room 703 instructing the patient to proceed to this room. The Master Processor 101 also automatically displays selected tests on display 841 in test room 801 (see FIG. 8). Once the patient I.D. card is extracted from the card reader 724, Master Processor 101 automatically displays patient I.D. as en route to test room 801 on display 741 in the coordinator room 701.

Test Room and Laboratory Work

Reference is made to FIG. 8. Upon entry into test room 801 the patient I.D. card input is taken at slot 821 by the Master Processor 101. In coordinator room 701 on display 741 the Master Processor 101 automatically displays the patient I.D. as present in the test room 801. If tests require laboratory work, the Master Processor 101 automatically prints labels containing the patient I.D. for samples via the P/C 831. Once samples are passed into the laboratory 806 directly from test room 801, an input from 851 is provided to the Master Processor 101, and in the coordinator room 701 on display 741 the Master Processor 101 automatically displays patient I.D. laboratory samples as present in laboratory 806. Test results from test room 801 and laboratory 806 are automatically transmitted to the Master Processor 101 by the P/C 831, 836. Upon completion of final tests, the Master Processor 101 automatically selects the same diagnostic room with the same diagnostic nurse the patient started out in for evaluation of test results and diagnosis. The Master Processor 101 automatically displays the selected diagnostic room 703 on the display 841 in the test room 801, instructing the patient to proceed to that room. The Master Processor 101 also automatically transmits all test results to diagnostic room 703 at P/C 733. Once the I.D. card is extracted from the card reader 821, the Master Processor 101 automatically displays patient I.D. as en route to the diagnostic room 703 on display 741 in the coordinator room 701.

Diagnostic Room (Check-Out)

Upon entry into diagnostic room 703, the patient I.D. card input is taken at the slot 724 by the Master Processor 101. In coordinator room 701 on the display 741, the Master Processor 101 automatically displays patient I.D. as present in the diagnostic room 703. Selected or entered diagnoses are automatically transmitted to the Master Processor 101 by the P/C 733. If a selected diagnosis includes a prescription, the Master Processor 101 will automatically transmit this to the P/C 732 in the pharmacy 702 where labels and instructions will automatically be printed at the P/C 732 and displayed for patient I.D. on display 742 in the pharmacy. The Master Processor 101 automatically displays the pharmacy 702 on display 743 in the diagnostic room 703 instructing the patient to proceed to this room. If no prescription is required, Master Processor 101 instructs the patient to the next room by automatically displaying the coordinator room 701 on display 743 in the diagnostic room 703. Once the patient I.D. card is extracted from the card reader 724, the Master Processor 101 automatically displays patient I.D. as en route to the pharmacy 702 (or the coordinator room 701) on display 741 in the coordinator room 701.

Pharmacy

Upon entry into the pharmacy 702, the patient I.D. card input is taken at the slot 723 by the Master Processor 101. In the coordinator room 701 on display 741, the Master Processor 101 automatically displays patient I.D. as present in the pharmacy 702. Upon receipt of prescription, the Master Processor 101 automatically displays the coordinator room 701 on display 742 in the pharmacy 702 instructing the patient to proceed to this room. Once the patient I.D. card is extracted from the card reader 723, the Master Processor 101 automatically displays patient I.D. as en route to the coordinator room 701 on the Display 741 in the coordinator room 701.

Coordinator Check-out Window

Upon entry into the coordinator room 701 check-out window, the patient I.D. card input is taken at the slot 722 by the Master Processor 101. In the coordinator room 701 on Display 701, the Master Processor 101 displays the patient I.D. as present in the coordinator room 701. Upon selection of next appointment via the P/C 731, the Master Processor 101 automatically prints out visit summary via printer at the P/C 731. Invoicing information is also automatically transmitted to insurer by the Master Processor 101 via communications room 105 resources. Upon extraction of the patient I.D. card from card reader 722 the patient leaves the clinic.

Control of Employee Flow

Just as each patient is required to insert a patient I.D. card into a card reader upon arrival into each room and extract the I.D. upon leaving the room, the employees are required to do the same. In this manner, the Master Processor 101 will only assign rooms where patients can be immediately served by a nurse or technician. Also, the coordinator has employee locations displayed as well, providing for planning of staffing levels and monitoring and ensuring these staffing levels are taking place. Such employee card readers include: Coordinator I.D. Reader 711, Pharmacist I.D. Reader 712, Diagnostic Nurse I.D. Readers 713–717, Test and laboratory Technician I.D. Reader 811–816, and the receptionist I.D. reader 213 in the communications room.

3.5 Automatic Real-Time Management of Patient, Employee and Information Flow and Sample Programs of Real-Time Interaction This section describes the methods of how patient information is automatically managed by the Master Processor 101. It describes how the Master Processor 101 interacts real-time, with all inputs, outputs and historical aspects of the clinic and patient to do so.

Figure 16:
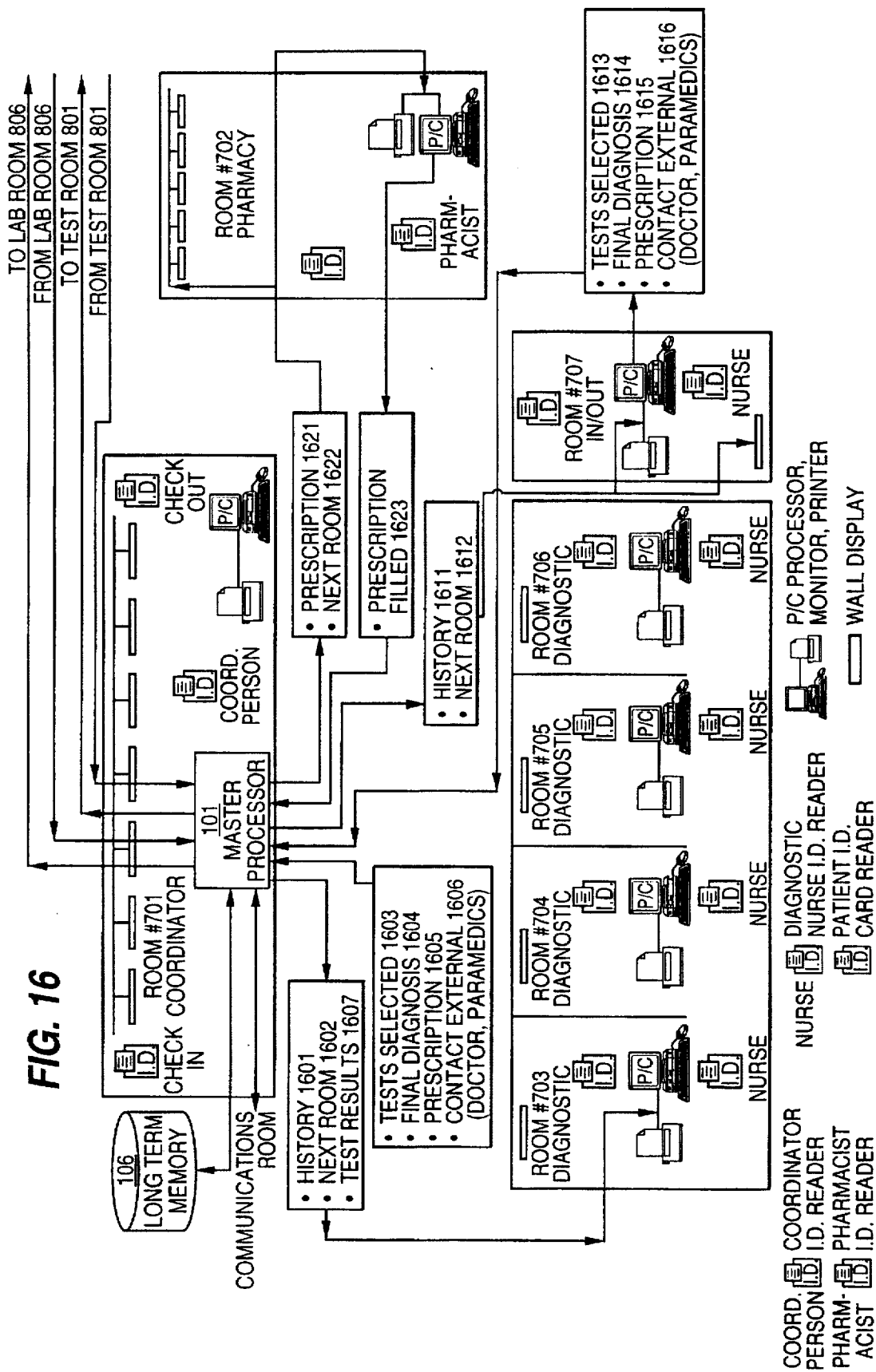
FIGS. 16 and 17 are flow diagrams showing how the master processor automatically real-time manages the information associated with patient flow through the clinic.
Figure 17:
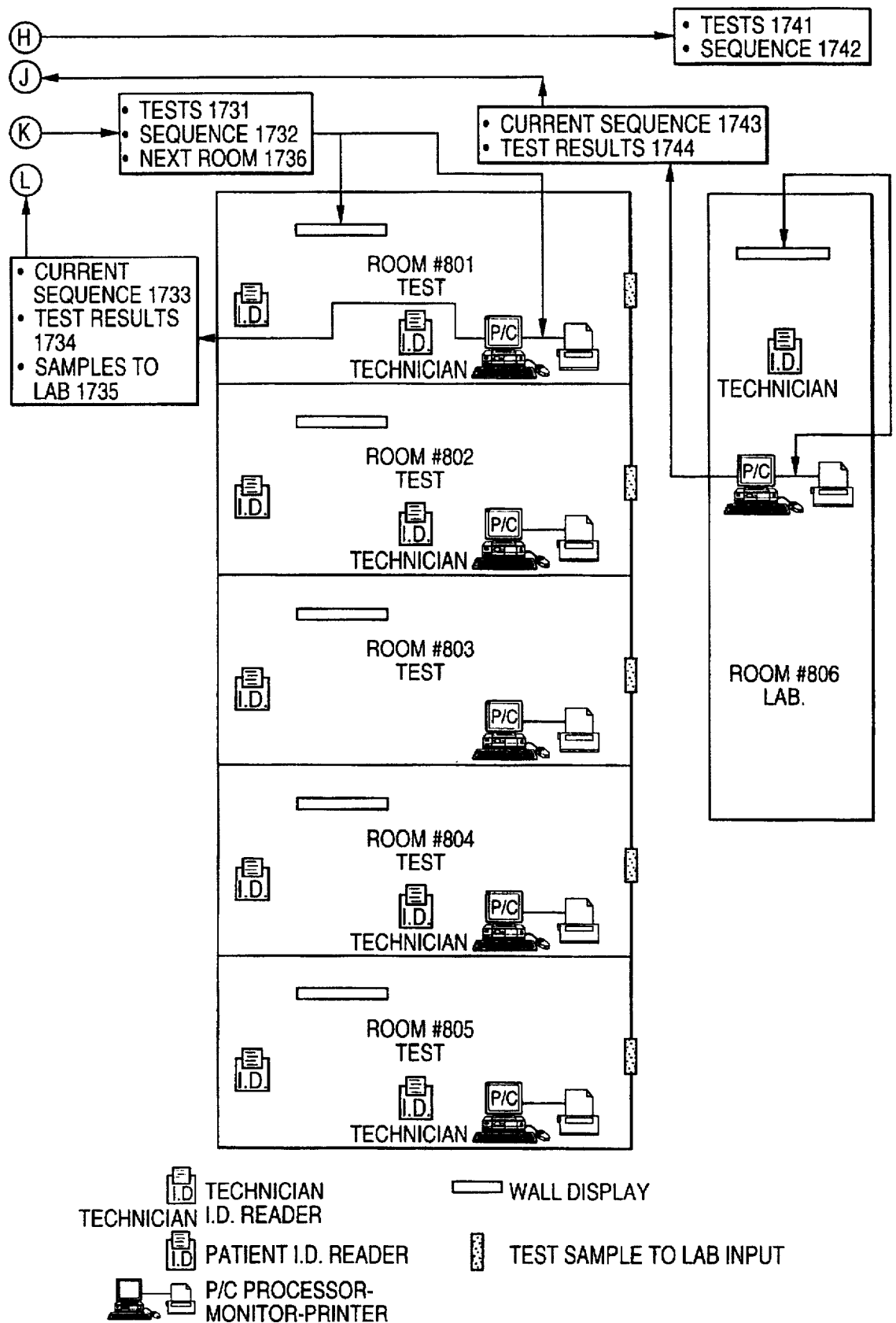

Throughout section 3.5 references to FIGS. 16 and 17, illustrating Information Flow Management, will be made. In several cases, further detail will be added by referencing sample programs which the Master Processor 101 executes, through flow charts and descriptions.

Again, the patient flow through the clinic is used as a vehicle to describe the aspects of the dynamic, interactive, fully automatic real-time management system. This section adds the information flow to the already described automatic management of patient and employee flow.

Registered Patient Enters the Clinic

At the check-in window, in the coordinator room the patient I.D. card input triggers Master Processor 101 into action. Master Processor 101 automatically interacts the I.D. code read from the card reader with the I.D. numbers in the Long Term Memory 106 and confirms that the patient has an appointment. If the patient is early, the patient will wait in the lobby. The Master Processor 101 also automatically via the communications room verifies insurance coverage and informs the insurer of the patient's presence and scheduled tests at the clinic. Insurance verification and invoicing is covered in detail in the communications room description. Patient name, appointment and insurer information are automatically displayed at the coordinator P/C by Master Processor 101. Master Processor 101 also displays on the coordinator room display that insurance verification for the input patient I.D. code is in progress.

Sample program

Figure 18:
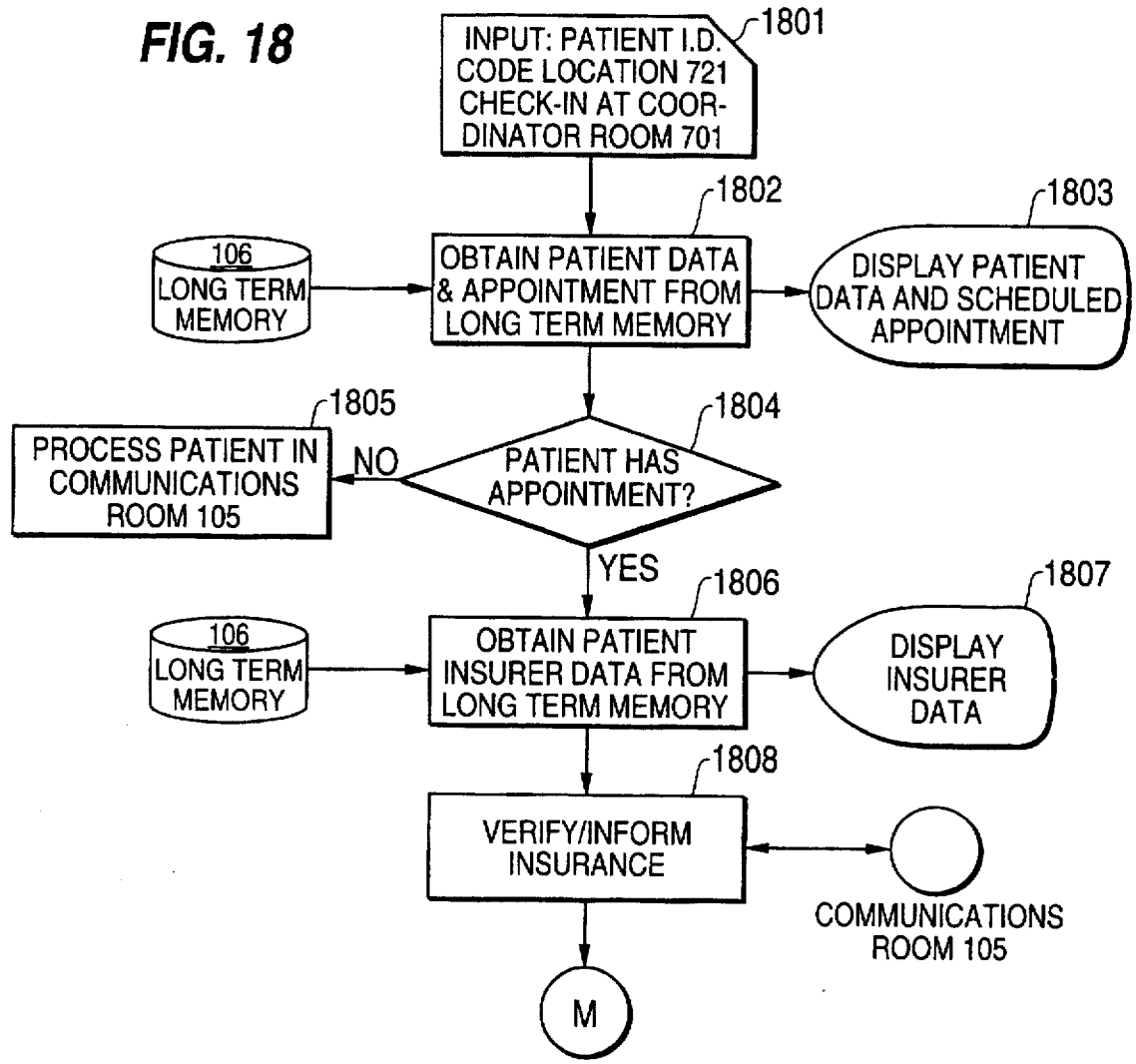
FIG. 18 shows automatic real-time interaction by the master processor when the patient I.D. code input is received at the coordinator check-in location.

FIG. 18, illustrating Registered Patient Enters Clinic, shows a short-hand flow chart of how once given the patient I.D. input at the coordinator check-in location, the Master Processor 101 automatically in real-time verifies insurance for the patient. The known event indicated by block 1801 is the Patient I.D. input 721 from the coordinator check-in I.D. card reader. This starts a sequence of events to determine the unknown: the patient's insurance carrier.

The patient's data and appointment time slot is obtained from the Long Term Memory 106 at block 1802 and is displayed for the coordinator on the coordinator wall display at block 1803. This allows the coordinator to verify if the patient has an appointment and if the patient is on time. If the patient has no appointment near the current time slot, the coordinator instructs the patient to proceed to the communications room where the patient can be processed for an appointment as shown in blocks 1804 and 1805. If the patient had an appointment scheduled per block 1804, the patient's insurer information is obtained from the Long Term Memory 106 at block 1806 and this information is displayed on the coordinator wall display at block 1807. Automatic insurance verify action now takes place at block 1808 via resources in the communications room 105. The insurance verification is now complete and this becomes a known factor (block M) for the next step: selection of a diagnostic room.

Once insurance verification is complete, the Master Processor 101 automatically selects a diagnostic room.

Selecting a Diagnostic Room

The Master Processor 101 selects a diagnostic room by interacting in real-time the status of all diagnostic rooms, all diagnostic nurses, and the total number of patients in the clinic. Once an idle diagnostic room with a diagnostic nurse is found, the Master Processor 101 automatically displays this diagnostic room number on the display in the coordinator room.

Sample Program

Figure 19:
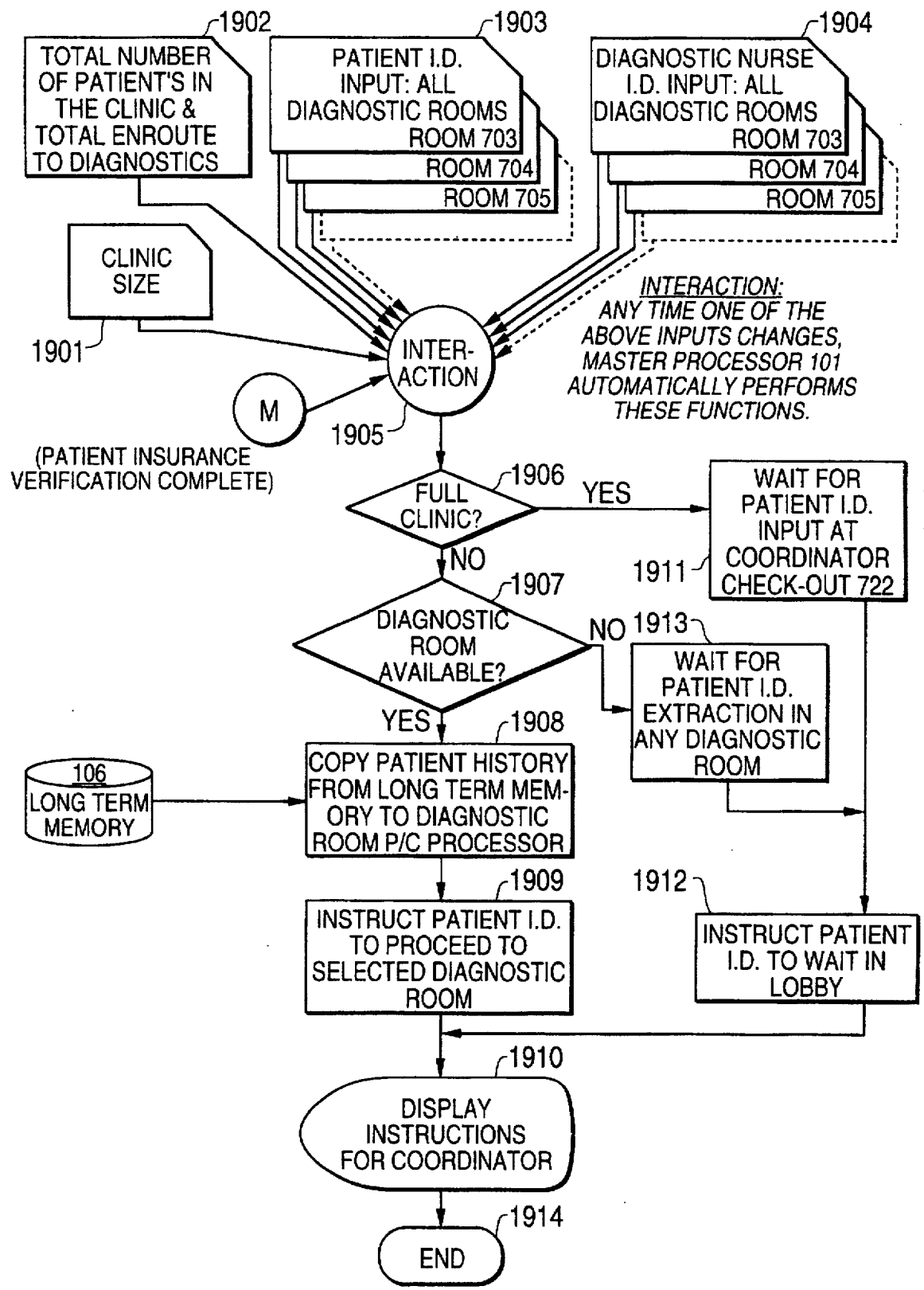
FIG. 19 shows automatic real-time interaction by the master processor for selecting a diagnostic room for a patient, and limiting the total number of patients in the clinic.

FIG. 19, illustrating Diagnostic Room Selection, shows a short-hand flow chart of how the Master Processor 101 automatically in real-time interacts all inputs to select the diagnostic room, and how the Master Processor 101 automatically limits the number of patients in the clinic.

The known events are indicated by block 1901—the clinic size from Long Term Memory 106, block 1902—the total number of patients currently in the clinic and the total number of patients currently en route to any diagnostic room, block 1903—all patient I.D. inputs from all diagnostic rooms, block 1904—all Diagnostic nurse I.D. inputs, and label "M" insurance verification complete. Interaction takes place between these inputs as indicated by block 1905 which starts a sequence of events to determine the unknown: an assignment of an available diagnosis room with a diagnostic nurse without overloading the clinic with waiting patients.

At block 1906, a decision is made if any more patients should be processed from the lobby past the coordinator check-in counter. This is based on the clinic size obtained from 1901 which indicates total allowable number of patients in the facility, and based on the total number of patients currently in the clinic 1902. The total number of patients currently in the clinic is increased each time a patient passes the coordinator check-in counter and is decreased each time a patient passes the coordinator check-out counter. If the current number of patients in the clinic does not exceed the total allowable patients, a check for a diagnostic room and nurse is made at block 1907 from inputs 1903 and 1904. If a diagnostic room with a diagnostic nurse is available and no patients are currently en route to that diagnostic room (input 1902) that diagnostic room is selected. Block 1908 copies patient history (the patient I.D. is known through the block labelled M) from Long Term Memory 106 to the P/C processor in the selected diagnostic room for viewing by the diagnostic nurse. At block 1909 the patient is instructed to proceed to the selected diagnostic room by displaying these instructions on the coordinator room wall display for the coordinator at block 1910. At block 1914 the sequence of events ends.

If it turns out that at block 1906 no additional patients can currently enter past the coordinator, an interaction is set up at block 1911 to wait for a patient I.D. input to pass the coordinator check-out window before this patient can be called in. The coordinator is instructed at block 1912 through a displayed message to instruct the patient to wait in the lobby.

If it turns out that at block 1907 no available diagnostic room could be found, a similar interaction is set up at block 1913 to wait for a patient I.D. extraction input from any diagnostic room. At block 1912 the patient is instructed to wait in the lobby in the meantime. Limiting the number of patients in the test and diagnostic rooms coupled with appointment scheduling that takes the size and workload of the clinic into account, patient waiting will be controlled automatically by the Master Processor 101.

Reference is made back to FIG. 16. The Master Processor 101 automatically sends the patient's historical data 1601 from the Long Term Memory 106 to the P/C processor in the diagnostic room. This readies the P/C in the selected diagnostic room for input by the Diagnostic nurse.

Upon extraction of the patient I.D. card from the coordinator check-in window, the Master Processor 101 automatically displays on the coordinator and diagnostic room displays that the patient is en route to the diagnostic room. The patient now walks from the coordinator room to the diagnostic room.

Diagnostic Room (Check-In)

In the diagnostic room, the diagnostic nurse interviews the patient and reviews the patient's history via the P/C. Using menus on the P/C display, the diagnostic nurse selects the tests to be performed.

Figure 20:
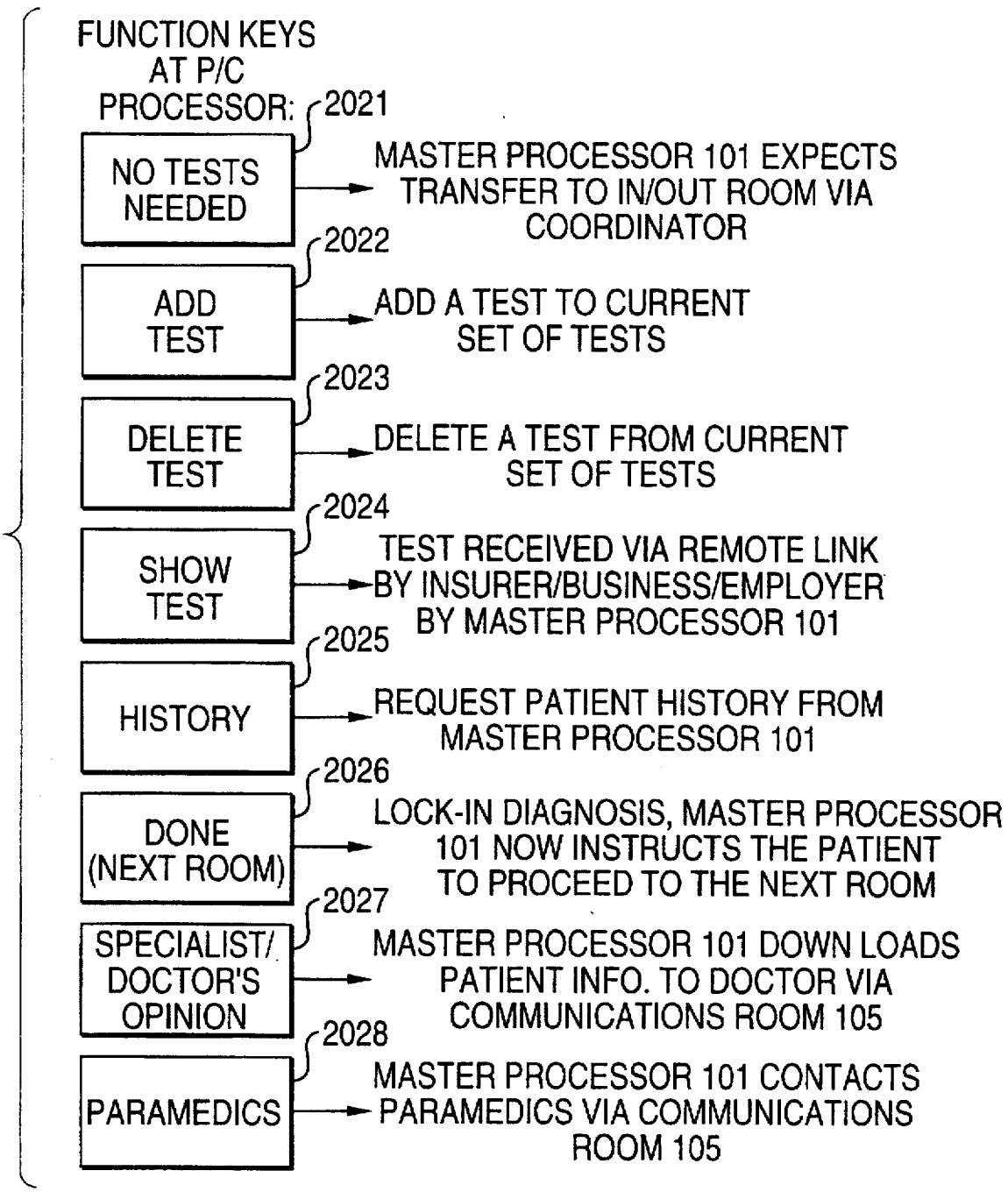
FIG. 20 shows the diagnostic and in/out room function keys for the diagnostic nurse.

Reference is made to FIG. 20, which shows Diagnostic Room Functions at P/C Processor, for function keys the diagnostic nurse uses. These function keys exhibit the type of functions the diagnostic nurse performs at this stage. "No Tests Needed" 2021 is selected if the nurse decides no tests are needed to complete diagnosis. The "Add Test" 2022, "Delete Test" 2023, and "History" 2025 function keys are used to browse through menus of possible tests that can be offered. The "Show Tests" 2024 applies when the patient is at the clinic for a standard set of tests or if the patient arrived with instructions for testing from, for example, an employer or physician. This information is then provided by the Master Processor 101 as part of the patient's historical data. The "Done" 2026 function is selected at completion of the diagnosis session. Other function keys may be added. Two further examples are "Specialist/Doctor's Orientation" 2027 and "Paramedic" 2028. If the nurse decides that on-line viewing of patient data is warranted by a physician, a physician can be contacted on-line. Paramedics can be contacted on-line if it turns out the patient requires immediate emergency care.

Referring to FIG. 16 again, once the diagnostic nurse completes the selection process, the P/C processor in the diagnostic room alerts the Master Processor 101 that check-in diagnosis is complete. The Master Processor 101 automatically receives the selected test information input 1603 from the diagnostic room P/C processor, which triggers the Master Processor 101 to select an available test room. Master Processor 101 also automatically updates Long Term Memory 106 with the current status of this patient; the specific nurse I.D. and diagnostic room the patient will return to after testing, the selected tests, and patient response to the interview entered by the diagnostic nurse.

Once an idle test room with a technician is selected, the Master Processor 101 automatically displays the test room number on the display in the coordinator room and the diagnostic room (see 1602—next room). If no idle test room is available, the patient will wait directly outside the diagnostic room. As soon as the Patient I.D. card is extracted from the I.D. card slot in a test room, Master Processor 101 through this input will assign the waiting patient the test room and alert the diagnostic nurse through the wall display in the diagnostic room to send the patient to the test room.

Reference is made to FIG. 17, which shows Test Room and Laboratory Information Flow Management. Once a test room has been selected, the Master Processor 101 automatically sends the patient's data (tests 1731) from Long Term Memory 106 to the P/C processor in the selected test room. This readies the P/C processor in the selected test room for input by the technician. Master Processor 101 also automatically displays the tests in sequence 1732 on the wall display in the selected test room. Note that FIGS. 16 and 17 are interconnected by continuation labels H,J,K, and L. Following is a sample program illustrating how Master Processor 101 executes these functions.

Sample Program

Figure 21:
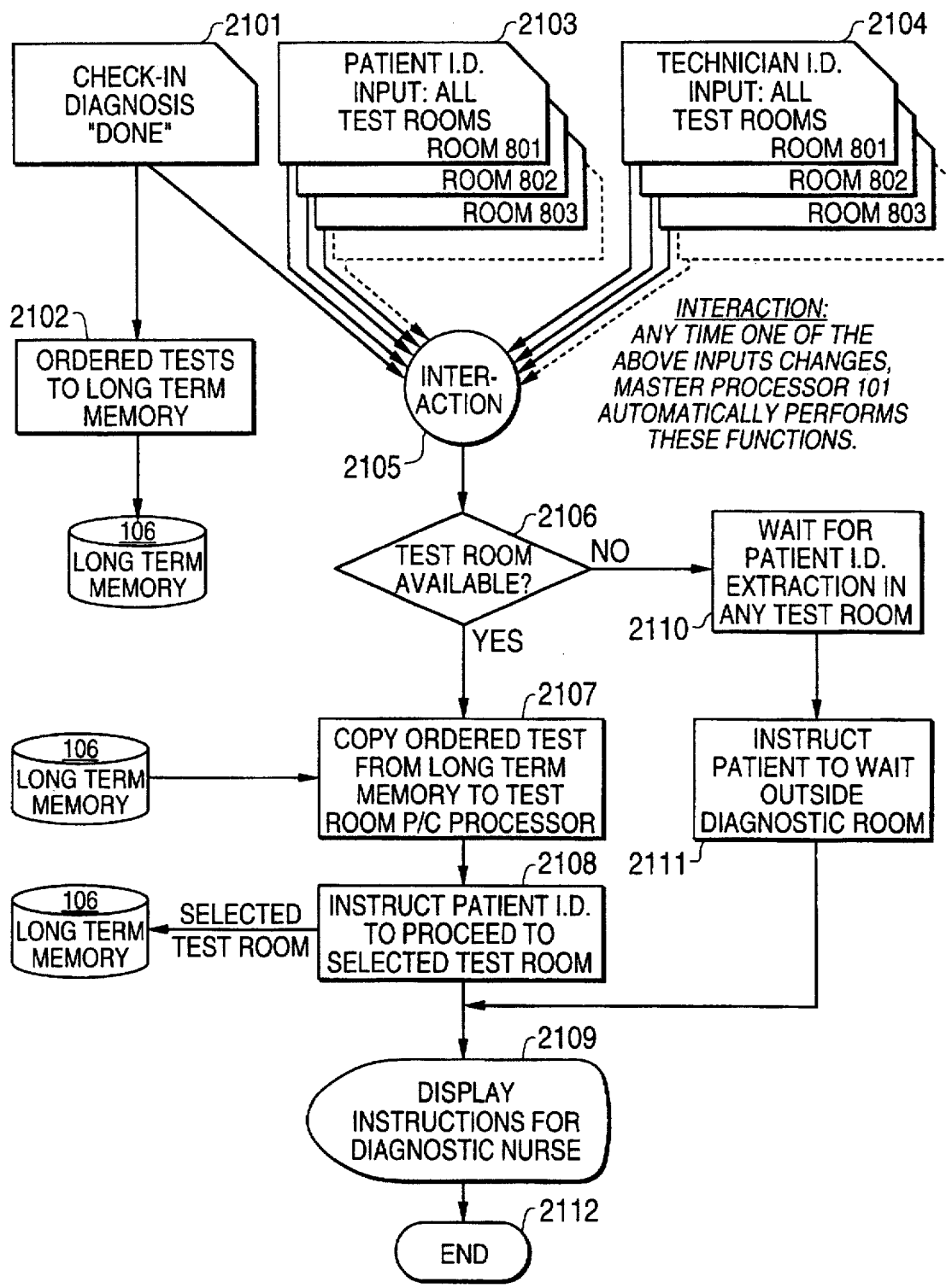
FIG. 21 shows automatic real-time interaction by the master processor for selecting a test room for a patient.

FIG. 21, illustrating Test Room Selection, shows a short-hand flow chart of how once the "Check-In Diagnosis Done" function key is selected by the diagnostic nurse, Master Processor 101 automatically in real time selects a test room. As shown in block 2102, ordered tests from check-in diagnosis are transferred to Long Term Memory 106.

The known events indicated by blocks 2101, 2103, and 2104 are the check-in diagnosis "Done" input from the diagnostic nurse, all patient I.D. inputs currently at all test rooms (including patients en route to any test room), and all test room technician I.D. inputs currently at all test rooms. Interaction takes place between these inputs as indicated by block 2105 which starts a sequence of events to determine the unknown: an assignment of an available test room with an available technician.

If at block 2106 a test room with technician is found (input 2104), and currently no patient is en route (input 2103), the selected tests are copied at block 2107 from Long Term Memory 106 to the P/C processor in the selected test room. The selected test room is now a known factor and is stored in Long Term Memory 106 at block 2108, and instructions for the diagnostic nurse to send the patient to the test room are displayed at block 2109 in the diagnostic room.

If it turns out that at block 2106 no test room could be found, an interaction is set up at block 2110 to wait for a patient I.D. extraction in any test room. The diagnostic nurse is instructed to tell the patient to wait right outside the diagnostic room at block 2111 through a displayed message at block 2109. At block 2112 the sequence of events ends.

Upon extraction of the patient I.D. card from the diagnostic room, the Master Processor 101 automatically displays on the coordinator and test room displays that the patient is en route to the selected test room. The Master Processor 101 obtains this information from Long Term Memory 106 using the patient I.D. as an index. The patient now walks from the diagnostic room to the selected test room.

Sample Program

Figure 22:
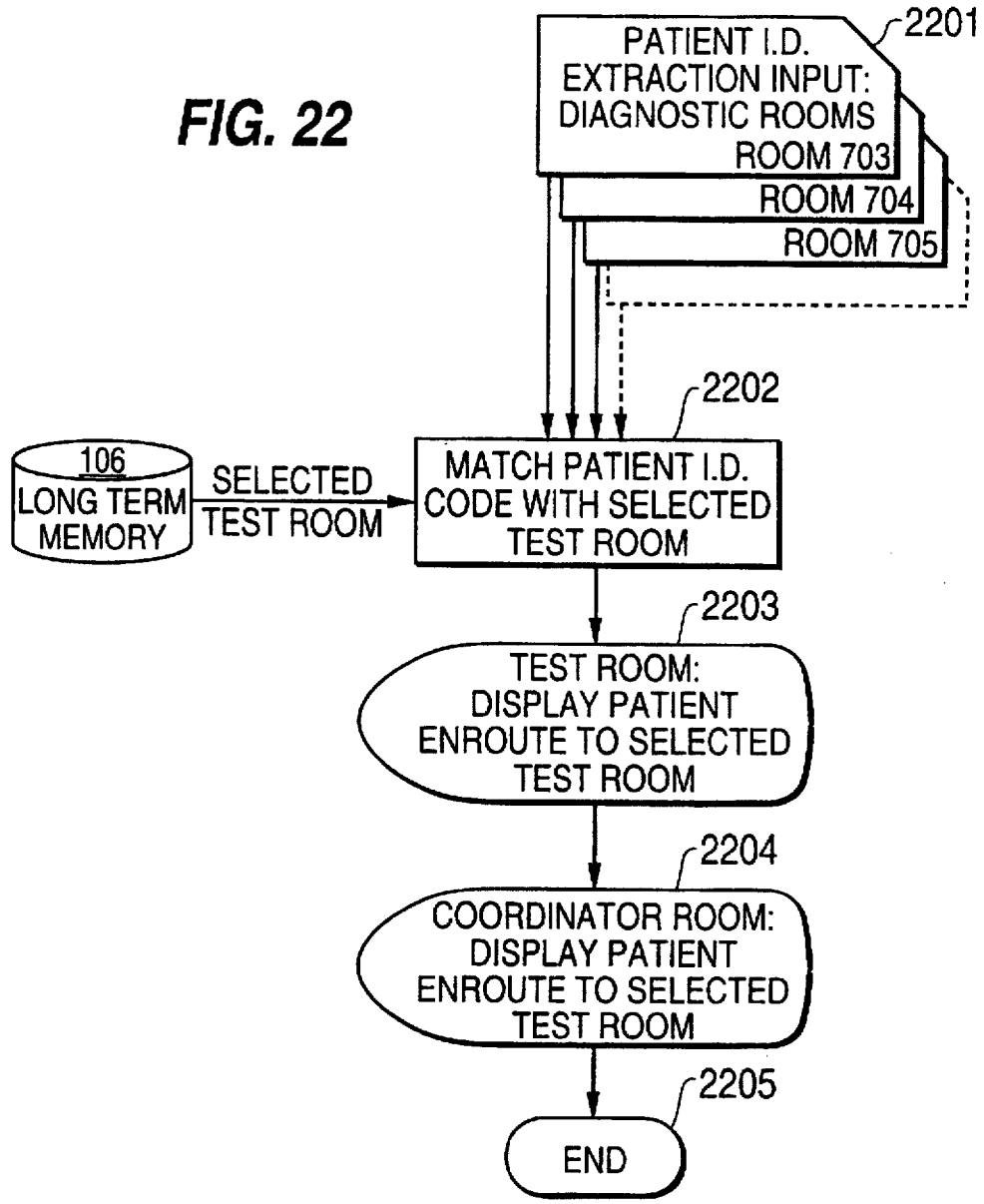
FIG. 22 shows automatic real-time interaction by the master processor when the patient removes the patient I.D. card from the I.D. slot in the diagnostic room in order to proceed to a test room.

FIG. 22, illustrating Patient Leaves Diagnostic Room, shows a short-hand flow chart of how the Master Processor 101 automatically in real-time displays all messages as soon as the patient I.D. card is extracted from the diagnostic room I.D. slot.

The known event indicated at block 2201—the extraction of the patient I.D. card at a diagnostic room starts a sequence of events to display messages at several locations in the clinic regarding the status change of the patient.

At block 2202 the patient I.D. code is matched with the already selected test room from the Long Term Memory 106. Next a message is displayed in the test room at block 2203 alerting the technician the patient is en route. The tests are already displayed on the wall display. At block 2204 the same message is displayed for the coordinator on the status display. Block 2205 ends the sequence of events.

Test Room

Reference is made to FIG. 17 (note that FIGS. 16 and 17 are interconnected by continuation labels H, J, K, and L). In the test room, the technician performs the tests in the sequence shown on the wall display. As soon as the patient I.D. input is taken in the test room the testing sequence can commence. The technician uses the function keys at the P/C processor to acknowledge the completion of each test. This is provided as an input 1733—the current sequence—to the Master Processor 101 by the P/C processor in the test room.

Upon completion of all tests, the Test Room P/C processor provides all test results 1734 as an input to the Master Processor 101. The Master Processor 101 automatically updates the patient history in Long Term Memory 106 with these test results.

Automatic test equipment

Instead of the Master Processor 101 using the P/C processor in the test room to obtain the test data, the test data could be obtained real-time directly from the testing equipment. Real-time communications links could also be set up to an outside doctor's office via the communications room 105.

Next, the Master Processor 101 automatically determines the diagnostic room the patient originally visited and should return to for review of the test results and final diagnosis. Master Processor 101 automatically obtains this from the Long Term Memory 106, and automatically displays the selected diagnostic room 1736 (next room) the patient should proceed to on the wall display in the test room.

Upon extraction of the patient I.D. card from the test room, the Master Processor 101 automatically displays on the coordinator and selected diagnostic room wall displays that the patient is en route to the selected diagnostic room. The patient now walks from the test room to the selected diagnostic room. If no diagnostic nurse is available, the patient will wait directly outside the diagnostic room. As soon as the diagnostic nurse becomes available (upon extraction of the patient I.D. card the nurse is currently with), Master Processor 101 will alert the diagnostic nurse that a patient is waiting outside. These patients are given priority by Master Processor 101 over patients waiting in the lobby for a diagnostic nurse.

Laboratory Work

If the testing sequence in the test room requires the taking of a sample for laboratory analysis, when this sequence step is reached the Master Processor 101 automatically instructs the P/C processor in the test room to print a label for each sample.

Sample Program

Figure 23:
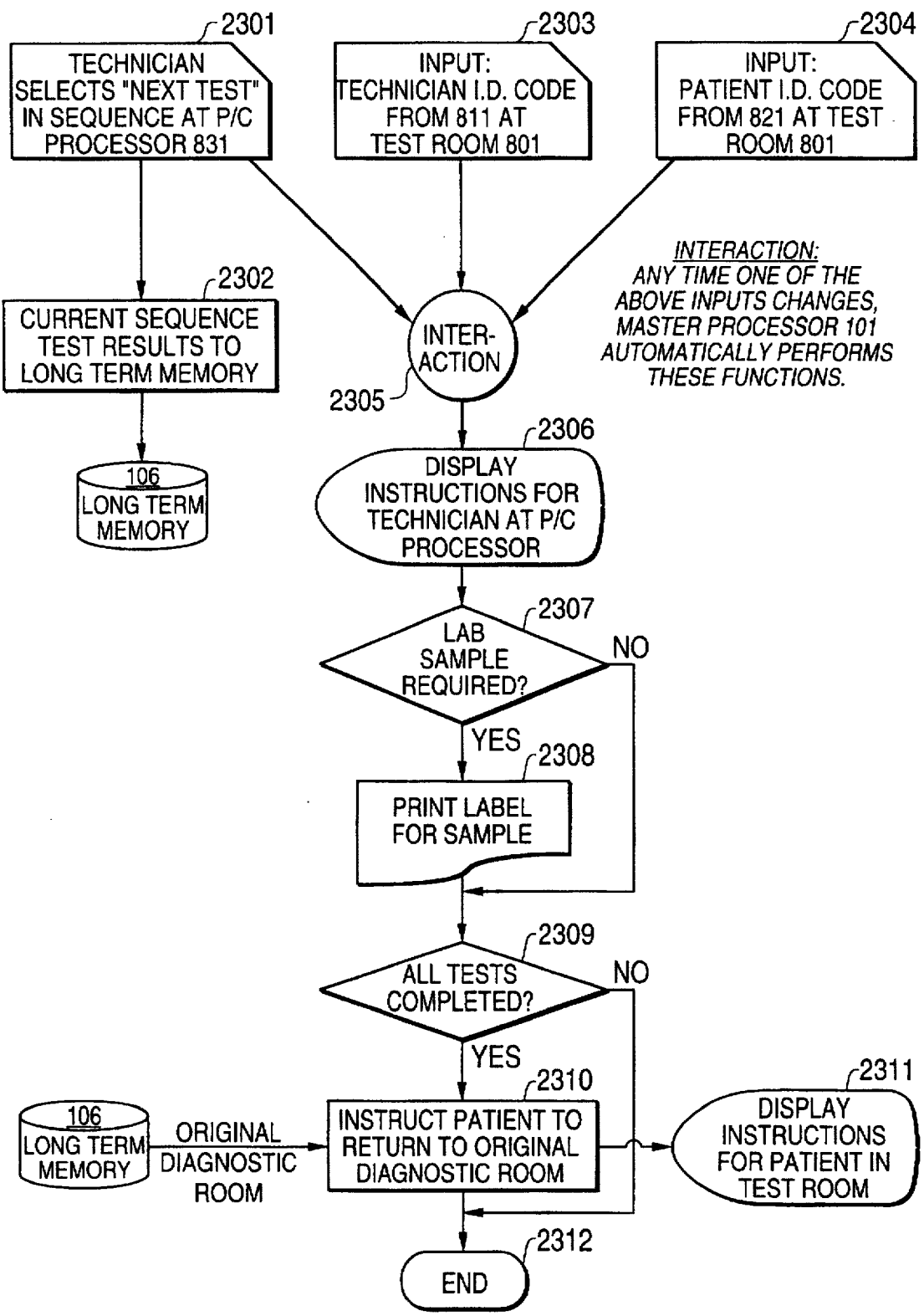
FIG. 23 shows automatic real-time interaction by the master processor for stepping through a set of tests in a test room, and printing labels for laboratory samples in a test room.

FIG. 23, illustrating Test Room Sequence and Labeling Test Samples for Laboratory, shows a short-hand flow chart of how once the "Next Test" function key is selected at the P/C processor in a test room, the Master Processor 101 automatically in real-time maintains the testing sequence and print labels for laboratory samples. As shown in block 2302, test results for the test just completed are transferred to Long Term Memory 106.

The known events indicated by blocks 2301, 2303, and 2304 are the "Next Test" input from the technician, the technician I.D. code input, and the patient I.D. input, respectively. Interaction takes place between these inputs as indicated by block 2305 which starts a sequence of events to determine the unknown: which test is next and if a label for a laboratory sample is needed.

Instructions for the next test are displayed (block 2306) at the P/C processor for the technician. If the next test requires a laboratory sample, the label for the sample will automatically be printed as shown in blocks 2307 and 2308. If the next test is not a laboratory sample, block 2308 is skipped. If this test turns out to be the last test, the patient is instructed to proceed back to the diagnosis room as shown in blocks 2309 and 2310 for check-out diagnosis. Since check-out diagnosis is performed with the same nurse and room as check-in diagnosis, the original diagnostic room is obtained from Long Term Memory 106 at block 2310 and included in the instructions displayed on the wall display in the test room for the patient (block 2311). Block 2312 ends the sequence of events.

Reference is made to FIG. 17 (note that FIGS. 16 and 17 are interconnected by continuation labels H, J, K, and L).

The technician will affix each label to the container with each sample and pass this into the laboratory. The passing of the sample into the laboratory through an access door provides an input 1735 to Master Processor 101 signalling that the sample has entered the Lab. Master Processor 101 automatically receives the input showing a sample passing through an access door from the test room into the laboratory.

Sample Program

Figure 24:
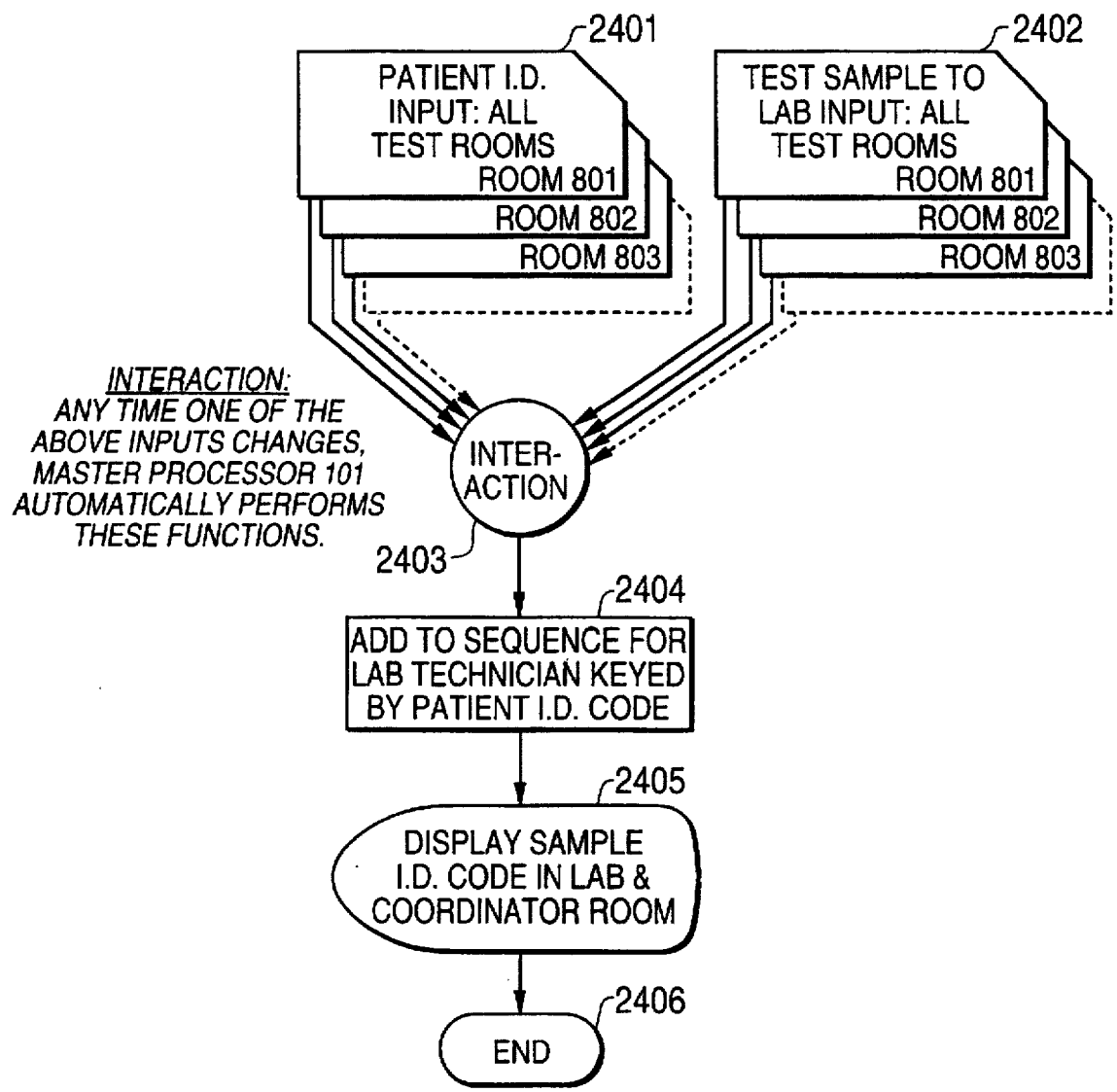
FIG. 24 shows automatic real-time interaction by the master processor when samples are passed from the test rooms to the lab.

FIG. 24, illustrating Sample from test room to Lab, shows a short-hand flow chart of how anytime a sample passes into the laboratory from a test room, the Master Processor 101 automatically in real-time updates the sequence for the laboratory technician.

The known events indicated by blocks 2401 and 2402 are the patient I.D. input at the test room the sample originated from and the input of the sample physically being passed into the laboratory. Interaction takes place between these inputs as indicated by block 2403 which starts a sequence of events to determine the unknown: to add the sample to the sequence of samples to be analyzed in the laboratory.

The Sample at block 2404 is added to the list of samples already in the laboratory. The sequence is in the order the samples were received. At block 2405 the laboratory technician is alerted that a sample has entered the laboratory for processing. Patient information and instructions on what to do with the sample are displayed in the laboratory for the laboratory technician as well. The coordinator status display at block 2405 is also updated regarding the location and status of the sample(s) belonging to this patient I.D. Block 2406 ends the sequence of events.

Reference is made back to FIG. 17 again (note that FIGS. 16 and 17 are interconnected by continuation labels H, J, K, and L) As the Master Processor 101 automatically displays on the coordinator room wall display which samples are in the laboratory, the Master Processor 101 also displays the tests 1741 on the laboratory display, and sends the testing information 1741 and sequence 1742 down to the laboratory P/C processor for the patient I.D. As the laboratory technician performs the tests on the samples, the laboratory technician uses the function keys at the laboratory P/C to acknowledge the completion of each test. This is provided as an input 1743—the current sequence—to the Master Processor 101 by the P/C processor in the laboratory. Upon completion of all tests, the laboratory P/C processor provides all test results 1744 as an input to the Master Processor 101. The Master Processor 101 automatically updates the patient history in Long Term Memory 106 with these laboratory test results.

Diagnostic Room (Check-Out)

Reference is made back to FIG. 16—"Coordinator, Diagnostic, In/Out Room and Pharmacy Information Flow Management". Upon arrival at the diagnostic room, the patient inserts the I.D. card and the I.D. card input is automatically received by the Master Processor 101. The Master Processor 101 transmits the test results 1607 to the P/C processor in the diagnostic room and displays the results on the wall display, the Master Processor 101 also automatically displays that the patient is present in the diagnostic room on the display in the coordinator room.

The diagnostic nurse makes a final diagnosis and enters it into the P/C processor. The P/C processor provides this final diagnosis 1604 automatically as an input to the Master Processor 101. The Master Processor 101 automatically adds this as part of the patient's history in Long Term Memory 106. If the final diagnosis 1604 includes a prescription, the P/C processor in the diagnostic room provides the prescription information 1605 as an input to the Master Processor 101. The Master Processor 101 automatically outputs the prescription information 1621 to the P/C processor in the pharmacy and automatically displays the patient I.D. and required prescription on the wall display in the pharmacy. The pharmacy P/C processor upon receipt of the prescription input from the Master Processor 101 automatically prints the label for the prescription container. The pharmacist will now fill the prescription.

Sample Program

Figure 25:
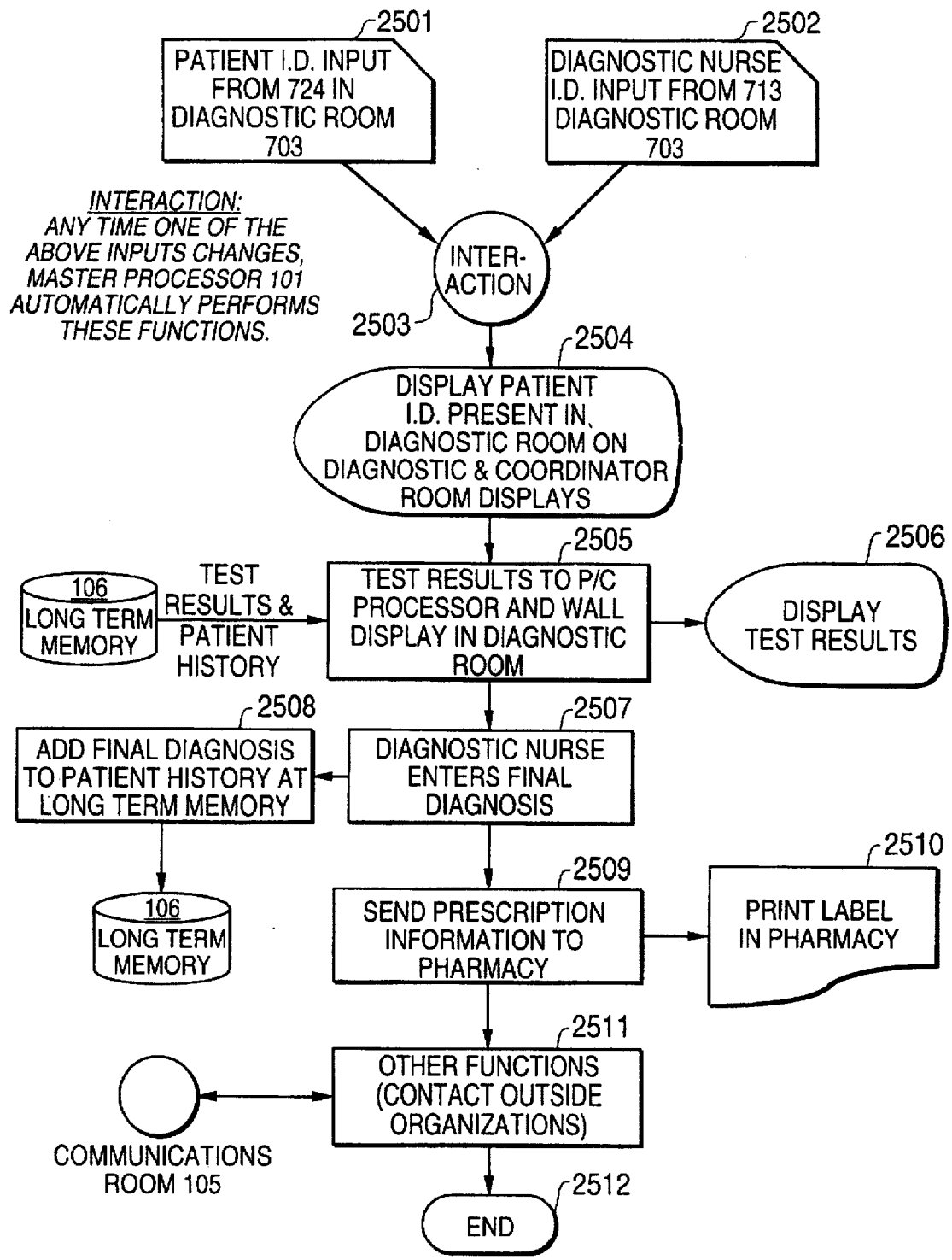
FIG. 25 shows automatic real-time interaction by the master processor when the patient returns to the diagnostic room from a test room, and the I.D. card input is received.

FIG. 25, illustrating Patient Returns to Diagnostic Room from test room, shows a short-hand flow chart of how once the Patient I.D. input is received for check-out diagnosis, the Master Processor 101 automatically in real-time starts a sequence of events to manage the completion of diagnosis.

The known events indicated by blocks 2501 and 2502 are the patient I.D. input and the diagnostic nurse I.D. input, respectively. It is also known that the patient is here for check-out diagnosis (as opposed to check-in diagnosis). Interaction takes place between these inputs as indicated by block 2503 which starts a sequence of events to determine the unknown: a final diagnosis.

At blocks 2504 and 2505 the wall displays in coordinator and diagnosis rooms are updated with the current patient I.D., and test results are obtained from the Long term Memory 106 for the diagnostic nurse at the P/C processor in the Diagnosis Room. Test results are also displayed on the wall display (block 2506) in the diagnostic room for the patient. At block 2507 menus are used by the nurse at the P/C processor to enter the final diagnosis and needed prescriptions which are then stored in the Long Term Memory 106 by block 2508. Prescription information is also sent to—and printed at—the pharmacy by blocks 2509 and 2510. At block 2511 the nurse may interact with the management system to answer any questions the patient may have including referrals to outside organizations via the communications room 105. Block 2512 ends the sequence of events.

Upon completion of the diagnosis, the patient may request a running history of test results covering results of past visits and the day's visit. For this the diagnosis nurse selects the "history" function key at the P/C processor. Reference is made to FIG. 20, showing Diagnostic Room Functions at P/C Processor, for function keys the diagnostic nurse uses. The P/C processor requests the patient's history as an input to the Master Processor 101. The Master Processor 101 automatically outputs the patient's history from Long Term Memory 106 to the P/C processor in the diagnostic room, where it is automatically printed out for the patient.

If the diagnostic nurse decides the patient should be referred outside the clinic, this is done immediately through the diagnostic room with the nurse selecting the "Specialist/Doctor's Opinion" function key at the P/C processor. Reference is made back to FIG. 16, showing Information Flow Management. The diagnostic room P/C processor provides the request as input 1606 to the Master Processor 101. The Master Processor 101 automatically outputs this request to the communications room 105. Once contact is established in the communications room, the diagnostic nurse is contacted by phone or alerted by Master Processor 101 on screen via the P/C processor, and Master Processor 101 automatically transmits the patient's history (including the day's test results and diagnosis) from the Long Term Memory 106, across the communications link the communications room 105 has established. In this manner, the person conversing via the phone with the diagnostic nurse also has all the patient information for review in real time.

Diagnosis is now complete. The Master Processor 101 automatically displays the next room 1602 to which the patient should proceed on the wall display in the diagnostic room. If the patient needs to pick-up a prescription, the displayed room will be the pharmacy, otherwise the coordinator room will be displayed.

Assuming the patient must pick up a prescription upon extraction of the patient I.D. card from the diagnostic room, the Master Processor 101 automatically displays on the coordinator and selected pharmacy displays that the patient is en route to the selected pharmacy. The patient then walks from the diagnostic room to the selected pharmacy.

Pharmacy

Reference is made to FIG. 16, showing Information Flow Management.

Upon arrival at the pharmacy, the patient inserts the I.D. card and the I.D. card input is automatically received by the Master Processor 101. The Master Processor 101 automatically displays the patient as present in the pharmacy on both the coordinator and pharmacy displays. After the pharmacist fills the prescription, a "done" function is selected by the Pharmacist at the pharmacy P/C processor. The pharmacy P/C processor provides this automatically as an input 1623—prescription filled—to Master Processor 101. The Master Processor 101 then automatically determines the next room 1622, which in this case will be the checkout window in the coordinator room, and automatically displays this on the wall display in the pharmacy. The pharmacist explains the information on the prescription label to the patient and instructs the patient to proceed to the coordinator room.

Upon extraction of the patient I.D. card from the pharmacy, the Master Processor 101 automatically displays on the coordinator wall display that the patient is en route to the coordinator room check-out window. The patient now walks from the pharmacy to the coordinator room.

Coordinator Check-out Window

As soon as the patient leaves the pharmacy by extracting the patient I.D. card, the Master Processor 101 automatically prints out a visit summary for the patient via the P/C processor in the coordinator room. The Master Processor 101 automatically uses billing information and visit summary data all accumulated during the patient's visit from Long Term Memory 106. The Master Processor 101 automatically invoices the insurer as well via communications links in the communications room 105.

Sample Program

Figure 26:
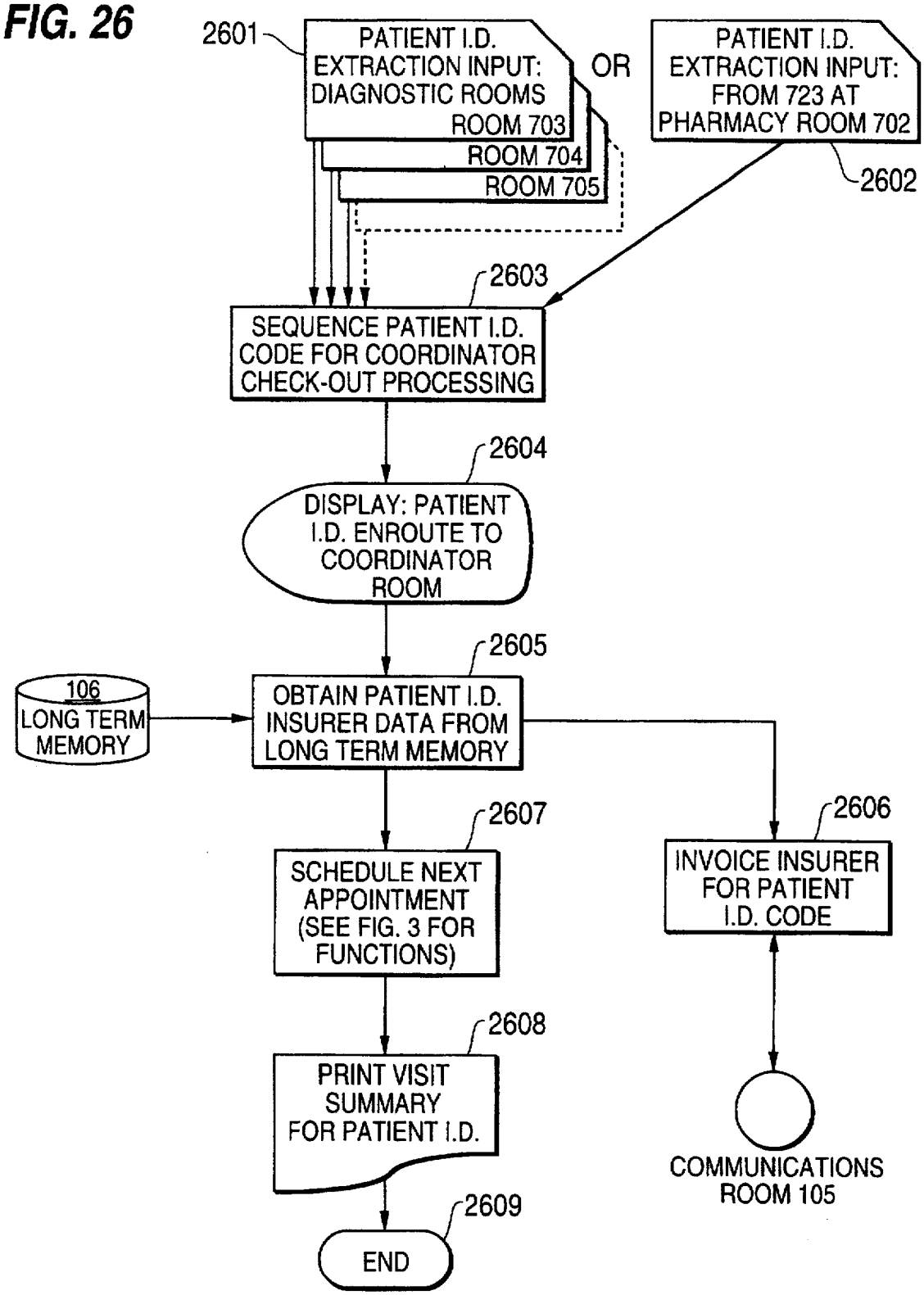
FIG. 26 shows automatic real-time interaction by the master processor for preparation of the visit summary and invoicing of the patient's insurer.

FIG. 26, illustrating Prepare Visit Summary and Invoice Insurer, shows a short-hand flow chart of how anytime a patient prepares to proceed to the coordinator check-out counter, the Master Processor 101 automatically in real-time invoices the insurer and prints a visit summary in the coordinator room.

The known events indicated by blocks 2601 and 2602 are the patient I.D. extraction input from any diagnosis room upon completion of check-out diagnosis, or the patient I.D. extraction input from the pharmacy.

As soon as any one of these inputs is received the sequence of events for that patient I.D. for coordinator check-out processing starts (block 2603). The coordinator wall display is updated indicating the patient I.D. is en route at block 2604. At block 2605 the patient's insurer data is obtained from the Long Term Memory 106 and passed on to the communications room resources in block 2606 where the insurer is invoiced. Next, the coordinator pulls up the appointment scheduling display at the P/C processor. When the patient arrives at the coordinator check-out window the next appointment is scheduled with the patient (block 2607) and the visit summary for the patient is printed (block 2608). The sequence of events stops at block 2609.

Upon entry into the coordinator room, the patient inserts the patient I.D. into the card reader at the coordinator check-out window. Master Processor 101 now automatically displays the patient as present in the coordinator room on the wall display in the coordinator room. The coordinator goes over the printed visit summary with the patient and schedules the next appointment via the coordinator room P/C processor. See FIG. 3 for function keys the coordinator uses for appointment scheduling. The Master Processor 101 automatically updates the appointment calendar as an output to Long Term Memory 106. See the "Registration/ Appointments" section in the communications room description for details on appointment scheduling.

Upon extraction of the patient I.D. card from the coordinator check-out position in the coordinator room, the Master Processor 101 automatically clears the patient I.D. off the coordinator display, and the patient leaves the clinic.

4. Building Design

The electronic automatic real-time interaction management system can be implemented into any clinic, hospital or business. A building (clinic or hospital) can also be specifically designed for the electronic management system so that the instructions from the management system can uniquely control all operations, patients and employees while distance travelled and flow through the clinic is as short, simple and efficient as possible.

In order to facilitate employees and patients following the automatic instructions from start to finish, the building can be designed so that the employees work in a controlled room and the patients take as few steps as possible while they are in the clinic.

Figure 27:
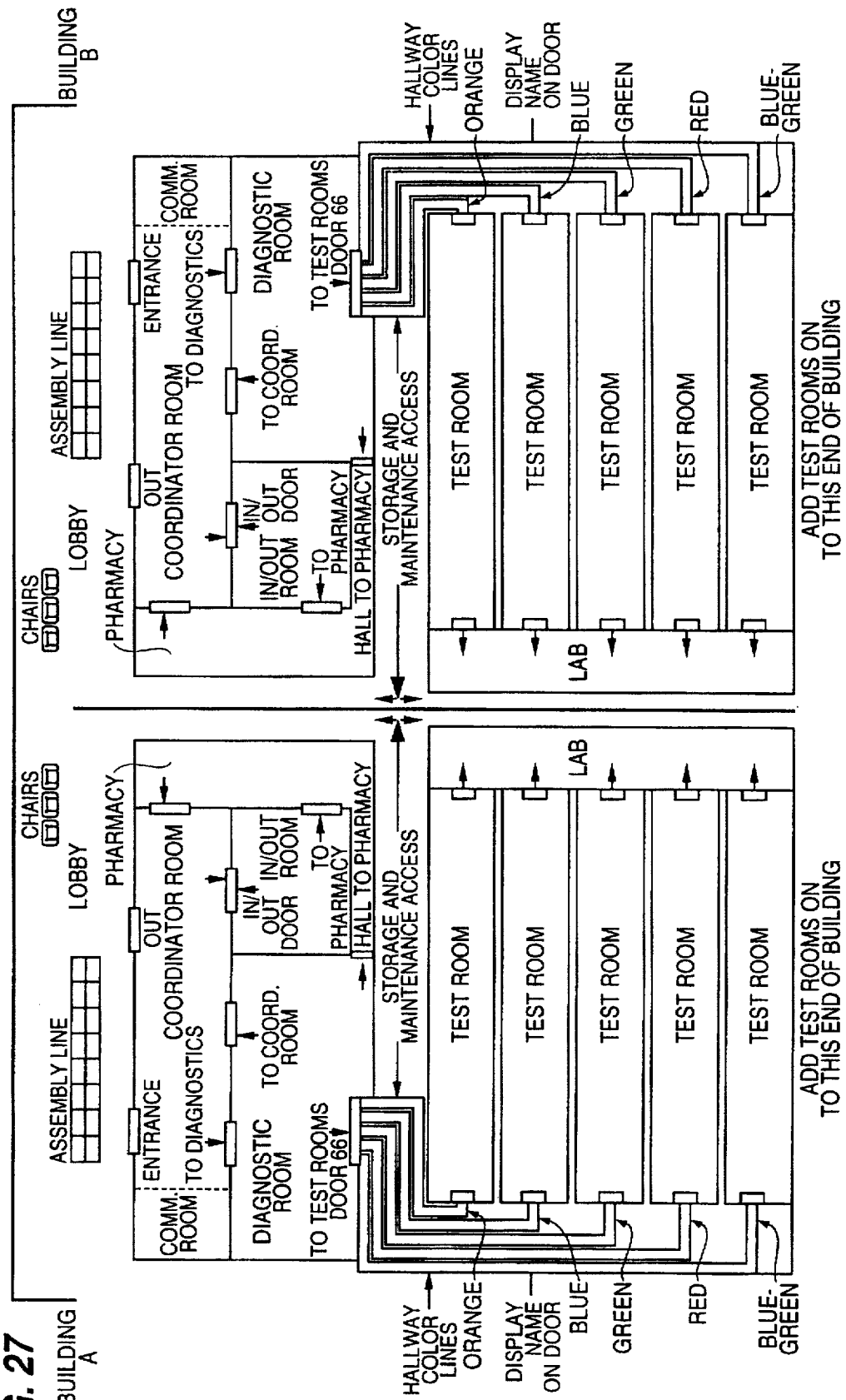
FIG. 27 is a layout of the clinic building showing all rooms and the lobby.

FIG. 27, illustrating a Clinic Layout, shows how all the rooms are laid out in relation to each other for one embodiment of an efficient design. The patient is instructed to proceed to a diagnostic room where all tests are decided upon, a test room where all tests are performed in the same room, back to the same diagnostic room for diagnosis and conclusions, on to the pharmacy for pick up of medication and back to the same coordinator room for a copy of the diagnosis, all tests, and insurance company billing with verification of payment.

The clinic layout, in combination with the management system, provides a completed physical, diagnosis, prescription service, invoicing, and handling of insurance with no paper work involved; and only a few hundred feet of travel inside the clinic with no confusion on where to go and what to do next.

4.1 Patient Flow through Building

The clinic building must be designed so that the patient is controlled efficiently where the patient has few steps to go to the prescribed rooms and where the rooms are on the same floor. As part of the design, hallways have one way traffic wherever possible, to make sure the patient goes in the right direction, and colored lines that the patients can follow to rooms with doors of the same colors.

Reference is made to FIG. 27, illustrating an embodiment of a Clinic Layout. The lobby of the clinic is where patients will wait before the coordinator calls them in. It is a simple room with rest rooms and an entrance to the coordinator room. The patients can either go to the rest room or enter the clinic via the coordinator room.

Figure 28:
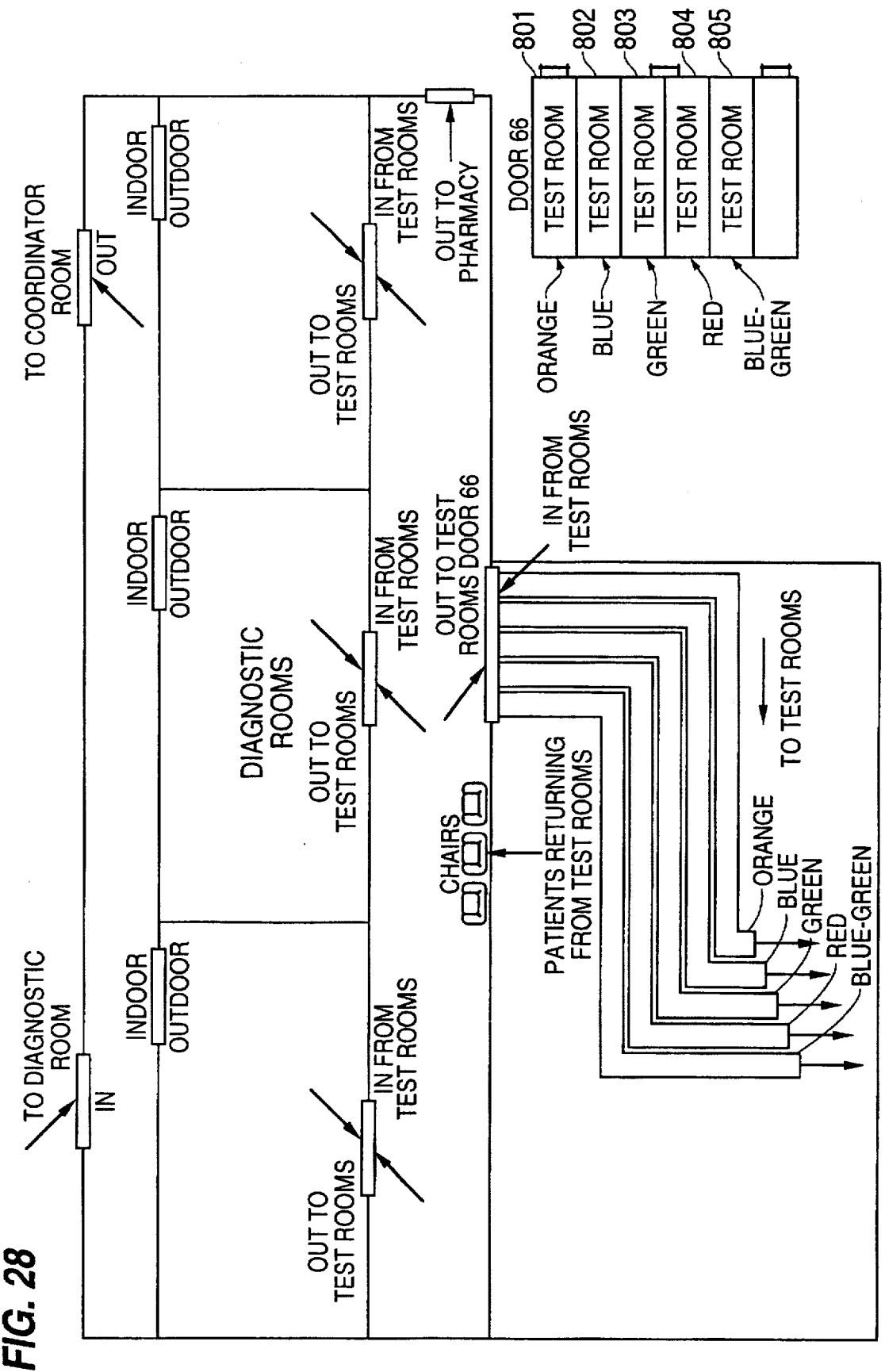
FIG. 28 is a building layout of the diagnostic rooms and hallways to the test rooms.

The building aids the patient flow through signs and color markings, referred to as patient flow indicators. If instructed at the coordinator room to proceed to diagnostic room 703, the patient goes through the single brown door from the coordinator room to the diagnostic room. Above the brown door is a sign displaying "To Diagnostic Room". Reference is made to FIG. 28, Diagnostic to Test Room Layout. The patient proceeds to room 703 where the patient's name is displayed at the door electronically.

If tests have been decided upon, the diagnostic nurse instructs the patient to proceed to test room 801. The patient walks up to a door 66 marked with all the Test room numbers and colors (test room 801 is marked in orange). The patient goes through the door and follows the orange line on the hallway floor to test room 801 (see FIG. 27). At the end of the orange line is a sign advantageously stating "Test Room 801 Enter". The patient's name is displayed at test room 801 electronically, as well. All testing and sampling is performed in this test room. Each Test room also has a rest room so that the patient does not have to leave the test room until all tests are completed.

Once the tests are completed, the patient is instructed to proceed back to the same diagnostic room 703 by following the orange line back from the test room 801 to the diagnostic room. At the end of the orange line is a sign advantageously stating "Diagnostic Room Enter". The patient's name will be displayed at diagnostic room 703. If the diagnostic nurse is busy, the patient will wait in the seating area right outside room 703.

After the session with the diagnostic nurse, the patient may be instructed to proceed back to the coordinator room through the pink door advantageously marked "To Coordinator Room" or through the yellow door to the pharmacy if medication was prescribed. If the patient takes the yellow door advantageously marked "Out to Pharmacy", (FIG. 27 shows clinic layout), the patient takes a one-way yellow hallway into the pharmacy, where medication is picked up. From the pharmacy the patient is instructed to proceed to the coordinator room through the pink door marked "To Coordinator Room".

Once all invoicing and paperwork have been taken care of, the patient takes the door advantageously marked "Lobby" to exit the coordinator room.

4.2 Modularity and Expansion

The building design is modular and can be expanded simply and economically in two ways as shown on FIG. 27, illustrating a Clinic Layout.

First of all, test rooms can be added to the existing test rooms. All test rooms are preferably adjacent to each other.

A test room would be added as a module. The other rooms are sufficient to handle a reasonable addition of test rooms, as is the capacity of the electronic management system in the clinic.

Secondly, the entire facility could be expanded when the addition of test rooms has reached a point of saturation of the work load in the coordinator and diagnostic rooms. A second duplicate building "B" can be added to the original building "A", and attached together they now form an expanded clinic.

The second building "B", once joined to the first building "A", is a completely independent clinic in employees, rooms and equipment and handles all its patients independently from the first building "A". Maximum efficiency is maintained in this way since the system in place in each building is not disrupted. Confusion, tension, wasted time and mistakes are also minimized by keeping the patients and employees in the same building.

4.3 Assembly Line System

FIG. 27, illustrating a Clinic Layout, shows an area in the Lobby termed "Assembly Line". These are preferably portable cubicles that can be temporarily moved into place to handle a large number of people for the same quick treatment such as flu shots.

Depending on the demand, the cubicles can be added with a clinic employee in each cubicle. In this manner, the normal flow of patients through the clinic and the activities in the other clinic rooms are not affected by this type of service. A test or diagnostic room could be dedicated to this type of service as well, but they would still not interfere with the normal flow of patients through the clinic.

5. Automatic Interaction

Automatic Real-Time Dynamic Interaction as related to clinic and its automatic interaction management system.

Throughout the clinic, real-time signals are received from I.D. card readers. The real-time signal is automatically sent to a specific group of events. The specific group is determined by the location of the I.D. card reader in the network at the clinic. Each I.D. card reader has two different real-time signals, each one (card in/card out) automatically selects a different group of events and triggers the group's interaction.

The dynamic interaction is a comparison in real-time of all the events in that specific group.

The dynamic interaction of the group of events is what automatically generates the outputs of that group in real-time.

If one of the events in the group does not take place, the interaction ceases and the outputs will not be generated.

For example:

Take the real-time interaction that takes place among a group of three events as the patient I.D. card input is received at the coordinator check-in position.

| Trigger | Patient I.D. Card Input | | |
|---|---|---|---|
| Event | Event 1: | Event 2: | Event 3: |
| | I.D. card Input at coordinator (real-time input) | Verify appointment in memory (historical input) | Verify insurance via communications link (real-time input) |
| Output | Real-Time Outputs: 1. Patient name, reason for visiting 2. Scheduled time slot 3. Insurance O.K. 4. O.K. to proceed | | |

The I.D. card input triggers the interaction to take place between the three events in the interaction group. In this example, outputs will not be generated if any of the events in the interaction group do not take place (if, for example, no appointment was made). Note that the inputs for the events in one group may be a combination of real-time and historical inputs.

Another example:

Following is the real-time interaction that takes place for selecting the diagnostic room right after the patient checks in with the coordinator.

| Trigger | O.K. to proceed past coordinator check-in (output from previous interaction) | | | | |
|---|---|---|---|---|---|
| Event | Event 1: | Event 2: | Event 3: | Event 4: | Event 5 |
| | O.K to proceed (R/T) | clinic size (historic) | # patients at clinic (R/T) | All patient I.D. readers @ diagnostic rooms (R/T) | All nurse I.D. readers @ diagnostic Rooms (R/T) |
| Output | Real Time Outputs: 1. Selected Diagnostic Room 2. Patient history to selected diagnostic room processor 3. What diagnostic person to see (name) | | | | |

Besides I.D. card readers, other sources of real time inputs are:

Equipment signalling test completion or results;

Employee selecting "done" during diagnosis or test functions; and/or

Signal from outside the clinic via communications equipment for automatic appointment scheduling, patient data, insurance verification, etc.

All these real-time signals also have their own interaction groups set up. The master processor is programmed with each interaction group and thus senses many groups of real-time inputs that relate to the automatic management of patient flow, employee flow, and patient information flow. The advantage is that instant up-to-the moment information, at least to human perception, is provided.

6. Simulation Test

A simulation test using one embodiment was conducted. To compare the effect in workload, the number of human interventions required for each major patient activity was counted. This was compared with a simulation of the same activity in a conventional clinic. Table 1 summarizes the number of human interventions and patient trips required.

TABLE 1

| | Required human interventions | |
|---|---|---|
| Patient Activity | Conventional Clinic | Real-Time Clinic |
| 1. Patient makes appointment with clinic | 10 | 5 |
| 2. Patient receives examination | 27 | 3 |
| 3. Patient receives tests. | 22 | 1 |
| 4. Patient receives results and diagnosis | 24 | 9 |
| 5. Patient receives prescription | 1 | 0 |
| Total human interventions | 84 | 18 |
| Total patient trips | 4 | 1 |

From the results observed during the simulation, the effect of the real-time clinic is anticipated to be a 75% reduction in workload.

Table 2 shows the events for the simulation test during each patient activity and the actions taken at the clinic including human interventions and actions taken by the real-time system.

TABLE 2

| EVENT | Conventional Clinic | Real-Time Clinic |
|---|---|---|
| Patient calls for appointment. | Human contact. | Human contact. |
| Patient provides reason for appointment | Clinic personnel: write information. | Clinic personnel: input to system. |
| Clinic and patient set appointment | Clinic personnel: check appointment book. give choice of times. write agreed upon time. | Output available times. Clinic personnel: give choice of times. input to system. |
| Patient gives insurance information | Clinic personnel: write information. check patient files now or later. verify employment. call insurance company to verify coverage. | Clinic personnel: Input to system. |
| (If insurance a problem, call patient back to discuss). | Clinic personnel: contact to employer and/or patient and continues until everything is cleared. | Automatic |
| Patient arrives at clinic for appointment. | Patient: Fills out forms. Clinic personnel: verify appointment. pull patient file. information reviewed. update files. Put files in appropriate location. | Clinic personnel: Scan patient I.D. card. |
| Patient waits to go to diagnostic room | Clinic personnel: check on availability of needed medical personnel. check on availability of examining room. take files to appropriate location. Medical personnel: pick up file. | Automatic |
| Patient in diagnostic room. | Medical personnel: do examination. write information into patient record. May be entered into software later. order tests. Clinic personnel: pick up file. phone orders to test site. record information for billing. | Medical personnel: do examination. input to system. |
| Patient finishes interview. | Clinical personnel: finish paperwork. call test site for appointment. confer with patient on time slots. set appointment for test site. give insurance information to test site. compute insurance coverage. prepare patient billing. collect from patient. prepare billing to insurance company. | Automatic |
| Prepare patient for tests. | Test site personnel: previously verified insurance coverage. previously verified employment. verify appointment. have patient fill out forms. | Automatic Patient walks to test rooms. |
| Patient waits to go to test room. | Clinic personnel: prepare files. place files in proper location. verify locations of test site personnel. verify room availability. prepare files. | Automatic |

TABLE 2-continued

| EVENT | Conventional Clinic | Real-Time Clinic |
|---|---|---|
| | place files in proper location. | |
| Tests performed. | Test site personnel: track test progress. track patient location. track clinic test personnel. track lab personnel. track lab samples. enters patient information | Automatic |
| Test finished. | Test site personnel: Enter results into patient records. Phone or send patient information to referring clinic | Clinic test personnel: input to system |
| Finish test. | Test site personnel: enter information into patient files. compute charges. collect from patient. prepare insurance billing. | Automatic |
| Patient returns for review of test results. | Clinic personnel: verify appointment. pull patient files. review information. verify information. update file. put file in appropriate location. Medical personnel: pick up file. | Automatic Patient walks back into the examining room. |
| Patient enters diagnostic room. | Medical personnel: explains results. diagnoses. treatment. prescribes. Clinic personnel: Put information into patient file. Check that everything is there. File patient records. Mail or call information to appropriate practitioners. | Medical personnel: explains results. diagnoses. treatment. prescribes. input to system. |
| Patient goes to front desk. | Clinic personnel: update patient records. prepare billing. compute insurance coverage. compute patient charges. file patient records. bill insurance company. collect for charges. | Clinic personnel: collect for charges. provide prescriptions to patient. |
| Schedules next appointment | Clinic personnel: review appointment records. Patient: selects time. | Clinic personnel: Ask system for times. Patient: selects time. |
| Patient travels to pharmacy. | Patient picks up prescription. | Automatic. |

7. Comparators

Interaction groups have inputs which can be of a real-time or historical nature. The value of a real-time input may change over time, from second to second, minute to minute and is continuously received. The value of a historical input does not change over time. Its value is constant. It was recorded previously or entered manually into long-term memory.

Comparators are inputs into interaction groups whose values are held constant over time so that they can be used as reference points for detecting change. In many of the clinic interaction groups, comparators are used and are usually historical in nature. Examples of historical comparators are clinic capacity, overhead costs per hour, and previously recorded patient test results. However, a comparator can be a real-time input as well. All that is required is that the value of the comparator be held constant for the duration of the real-time interaction.

For example: CLINIC CAPACITY used as a comparator. In Part 5. Automatic Interaction, discussed above, there is a sample interaction for selecting the diagnostic room right after the patient checks in with the coordinator. The unknown factor for the coordinator is this: A decision must be made as to whether or not the patient should be allowed past the coordinator, and if so, to which room should the patient be sent.

The selection of the diagnostic room depends on whether or not the clinic is currently at capacity. The capacity of the clinic does not change over time and is kept as a historical aspect of the clinic building in long-term memory. The current number of patients throughout the clinic is then compared to this clinic capacity. The figure in Part 5. shows all the inputs. Also see FIG. 19 and section 3.5 "Sample Program" under Selecting a Diagnostic Room.

As shown in FIG. 19, one real-time input is used to ensure that insurance is verified, three other real-time inputs are used (patients en-route, patients in rooms, and location of diagnostic nurses) to determine how many patients are currently in the clinic. The clinic capacity is then used as a comparator to the total number of patients. If the value of the comparator (the clinic capacity) exceeds the total number of patients in the clinic, another patient can be sent in. Next, the logic for selecting a diagnostic room is executed and the unknown factor now becomes a known factor for the coordinator; the coordinator will either be instructed to tell the patient to wait in the lobby, or to continue on to a specific diagnostic room.

Interaction is always in real-time. The interaction takes place in real-time, even though the inputs to the interaction group may have some real-time and some historical inputs and some of these may be comparators. Similarly, the output values are generated automatically in real-time, whether or not the interaction group contains historical inputs.

Other examples:

Finances: Comparators are used in the automatic generation of a profit and loss statement for the clinic owner. The overhead costs per hour, day, and week are compared against the business or monies generated as the clinic operates. This allows real-time reporting of profit-loss statements.

Test Results: Patients can have their test results compared to historical data. For example, test results such as sugar level, blood pressure, etc., can be compared to the results of the patient's previous tests. The amount of change may be important if one is looking for improvement or tracking a certain illness.

What is unique about the outputs and the methods by which comparators are used? The outputs from the management system turn unknown factors into known factors for the clinic employees and patients. If this involves comparators, the required comparisons are also done automatically.

No one has to keep track of who is where, why, and when, no one needs to worry about how many patients you are supposed to be able to handle, and no information needs to be pulled out and looked at to use these comparators. No one needs to look at last month's financial statements and calculate if you are doing better or worse. No one needs to total income at the end of the day and pull cost information out. The interaction management system is using these comparators automatically in real-time, and automatically makes the decisions with these comparators for the clinic employees.

With the use of comparators, unknown factors such as profit/loss, decisions on keeping patients flowing without overflowing the clinic, and past test results to track illness over time are all turned automatically in real-time into known factors—information that can be used on the spot without any manual labor for generating that information.

While specific embodiments of the invention have been described and illustrated, it will be clear that variations in the details of the embodiments specifically illustrated and described may be made without departing from the true spirit and scope of the invention as defined in the appended claims and equivalents thereof. For example, different levels of trained personnel may be located in the various rooms, depending on requirements set by the specific facility, state regulations, and so forth.

What is claimed is:

1. A dynamic real-time interactive management system for use in management and operation of a facility and management of a plurality of persons relative to said facility, said plurality of persons including a first plurality of persons who are employees of said facility and a second plurality of persons who are customers utilizing said facility, comprising:

(a) a master processor for continuously and automatically receiving a plurality of sensed real-time inputs related to said facility and a plurality of persons relative to said facility, said master processor also receiving a plurality of operator-entered inputs related to said facility and locations of said plurality of persons inside said facility;

(b) a memory linked to said master processor, for storing sensed values of said sensed real-time inputs and for storing a plurality of programs for defining relationships between certain ones of said sensed real-time inputs; and (c) a display connected to said master processor, said display for producing a humanly perceivable signal; wherein (d) said master processor includes means for continuously and automatically determining in real-time interactions and relationships between said sensed real-time inputs using said plurality of stored programs, means for continuously and automatically producing an interaction indication result for identifying a first set of desired locations for said second plurality of persons inside said facility to provide assistance to said first plurality of persons based on said sensed real-time inputs, means for continuously and automatically producing a condition output which is indicative of a relationship between said sensed values and said interaction indication result, and means for automatically transmitting said condition output to said display, said condition output identifying a second set of desired locations to which said first plurality of persons are to go to inside said facility.

2. The system of claim 1 wherein said means for continuously and automatically producing a condition output includes means for continuously and automatically producing a plurality of condition outputs which are indicative of relationships between sensed real-time inputs and interaction indication results, the system further comprising a terminal connected to said master processor for selecting a desired condition output to be transmitted to said display.

3. The system of claim 2, wherein said terminal includes means for inputting management information into said master processor and wherein said master processor includes means for utilizing said management information with said sensed values as input data for said plurality of programs so as to produce said interaction indication result and said condition output.

4. The system of claim 3, further comprising a plurality of I.D. card readers that communicate with said master processor, said I.D. card readers configured to sense I.D. card codes inputted thereto by said plurality of persons and to transmit said sensed I.D. card codes as said sensed real-time inputs to said master processor, said sensed I.D. card codes including information related to identification of said plurality of persons for use in retrieving stored information associated with said plurality of persons from said memory, wherein a first case in which an I.D. card code of one of said second plurality of persons is sensed by one of said I.D. card readers at a first location within said facility results in a different interaction indication result than a second case in which said I.D. card code of said one of said second plurality of persons is sensed by another of said I.D. card readers at a second location within said facility that is different from said first location.

5. The system of claim 4, wherein said display includes a plurality of patient flow indicators for indicating a patient flow between a plurality of predetermined rooms and wherein said condition output includes patient flow information.

6. The system of claim 5, further comprising patient test equipment that communicates with said master processor, said patient test equipment for sensing patient test data and transmitting said patient test data as said sensed real-time inputs to said master processor.

7. The system of claim 6, wherein said patient test equipment is located in one of said predetermined rooms.

8. The system of claim 5, further comprising at least one personal computer processor which communicates with said master processor, said at least one personal computer processor for transmitting a plurality of manual inputs to said master processor.

9. The system of claim 8, wherein each personal computer processor is located in one of said predetermined rooms.

10. The system of claim 8, wherein said plurality of manual inputs and said condition output are stored in said memory as historical aspects and wherein said master processor includes means for selectively interacting said historical aspects with said real-time inputs to produce interaction indication results.

11. The system of claim 8, wherein said manual inputs are directly input to said master processor via respective communication channels connecting said at least one personal computer with said master processor, wherein said manual inputs include information related to patient historical aspects, equipment maintenance information, information related to employee schedules and rosters, inventory information, information related to costs, and facility characteristics information.

12. The system of claim 8, wherein said real-time inputs include inputs that originate external to the facility.

13. The system of claim 5, wherein each I.D. card reader is located in one of said predetermined rooms.

14. The system of claim 2, further comprising a second master processor at a location separate from said facility, a network processor and a communications link connected to said network processor, said master processor and said second master processor to each other, said network processor for transmitting information between said master processor at said facility and said second master processor at said location separate from said facility.

15. The system of claim 1, wherein said facility is a medical facility for treatment of patients, and said persons include patients and facility employees.

16. The system of claim 1, wherein said sensed real-time inputs are directly input to said master processor via a communication channel connecting at least one personal computer to said master processor, wherein said sensed real-time inputs include sensed I.D. card codes which include information related to identification of users of said sensed I.D. card codes for use in retrieving stored information associated with said users from said memory, sensed selected test information, sensed test result information, final diagnosis information, prescription confirmation information, insurance verification information, standardized testing program information, health maintenance program information, patient appointment information, and requests for patient data exchange information.

17. The system of claim 16, wherein said condition output includes patient data and history information, an employee instruction, an insurer invoice, an appointment schedule, an employee duty roster, a maintenance schedule, an inventory requirement, a visit summary, an insurer approval notification, a patient referral, and a profit and loss statement for said facility.

18. The system of claim 16, wherein said condition output includes patient data and history information.

19. The system of claim 16, wherein said condition output includes an employee instruction.

20. The system of claim 16, wherein said condition output includes an insurer invoice.

21. The system of claim 16, wherein said condition output includes an appointment schedule.

22. The system of claim 16, wherein said condition output includes an employee duty roster.

23. The system of claim 16, wherein said condition output includes a maintenance schedule.

24. The system of claim 16, wherein said condition output includes an inventory requirement.

25. The system of claim 16, wherein said condition output includes a visit summary.

26. The system of claim 16, wherein said condition output includes an insurer approval notification.

27. The system of claim 16, wherein said condition output includes a patient referral.

28. The system of claim 16, wherein said condition output includes a profit and loss statement for said facility.

29. The system of claim 1, wherein said means for continuously and automatically determining in real-time interactions and relationships between said real-time inputs using said plurality of stored programs includes means for commanding certain of said real-time inputs to be held constant to act as comparators in order to sense changes in other of said real-time inputs.

30. The system of claim 1, wherein said real-time inputs, said interaction indication result, and said condition output relate to patient information thereby automatically managing patient information flow.

31. The system of claim 1, wherein said condition output includes an automatic instruction to a lab room for indicating a priority of tests to be analyzed.

32. A method of providing dynamic real-time interactions for use in management and operation of a facility and a plurality of persons related to said facility, said plurality of persons including a first plurality of persons who are employees of said facility and a second plurality of persons who are customers utilizing said facility, the method comprising the steps of:

(a) continuously and automatically receiving, in a master processor, a plurality of sensed real-time inputs related to said facility and a plurality of persons relative to said facility, said master processor also receiving a plurality of operator-entered inputs related to said facility and locations of said plurality of persons inside said facility;

(b) storing sensed values of said real-time inputs in a memory linked to said master processor;

(c) continuously and automatically determining in real-time interactions and relationships between said real-time inputs using a plurality of programs stored in said memory;

(d) continuously and automatically producing an interaction indication result for identifying a first set of desired locations for said second plurality of persons inside said facility to provide assistance to said first plurality of persons based on said real-time inputs;

(e) continuously and automatically producing a condition output which is indicative of relationships between said sensed values and said interaction indication result;

(f) automatically transmitting said condition output to a display connected to said master processor, said condition output identifying a second set of desired locations to which said first plurality of persons are to go to inside said facility; and (g) producing a humanly perceivable signal in said display.

33. The method of claim 32, further comprising the step of inputting management information into said master processor and interacting said management information with said sensed values.

34. The method of claim 32, wherein the step (e) includes continuously and automatically producing a plurality of condition outputs which are indicative of relationships between sensed values and interaction indication results, the method further comprising the step of selecting a desired condition output to be transmitted to said display.

35. The method of claim 32, further comprising the step of sensing an I.D. card code in an I.D. card reader and transmitting said sensed I.D. card code as a sensed real-time input to said master processor, said I.D. card code being inputted to said I.D. card reader by one of said plurality of persons, wherein said sensed I.D. card code includes information related to identification of said one of said plurality of persons for use in retrieving stored information associated with said one of said plurality of persons from said memory, and wherein a first case in which an I.D. card code of said one of said plurality of persons is sensed by one of said I.D. card readers at a first location within said facility results in a different interaction indication result than a second case in which said I.D. card code of said one of said plurality of persons is sensed by another of said I.D. card code readers at a second location within said facility that is different from said first location.

36. The method of claim 32, wherein the step (g) further comprises the step of indicating patient flow information on said display connected to said master processor.

37. The method of claim 32, further comprising the steps of sensing patient test data in patient test equipment that communicates with said master processor and transmitting said patient test data as said sensed real-time inputs to said master processor.

38. The method of claim 32, further comprising the steps of receiving real-time inputs at said master processor from a network processor that is connected to said master processor and a second master processor by a communications link, and transmitting real-time inputs from said master processor to said network processor and said second master processor with said communications link.

39. The method as set forth in claim 32, further comprising the step of transmitting a plurality of manual inputs from a personal computer processor to said master processor.

40. The method as set forth in claim 39, further comprising the steps of storing said manual inputs and said condition output in said memory as historical aspects, and selectively interacting said historical aspects with said real-time inputs to produce interaction indication results.

41. The method of claim 39, wherein:

(a) said real-time inputs are directly input to said master processor via a communication channel connecting at least one personal computer to said master processor, wherein said real-time inputs include sensed I.D. card codes which include information related to identification of users of said sensed I.D. card codes for use in retrieving stored information associated with said users from said memory, sensed selected test information, sensed test result information, final diagnosis information, prescription confirmation information, insurance verification information, standardized testing program information, health maintenance program information, patient appointment information, and requests for patient data exchange information;

(b) said manual inputs include patient historical aspects information, equipment maintenance information, employee schedules and rosters information, inventory information, costs information, and facility characteristics information; and (c) said real-time outputs include patient data and history information, an employee instruction information, an insurer invoice information, an appointment schedule information, an employee duty roster information, a maintenance schedule information, an inventory requirement information, a visit summary information, an insurer approval notification information, a patient referral information, and a profit and loss statement information for said facility.

42. The method of claim 32, wherein the step of continuously and automatically determining in real-time interactions and relationships between said real-time inputs includes the step of commanding certain of said real-time inputs to be held constant to act as comparators in order to sense changes in other of said real-time inputs.

43. The method of claim 32, wherein the step of continuously and automatically producing an interaction indication result includes the step of continuously and automatically producing a plurality of interaction indication results.

44. The method of claim 32, wherein the step of continuously and automatically producing a condition output includes the step of continuously and automatically producing a plurality of condition outputs.

45. The method of claim 44, wherein the step of automatically transmitting said condition output includes the step of automatically transmitting the plurality of condition outputs to a plurality of displays.

46. The method of claim 44 wherein said real-time inputs include a patient ID number and contents of a health care plan and said condition outputs include evaluations of the health care program.

47. The method of claim 39, wherein said real-time inputs include inputs that originate external to the facility.

48. The method of claim 32, wherein the step of producing a condition output includes the step of producing an automatic instruction to a lab room for indicating a priority of tests to be analyzed.

* * * * *